US007615217B2

(12) United States Patent
Gillies et al.

(10) Patent No.: US 7,615,217 B2
(45) **Date of Patent: *Nov. 10, 2009**

(54) ARTIFICIAL PROTEINS WITH REDUCED IMMUNOGENICITY

(75) Inventors: Stephen Gillies, Carlisle, MA (US); Francis J. Carr, Balmedie (GB); Jones Tim, Babraham (GB); Graham Carter, By Newmachar (GB); Anita Hamilton, Aberdeen (GB); Stephen Williams, Insch (GB); Marian Hanlon, Cambridge (GB); John Watkins, Girton (GB); Matthew Baker, Ely (GB); Jeffrey C. Way, Cambridge, MA (US)

(73) Assignee: Merck Patent GmbH, Darmstadt (DE)

( * ) Notice: Subject to any disclaimer, the term of this patent is extended or adjusted under 35 U.S.C. 154(b) by 154 days.

This patent is subject to a terminal disclaimer.

(21) Appl. No.: 11/716,878

(22) Filed: Mar. 12, 2007

(65) Prior Publication Data

US 2007/0269435 A1 Nov. 22, 2007

Related U.S. Application Data

(62) Division of application No. 10/468,370, filed as application No. PCT/EP02/01690 on Feb. 18, 2002, now Pat. No. 7,189,830.

(30) Foreign Application Priority Data

Feb. 19, 2001 (EP) ................................. 01103955
Apr. 5, 2001 (EP) ................................. 01108291

(51) Int. Cl.
*A61K 39/395* (2006.01)

(52) U.S. Cl. ................ 424/134.1; 424/133.1; 424/85.1; 424/85.2; 530/387.3

(58) Field of Classification Search ...................... None
See application file for complete search history.

(56) References Cited

U.S. PATENT DOCUMENTS 5,650,150 A * 7/1997 Gillies ..................... 424/134.1
7,132,511 B2 * 11/2006 Carr et al. ................ 530/387.3

* cited by examiner

*Primary Examiner*—Prema Mertz
(74) *Attorney, Agent, or Firm*—Olson & Cepuritis, Ltd.

(57) ABSTRACT

The invention relates to artificial modified proteins, preferably fusion proteins, having a reduced immunogenicity compared to the parent non-modified molecule when exposed to a species in vivo. The invention relates, above all, to novel immunoglobulin fusion proteins which essentially consist of an immunoglobulin molecule or a fragment thereof covalently fused via its C-terminus to the N-terminus of a biologically active non-immunoglobulin molecule, preferably a polypeptide or protein or a biologically active fragment thereof. In a specific embodiment, the invention relates to fusion proteins consisting of an Fc portion of an antibody which is fused as mentioned to the non-immunological target molecule which elicits biological or pharmacological efficacy. The molecules of the invention have amino acid sequences which are altered in one or more amino acid residue positions but have in principal the same biological activity as compared with the non-altered molecules. The changes are made in regions of the molecules which are identified as T-cell epitopes, which contribute to an immune reaction in a living host. Thus, the invention also relates to a novel method of making such fusion proteins by identifying said epitopes comprising calculation of T-cell epitope values for MHC Class II molecule binding sites in a peptide by computer-aided methods.

6 Claims, 6 Drawing Sheets

SEQUENCE LISTING

<160> NUMBER OF SEQ ID NOS: 689

<210> SEQ ID NO 1
<211> LENGTH: 8
<212> TYPE: PRT
<213> ORGANISM: Artificial Sequence
<220> FEATURE:
<223> OTHER INFORMATION: Linker Peptide

<400> SEQUENCE: 1

Gly Gly Gly Lys Gly Gly Gly Gly
1 5

-continued

<210> SEQ ID NO 2
<211> LENGTH: 8
<212> TYPE: PRT
<213> ORGANISM: Artificial Sequence
<220> FEATURE:
<223> OTHER INFORMATION: Linker peptide

<400> SEQUENCE: 2

Gly Gly Gly Asn Gly Ser Gly Gly
1 5

<210> SEQ ID NO 3
<211> LENGTH: 7
<212> TYPE: PRT
<213> ORGANISM: Artificial Sequence
<220> FEATURE:
<223> OTHER INFORMATION: Linker peptide

<400> SEQUENCE: 3

Gly Gly Gly Cys Gly Gly Gly
1 5

<210> SEQ ID NO 4
<211> LENGTH: 5
<212> TYPE: PRT
<213> ORGANISM: Artificial Sequence
<220> FEATURE:
<223> OTHER INFORMATION: Linker peptide

<400> SEQUENCE: 4

Gly Pro Asn Gly Gly
1 5

<210> SEQ ID NO 5
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 5

Val Pro Ile Gln Lys Val Gln Asp Asp Thr Lys Thr Leu
1 5 10

<210> SEQ ID NO 6
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 6

Gln Lys Val Gln Asp Asp Thr Lys Thr Leu Ile Lys Thr
1 5 10

<210> SEQ ID NO 7
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 7

Lys Thr Leu Ile Lys Thr Ile Val Thr Arg Ile Asn Asp
1 5 10

-continued

<210> SEQ ID NO 8
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 8

Thr Leu Ile Lys Thr Ile Val Thr Arg Ile Asn Asp Ile
1 5 10

<210> SEQ ID NO 9
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 9

Lys Thr Ile Val Thr Arg Ile Asn Asp Ile Ser His Thr
1 5 10

<210> SEQ ID NO 10
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 10

Thr Ile Val Thr Arg Ile Asn Asp Ile Ser His Thr Gln
1 5 10

<210> SEQ ID NO 11
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 11

Thr Arg Ile Asn Asp Ile Ser His Thr Gln Ser Val Ser
1 5 10

<210> SEQ ID NO 12
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 12

Asn Asp Ile Ser His Thr Gln Ser Val Ser Ser Lys Gln
1 5 10

<210> SEQ ID NO 13
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 13

Gln Ser Val Ser Ser Lys Gln Lys Val Thr Gly Leu Asp
1 5 10

<210> SEQ ID NO 14

-continued

<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 14

Ser Ser Lys Gln Lys Val Thr Gly Leu Asp Phe Ile Pro
1 5 10

<210> SEQ ID NO 15
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 15

Gln Lys Val Thr Gly Leu Asp Phe Ile Pro Gly Leu His
1 5 10

<210> SEQ ID NO 16
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 16

Thr Gly Leu Asp Phe Ile Pro Gly Leu His Pro Ile Leu
1 5 10

<210> SEQ ID NO 17
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 17

Leu Asp Phe Ile Pro Gly Leu His Pro Ile Leu Thr Leu
1 5 10

<210> SEQ ID NO 18
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 18

Asp Phe Ile Pro Gly Leu His Pro Ile Leu Thr Leu Ser
1 5 10

<210> SEQ ID NO 19
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 19

Pro Gly Leu His Pro Ile Leu Thr Leu Ser Lys Met Asp
1 5 10

<210> SEQ ID NO 20
<211> LENGTH: 13

-continued

<212> TYPE: PRT
<213> ORGANISM: Artificial Sequence
<220> FEATURE:
<223> OTHER INFORMATION: MHC class II binding epitope

<400> SEQUENCE: 20

Gly Leu His Pro Ile Leu Thr Leu Ser Lys Met Asp Gln
1 5 10

<210> SEQ ID NO 21
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 21

His Pro Ile Leu Thr Leu Ser Lys Met Asp Gln Thr Leu
1 5 10

<210> SEQ ID NO 22
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 22

Pro Ile Leu Thr Leu Ser Lys Met Asp Gln Thr Leu Ala
1 5 10

<210> SEQ ID NO 23
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 23

Leu Thr Leu Ser Lys Met Asp Gln Thr Leu Ala Val Tyr
1 5 10

<210> SEQ ID NO 24
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 24

Ser Lys Met Asp Gln Thr Leu Ala Val Tyr Gln Gln Ile
1 5 10

<210> SEQ ID NO 25
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 25

Gln Thr Leu Ala Val Tyr Gln Gln Ile Leu Thr Ser Met
1 5 10

<210> SEQ ID NO 26
<211> LENGTH: 13
<212> TYPE: PRT

-continued

```
<213> ORGANISM: Artificial Sequence
<220> FEATURE:
<223> OTHER INFORMATION: MHC class II binding epitope

<400> SEQUENCE: 26

Leu Ala Val Tyr Gln Gln Ile Leu Thr Ser Met Pro Ser
 1               5                   10


<210> SEQ ID NO 27
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 27

Ala Val Tyr Gln Gln Ile Leu Thr Ser Met Pro Ser Arg
 1               5                   10


<210> SEQ ID NO 28
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 28

Gln Gln Ile Leu Thr Ser Met Pro Ser Arg Asn Val Ile
 1               5                   10


<210> SEQ ID NO 29
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 29

Gln Ile Leu Thr Ser Met Pro Ser Arg Asn Val Ile Gln
 1               5                   10


<210> SEQ ID NO 30
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 30

Thr Ser Met Pro Ser Arg Asn Val Ile Gln Ile Ser Asn
 1               5                   10


<210> SEQ ID NO 31
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 31

Ser Arg Asn Val Ile Gln Ile Ser Asn Asp Leu Glu Asn
 1               5                   10


<210> SEQ ID NO 32
<211> LENGTH: 13
<212> TYPE: PRT
<213> ORGANISM: Artificial Sequence
```

-continued

<220> FEATURE:
<223> OTHER INFORMATION: MHC class II binding epitope

<400> SEQUENCE: 32

Arg Asn Val Ile Gln Ile Ser Asn Asp Leu Glu Asn Leu
1 5 10

<210> SEQ ID NO 33
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 33

Asn Val Ile Gln Ile Ser Asn Asp Leu Glu Asn Leu Arg
1 5 10

<210> SEQ ID NO 34
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 34

Ile Gln Ile Ser Asn Asp Leu Glu Asn Leu Arg Asp Leu
1 5 10

<210> SEQ ID NO 35
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 35

Asn Asp Leu Glu Asn Leu Arg Asp Leu Leu His Val Leu
1 5 10

<210> SEQ ID NO 36
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 36

Leu Glu Asn Leu Arg Asp Leu Leu His Val Leu Ala Phe
1 5 10

<210> SEQ ID NO 37
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 37

Glu Asn Leu Arg Asp Leu Leu His Val Leu Ala Phe Ser
1 5 10

<210> SEQ ID NO 38
<211> LENGTH: 13
<212> TYPE: PRT
<213> ORGANISM: Artificial Sequence
<220> FEATURE:

-continued

<223> OTHER INFORMATION: MHC class II binding epitope

<400> SEQUENCE: 38

Arg Asp Leu Leu His Val Leu Ala Phe Ser Lys Ser Cys
1 5 10

<210> SEQ ID NO 39
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 39

Asp Leu Leu His Val Leu Ala Phe Ser Lys Ser Cys His
1 5 10

<210> SEQ ID NO 40
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 40

Leu His Val Leu Ala Phe Ser Lys Ser Cys His Leu Pro
1 5 10

<210> SEQ ID NO 41
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 41

His Val Leu Ala Phe Ser Lys Ser Cys His Leu Pro Trp
1 5 10

<210> SEQ ID NO 42
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 42

Leu Ala Phe Ser Lys Ser Cys His Leu Pro Trp Ala Ser
1 5 10

<210> SEQ ID NO 43
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 43

Cys His Leu Pro Trp Ala Ser Gly Leu Glu Thr Leu Asp
1 5 10

<210> SEQ ID NO 44
<211> LENGTH: 13
<212> TYPE: PRT
<213> ORGANISM: Artificial Sequence
<220> FEATURE:
<223> OTHER INFORMATION: MHC class II binding epitope -continued

<400> SEQUENCE: 44

Ser Gly Leu Glu Thr Leu Asp Ser Leu Gly Gly Val Leu
1 5 10

<210> SEQ ID NO 45
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 45

Asp Ser Leu Gly Gly Val Leu Glu Ala Ser Gly Tyr Ser
1 5 10

<210> SEQ ID NO 46
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 46

Ser Leu Gly Gly Val Leu Glu Ala Ser Gly Tyr Ser Thr
1 5 10

<210> SEQ ID NO 47
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 47

Gly Gly Val Leu Glu Ala Ser Gly Tyr Ser Thr Glu Val
1 5 10

<210> SEQ ID NO 48
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 48

Ser Gly Tyr Ser Thr Glu Val Val Ala Leu Ser Arg Leu
1 5 10

<210> SEQ ID NO 49
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 49

Thr Glu Val Val Ala Leu Ser Arg Leu Gln Gly Ser Leu
1 5 10

<210> SEQ ID NO 50
<211> LENGTH: 13
<212> TYPE: PRT
<213> ORGANISM: Artificial Sequence
<220> FEATURE:
<223> OTHER INFORMATION: MHC class II binding epitope -continued

<400> SEQUENCE: 50

Glu Val Val Ala Leu Ser Arg Leu Gln Gly Ser Leu Gln
1 5 10

<210> SEQ ID NO 51
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 51

Val Ala Leu Ser Arg Leu Gln Gly Ser Leu Gln Asp Met
1 5 10

<210> SEQ ID NO 52
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 52

Ser Arg Leu Gln Gly Ser Leu Gln Asp Met Leu Trp Gln
1 5 10

<210> SEQ ID NO 53
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 53

Gln Gly Ser Leu Gln Asp Met Leu Trp Gln Leu Asp Leu
1 5 10

<210> SEQ ID NO 54
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 54

Gly Ser Leu Gln Asp Met Leu Trp Gln Leu Asp Leu Ser
1 5 10

<210> SEQ ID NO 55
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 55

Gln Asp Met Leu Trp Gln Leu Asp Leu Ser Pro Gly Cys
1 5 10

<210> SEQ ID NO 56
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 56

-continued

```
Arg Lys Ser Ser Lys Met Gln Ala Phe Arg Ile Trp Asp
 1               5                  10


<210> SEQ ID NO 57
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 57

Ser Lys Met Gln Ala Phe Arg Ile Trp Asp Val Asn Gln
 1               5                  10


<210> SEQ ID NO 58
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 58

Gln Ala Phe Arg Ile Trp Asp Val Asn Gln Lys Thr Phe
 1               5                  10


<210> SEQ ID NO 59
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 59

Phe Arg Ile Trp Asp Val Asn Gln Lys Thr Phe Tyr Leu
 1               5                  10


<210> SEQ ID NO 60
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 60

Arg Ile Trp Asp Val Asn Gln Lys Thr Phe Tyr Leu Arg
 1               5                  10


<210> SEQ ID NO 61
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 61

Ile Trp Asp Val Asn Gln Lys Thr Phe Tyr Leu Arg Asn
 1               5                  10


<210> SEQ ID NO 62
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 62
```

-continued

Trp Asp Val Asn Gln Lys Thr Phe Tyr Leu Arg Asn Asn
1 5 10

<210> SEQ ID NO 63
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 63

Lys Thr Phe Tyr Leu Arg Asn Asn Gln Leu Val Ala Gly
1 5 10

<210> SEQ ID NO 64
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 64

Thr Phe Tyr Leu Arg Asn Asn Gln Leu Val Ala Gly Tyr
1 5 10

<210> SEQ ID NO 65
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 65

Phe Tyr Leu Arg Asn Asn Gln Leu Val Ala Gly Tyr Leu
1 5 10

<210> SEQ ID NO 66
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 66

Leu Arg Asn Asn Gln Leu Val Ala Gly Tyr Leu Gln Gly
1 5 10

<210> SEQ ID NO 67
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 67

Arg Asn Asn Gln Leu Val Ala Gly Tyr Leu Gln Gly Pro
1 5 10

<210> SEQ ID NO 68
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 68

Asn Gln Leu Val Ala Gly Tyr Leu Gln Gly Pro Asn Val
1 5 10

<210> SEQ ID NO 69
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 69

Gln Leu Val Ala Gly Tyr Leu Gln Gly Pro Asn Val Asn
1 5 10

<210> SEQ ID NO 70
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 70

Leu Val Ala Gly Tyr Leu Gln Gly Pro Asn Val Asn Leu
1 5 10

<210> SEQ ID NO 71
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 71

Ala Gly Tyr Leu Gln Gly Pro Asn Val Asn Leu Glu Glu
1 5 10

<210> SEQ ID NO 72
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 72

Gly Tyr Leu Gln Gly Pro Asn Val Asn Leu Glu Glu Lys
1 5 10

<210> SEQ ID NO 73
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 73

Pro Asn Val Asn Leu Glu Glu Lys Ile Asp Val Val Pro
1 5 10

<210> SEQ ID NO 74
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 74

Val Asn Leu Glu Glu Lys Ile Asp Val Val Pro Ile Glu
1 5 10

<210> SEQ ID NO 75
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 75

Glu Lys Ile Asp Val Val Pro Ile Glu Pro His Ala Leu
1 5 10

<210> SEQ ID NO 76
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 76

Ile Asp Val Val Pro Ile Glu Pro His Ala Leu Phe Leu
1 5 10

<210> SEQ ID NO 77
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 77

Asp Val Val Pro Ile Glu Pro His Ala Leu Phe Leu Gly
1 5 10

<210> SEQ ID NO 78
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 78

Val Pro Ile Glu Pro His Ala Leu Phe Leu Gly Ile His
1 5 10

<210> SEQ ID NO 79
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 79

His Ala Leu Phe Leu Gly Ile His Gly Gly Lys Met Cys
1 5 10

<210> SEQ ID NO 80
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 80

-continued

Ala Leu Phe Leu Gly Ile His Gly Gly Lys Met Cys Leu
1 5 10

<210> SEQ ID NO 81
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 81

Leu Phe Leu Gly Ile His Gly Gly Lys Met Cys Leu Ser
1 5 10

<210> SEQ ID NO 82
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 82

Leu Gly Ile His Gly Gly Lys Met Cys Leu Ser Cys Val
1 5 10

<210> SEQ ID NO 83
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 83

Gly Lys Met Cys Leu Ser Cys Val Lys Ser Gly Asp Glu
1 5 10

<210> SEQ ID NO 84
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 84

Met Cys Leu Ser Cys Val Lys Ser Gly Asp Glu Thr Arg
1 5 10

<210> SEQ ID NO 85
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 85

Ser Cys Val Lys Ser Gly Asp Glu Thr Arg Leu Gln Leu
1 5 10

<210> SEQ ID NO 86
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 86

-continued

Glu Thr Arg Leu Gln Leu Glu Ala Val Asn Ile Thr Asp
1 5 10

<210> SEQ ID NO 87
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 87

Thr Arg Leu Gln Leu Glu Ala Val Asn Ile Thr Asp Leu
1 5 10

<210> SEQ ID NO 88
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 88

Leu Gln Leu Glu Ala Val Asn Ile Thr Asp Leu Ser Glu
1 5 10

<210> SEQ ID NO 89
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 89

Glu Ala Val Asn Ile Thr Asp Leu Ser Glu Asn Arg Lys
1 5 10

<210> SEQ ID NO 90
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 90

Val Asn Ile Thr Asp Leu Ser Glu Asn Arg Lys Gln Asp
1 5 10

<210> SEQ ID NO 91
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 91

Thr Asp Leu Ser Glu Asn Arg Lys Gln Asp Lys Arg Phe
1 5 10

<210> SEQ ID NO 92
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 92

Glu Asn Arg Lys Gln Asp Lys Arg Phe Ala Phe Ile Arg
1 5 10

<210> SEQ ID NO 93
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 93

Lys Arg Phe Ala Phe Ile Arg Ser Asp Ser Gly Pro Thr
1 5 10

<210> SEQ ID NO 94
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 94

Phe Ala Phe Ile Arg Ser Asp Ser Gly Pro Thr Thr Ser
1 5 10

<210> SEQ ID NO 95
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 95

Ala Phe Ile Arg Ser Asp Ser Gly Pro Thr Thr Ser Phe
1 5 10

<210> SEQ ID NO 96
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 96

Thr Ser Phe Glu Ser Ala Ala Cys Pro Gly Trp Phe Leu
1 5 10

<210> SEQ ID NO 97
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 97

Ser Phe Glu Ser Ala Ala Cys Pro Gly Trp Phe Leu Cys
1 5 10

<210> SEQ ID NO 98
<211> LENGTH: 13
<212> TYPE: PRT
<213> ORGANISM: Artificial Sequence
<220> FEATURE:
<223> OTHER INFORMATION: MHC class II binding epitope -continued

<400> SEQUENCE: 98

Pro Gly Trp Phe Leu Cys Thr Ala Met Glu Ala Asp Gln
1 5 10

<210> SEQ ID NO 99
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 99

Trp Phe Leu Cys Thr Ala Met Glu Ala Asp Gln Pro Val
1 5 10

<210> SEQ ID NO 100
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 100

Thr Ala Met Glu Ala Asp Gln Pro Val Ser Leu Thr Asn
1 5 10

<210> SEQ ID NO 101
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 101

Gln Pro Val Ser Leu Thr Asn Met Pro Asp Glu Gly Val
1 5 10

<210> SEQ ID NO 102
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 102

Val Ser Leu Thr Asn Met Pro Asp Glu Gly Val Met Val
1 5 10

<210> SEQ ID NO 103
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 103

Thr Asn Met Pro Asp Glu Gly Val Met Val Thr Lys Phe
1 5 10

<210> SEQ ID NO 104
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 104

-continued

Pro Asp Glu Gly Val Met Val Thr Lys Phe Tyr Phe Gln
1 5 10

<210> SEQ ID NO 105
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 105

Glu Gly Val Met Val Thr Lys Phe Tyr Phe Gln Glu Asp
1 5 10

<210> SEQ ID NO 106
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 106

Gly Val Met Val Thr Lys Phe Tyr Phe Gln Glu Asp Glu
1 5 10

<210> SEQ ID NO 107
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 107

Gly Glu Leu Ser Val Cys Asp Ser Ile Ser Glu Trp Val
1 5 10

<210> SEQ ID NO 108
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 108

Leu Ser Val Cys Asp Ser Ile Ser Glu Trp Val Thr Ala
1 5 10

<210> SEQ ID NO 109
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 109

Asp Ser Ile Ser Glu Trp Val Thr Ala Ala Asp Lys Lys
1 5 10

<210> SEQ ID NO 110
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 110

-continued

Ser Glu Trp Val Thr Ala Ala Asp Lys Lys Thr Ala Val
1 5 10

<210> SEQ ID NO 111
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 111

Glu Trp Val Thr Ala Ala Asp Lys Lys Thr Ala Val Asp
1 5 10

<210> SEQ ID NO 112
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 112

Trp Val Thr Ala Ala Asp Lys Lys Thr Ala Val Asp Met
1 5 10

<210> SEQ ID NO 113
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 113

Lys Thr Ala Val Asp Met Ser Gly Gly Thr Val Thr Val
1 5 10

<210> SEQ ID NO 114
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 114

Thr Ala Val Asp Met Ser Gly Gly Thr Val Thr Val Leu
1 5 10

<210> SEQ ID NO 115
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 115

Val Asp Met Ser Gly Gly Thr Val Thr Val Leu Glu Lys
1 5 10

<210> SEQ ID NO 116
<211> LENGTH: 13
<212> TYPE: PRT
<213> ORGANISM: Artificial Sequence
<220> FEATURE:
<223> OTHER INFORMATION: MHC class II binding epitope -continued

<400> SEQUENCE: 116

Gly Thr Val Thr Val Leu Glu Lys Val Pro Val Ser Lys
 1               5                   10

<210> SEQ ID NO 117
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 117

Val Thr Val Leu Glu Lys Val Pro Val Ser Lys Gly Gln
 1               5                   10

<210> SEQ ID NO 118
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 118

Thr Val Leu Glu Lys Val Pro Val Ser Lys Gly Gln Leu
 1               5                   10

<210> SEQ ID NO 119
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 119

Glu Lys Val Pro Val Ser Lys Gly Gln Leu Lys Gln Tyr
 1               5                   10

<210> SEQ ID NO 120
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 120

Val Pro Val Ser Lys Gly Gln Leu Lys Gln Tyr Phe Tyr
 1               5                   10

<210> SEQ ID NO 121
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 121

Gly Gln Leu Lys Gln Tyr Phe Tyr Glu Thr Lys Cys Asn
 1               5                   10

<210> SEQ ID NO 122
<211> LENGTH: 13
<212> TYPE: PRT
<213> ORGANISM: Artificial Sequence
<220> FEATURE:
<223> OTHER INFORMATION: MHC class II binding epitope -continued

<400> SEQUENCE: 122

Lys Gln Tyr Phe Tyr Glu Thr Lys Cys Asn Pro Met Gly
1 5 10

<210> SEQ ID NO 123
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 123

Gln Tyr Phe Tyr Glu Thr Lys Cys Asn Pro Met Gly Tyr
1 5 10

<210> SEQ ID NO 124
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 124

Tyr Phe Tyr Glu Thr Lys Cys Asn Pro Met Gly Tyr Thr
1 5 10

<210> SEQ ID NO 125
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 125

Asn Pro Met Gly Tyr Thr Lys Glu Gly Cys Arg Gly Ile
1 5 10

<210> SEQ ID NO 126
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 126

Met Gly Tyr Thr Lys Glu Gly Cys Arg Gly Ile Asp Lys
1 5 10

<210> SEQ ID NO 127
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 127

Arg Gly Ile Asp Lys Arg His Trp Asn Ser Gln Cys Arg
1 5 10

<210> SEQ ID NO 128
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 128

-continued

Arg His Trp Asn Ser Gln Cys Arg Thr Thr Gln Ser Tyr
 1 5 10

<210> SEQ ID NO 129
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 129

His Trp Asn Ser Gln Cys Arg Thr Thr Gln Ser Tyr Val
 1 5 10

<210> SEQ ID NO 130
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 130

Gln Ser Tyr Val Arg Ala Leu Thr Met Asp Ser Lys Lys
 1 5 10

<210> SEQ ID NO 131
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 131

Ser Tyr Val Arg Ala Leu Thr Met Asp Ser Lys Lys Arg
 1 5 10

<210> SEQ ID NO 132
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 132

Arg Ala Leu Thr Met Asp Ser Lys Lys Arg Ile Gly Trp
 1 5 10

<210> SEQ ID NO 133
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 133

Leu Thr Met Asp Ser Lys Lys Arg Ile Gly Trp Arg Phe
 1 5 10

<210> SEQ ID NO 134
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 134

-continued

```
Lys Arg Ile Gly Trp Arg Phe Ile Arg Ile Asp Thr Ser
 1               5                  10


<210> SEQ ID NO 135
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 135

Ile Gly Trp Arg Phe Ile Arg Ile Asp Thr Ser Cys Val
 1               5                  10


<210> SEQ ID NO 136
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 136

Gly Trp Arg Phe Ile Arg Ile Asp Thr Ser Cys Val Cys
 1               5                  10


<210> SEQ ID NO 137
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 137

Trp Arg Phe Ile Arg Ile Asp Thr Ser Cys Val Cys Thr
 1               5                  10


<210> SEQ ID NO 138
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 138

Arg Phe Ile Arg Ile Asp Thr Ser Cys Val Cys Thr Leu
 1               5                  10


<210> SEQ ID NO 139
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 139

Ile Arg Ile Asp Thr Ser Cys Val Cys Thr Leu Thr Ile
 1               5                  10


<210> SEQ ID NO 140
<211> LENGTH: 13
<212> TYPE: PRT
<213> ORGANISM: Artificial Sequence
<220> FEATURE:
<223> OTHER INFORMATION: MHC class II binding epitope
```

-continued

<400> SEQUENCE: 140

Ile Asp Thr Ser Cys Val Cys Thr Leu Thr Ile Lys Arg
1 5 10

<210> SEQ ID NO 141
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 141

Pro Arg Leu Ile Cys Asp Ser Arg Val Leu Glu Arg Tyr
1 5 10

<210> SEQ ID NO 142
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 142

Arg Leu Ile Cys Asp Ser Arg Val Leu Glu Arg Tyr Leu
1 5 10

<210> SEQ ID NO 143
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 143

Ile Cys Asp Ser Arg Val Leu Glu Arg Tyr Leu Leu Glu
1 5 10

<210> SEQ ID NO 144
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 144

Cys Asp Ser Arg Val Leu Glu Arg Tyr Leu Leu Glu Ala
1 5 10

<210> SEQ ID NO 145
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 145

Ser Arg Val Leu Glu Arg Tyr Leu Leu Glu Ala Lys Glu
1 5 10

<210> SEQ ID NO 146
<211> LENGTH: 13
<212> TYPE: PRT
<213> ORGANISM: Artificial Sequence
<220> FEATURE:
<223> OTHER INFORMATION: MHC class II binding epitope -continued

<400> SEQUENCE: 146

Arg Val Leu Glu Arg Tyr Leu Leu Glu Ala Lys Glu Ala
1 5 10

<210> SEQ ID NO 147
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 147

Leu Glu Arg Tyr Leu Leu Glu Ala Lys Glu Ala Glu Asn
1 5 10

<210> SEQ ID NO 148
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 148

Glu Arg Tyr Leu Leu Glu Ala Lys Glu Ala Glu Asn Ile
1 5 10

<210> SEQ ID NO 149
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 149

Arg Tyr Leu Leu Glu Ala Lys Glu Ala Glu Asn Ile Thr
1 5 10

<210> SEQ ID NO 150
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 150

Tyr Leu Leu Glu Ala Lys Glu Ala Glu Asn Ile Thr Thr
1 5 10

<210> SEQ ID NO 151
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 151

Leu Glu Ala Lys Glu Ala Glu Asn Ile Thr Thr Gly Cys
1 5 10

<210> SEQ ID NO 152
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 152

-continued

```
Lys Glu Ala Glu Asn Ile Thr Thr Gly Cys Ala Glu His
 1               5                   10
```

<210> SEQ ID NO 153
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 153

```
Glu Asn Ile Thr Thr Gly Cys Ala Glu His Cys Ser Leu
 1               5                   10
```

<210> SEQ ID NO 154
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 154

```
Cys Ser Leu Asn Glu Asn Ile Thr Val Pro Asp Thr Lys
 1               5                   10
```

<210> SEQ ID NO 155
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 155

```
Asn Glu Asn Ile Thr Val Pro Asp Thr Lys Val Asn Phe
 1               5                   10
```

<210> SEQ ID NO 156
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 156

```
Glu Asn Ile Thr Val Pro Asp Thr Lys Val Asn Phe Tyr
 1               5                   10
```

<210> SEQ ID NO 157
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 157

```
Asn Ile Thr Val Pro Asp Thr Lys Val Asn Phe Tyr Ala
 1               5                   10
```

<210> SEQ ID NO 158
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 158

-continued

Ile Thr Val Pro Asp Thr Lys Val Asn Phe Tyr Ala Trp
1 5 10

<210> SEQ ID NO 159
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 159

Thr Lys Val Asn Phe Tyr Ala Trp Lys Arg Met Glu Val
1 5 10

<210> SEQ ID NO 160
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 160

Val Asn Phe Tyr Ala Trp Lys Arg Met Glu Val Gly Gln
1 5 10

<210> SEQ ID NO 161
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 161

Asn Phe Tyr Ala Trp Lys Arg Met Glu Val Gly Gln Gln
1 5 10

<210> SEQ ID NO 162
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 162

Tyr Ala Trp Lys Arg Met Glu Val Gly Gln Gln Ala Val
1 5 10

<210> SEQ ID NO 163
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 163

Lys Arg Met Glu Val Gly Gln Gln Ala Val Glu Val Trp
1 5 10

<210> SEQ ID NO 164
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 164

Arg Met Glu Val Gly Gln Gln Ala Val Glu Val Trp Gln
1 5 10

<210> SEQ ID NO 165
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 165

Met Glu Val Gly Gln Gln Ala Val Glu Val Trp Gln Gly
1 5 10

<210> SEQ ID NO 166
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 166

Gln Ala Val Glu Val Trp Gln Gly Leu Ala Leu Leu Ser
1 5 10

<210> SEQ ID NO 167
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 167

Ala Val Glu Val Trp Gln Gly Leu Ala Leu Leu Ser Glu
1 5 10

<210> SEQ ID NO 168
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 168

Val Glu Val Trp Gln Gly Leu Ala Leu Leu Ser Glu Ala
1 5 10

<210> SEQ ID NO 169
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 169

Glu Val Trp Gln Gly Leu Ala Leu Leu Ser Glu Ala Val
1 5 10

<210> SEQ ID NO 170
<211> LENGTH: 13
<212> TYPE: PRT
<213> ORGANISM: Artificial Sequence
<220> FEATURE:
<223> OTHER INFORMATION: MHC class II binding epitope -continued

<400> SEQUENCE: 170

Val Trp Gln Gly Leu Ala Leu Leu Ser Glu Ala Val Leu
1 5 10

<210> SEQ ID NO 171
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 171

Trp Gln Gly Leu Ala Leu Leu Ser Glu Ala Val Leu Arg
1 5 10

<210> SEQ ID NO 172
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 172

Gln Gly Leu Ala Leu Leu Ser Glu Ala Val Leu Arg Gly
1 5 10

<210> SEQ ID NO 173
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 173

Leu Ala Leu Leu Ser Glu Ala Val Leu Arg Gly Gln Ala
1 5 10

<210> SEQ ID NO 174
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 174

Ala Leu Leu Ser Glu Ala Val Leu Arg Gly Gln Ala Leu
1 5 10

<210> SEQ ID NO 175
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 175

Leu Ser Glu Ala Val Leu Arg Gly Gln Ala Leu Leu Val
1 5 10

<210> SEQ ID NO 176
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 176

-continued

Ser Glu Ala Val Leu Arg Gly Gln Ala Leu Leu Val Asn
1 5 10

<210> SEQ ID NO 177
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 177

Glu Ala Val Leu Arg Gly Gln Ala Leu Leu Val Asn Ser
1 5 10

<210> SEQ ID NO 178
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 178

Ala Val Leu Arg Gly Gln Ala Leu Leu Val Asn Ser Ser
1 5 10

<210> SEQ ID NO 179
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 179

Gln Ala Leu Leu Val Asn Ser Ser Gln Pro Trp Glu Pro
1 5 10

<210> SEQ ID NO 180
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 180

Ala Leu Leu Val Asn Ser Ser Gln Pro Trp Glu Pro Leu
1 5 10

<210> SEQ ID NO 181
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 181

Leu Leu Val Asn Ser Ser Gln Pro Trp Glu Pro Leu Gln
1 5 10

<210> SEQ ID NO 182
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 182

-continued

```
Gln Pro Trp Glu Pro Leu Gln Leu His Val Asp Lys Ala
 1              5                   10


<210> SEQ ID NO 183
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 183

Glu Pro Leu Gln Leu His Val Asp Lys Ala Val Ser Gly
 1              5                   10


<210> SEQ ID NO 184
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 184

Leu Gln Leu His Val Asp Lys Ala Val Ser Gly Leu Arg
 1              5                   10


<210> SEQ ID NO 185
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 185

Leu His Val Asp Lys Ala Val Ser Gly Leu Arg Ser Leu
 1              5                   10


<210> SEQ ID NO 186
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 186

Lys Ala Val Ser Gly Leu Arg Ser Leu Thr Thr Leu Leu
 1              5                   10


<210> SEQ ID NO 187
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 187

Ser Gly Leu Arg Ser Leu Thr Thr Leu Leu Arg Ala Leu
 1              5                   10


<210> SEQ ID NO 188
<211> LENGTH: 13
<212> TYPE: PRT
<213> ORGANISM: Artificial Sequence
<220> FEATURE:
<223> OTHER INFORMATION: MHC class II binding epitope
```

<400> SEQUENCE: 188

Arg Ser Leu Thr Thr Leu Leu Arg Ala Leu Gly Ala Gln
1 5 10

<210> SEQ ID NO 189
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 189

Ser Leu Thr Thr Leu Leu Arg Ala Leu Gly Ala Gln Lys
1 5 10

<210> SEQ ID NO 190
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 190

Thr Thr Leu Leu Arg Ala Leu Gly Ala Gln Lys Glu Ala
1 5 10

<210> SEQ ID NO 191
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 191

Thr Leu Leu Arg Ala Leu Gly Ala Gln Lys Glu Ala Ile
1 5 10

<210> SEQ ID NO 192
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 192

Arg Ala Leu Gly Ala Gln Lys Glu Ala Ile Ser Pro Pro
1 5 10

<210> SEQ ID NO 193
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 193

Ala Gln Lys Glu Ala Ile Ser Pro Pro Asp Ala Ala Ser
1 5 10

<210> SEQ ID NO 194
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 194

Glu Ala Ile Ser Pro Pro Asp Ala Ala Ser Ala Ala Pro
1 5 10

<210> SEQ ID NO 195
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 195

Ser Pro Pro Asp Ala Ala Ser Ala Ala Pro Leu Arg Thr
1 5 10

<210> SEQ ID NO 196
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 196

Ala Ser Ala Ala Pro Leu Arg Thr Ile Thr Ala Asp Thr
1 5 10

<210> SEQ ID NO 197
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 197

Ala Pro Leu Arg Thr Ile Thr Ala Asp Thr Phe Arg Lys
1 5 10

<210> SEQ ID NO 198
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 198

Arg Thr Ile Thr Ala Asp Thr Phe Arg Lys Leu Phe Arg
1 5 10

<210> SEQ ID NO 199
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 199

Thr Ile Thr Ala Asp Thr Phe Arg Lys Leu Phe Arg Val
1 5 10

<210> SEQ ID NO 200
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 200

-continued

```
Asp Thr Phe Arg Lys Leu Phe Arg Val Tyr Ser Asn Phe
 1               5                   10


<210> SEQ ID NO 201
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 201

Arg Lys Leu Phe Arg Val Tyr Ser Asn Phe Leu Arg Gly
 1               5                   10


<210> SEQ ID NO 202
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 202

Lys Leu Phe Arg Val Tyr Ser Asn Phe Leu Arg Gly Lys
 1               5                   10


<210> SEQ ID NO 203
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 203

Phe Arg Val Tyr Ser Asn Phe Leu Arg Gly Lys Leu Lys
 1               5                   10


<210> SEQ ID NO 204
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 204

Arg Val Tyr Ser Asn Phe Leu Arg Gly Lys Leu Lys Leu
 1               5                   10


<210> SEQ ID NO 205
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 205

Tyr Ser Asn Phe Leu Arg Gly Lys Leu Lys Leu Tyr Thr
 1               5                   10


<210> SEQ ID NO 206
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 206
```

-continued

Ser Asn Phe Leu Arg Gly Lys Leu Lys Leu Tyr Thr Gly
1 5 10

<210> SEQ ID NO 207
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 207

Asn Phe Leu Arg Gly Lys Leu Lys Leu Tyr Thr Gly Glu
1 5 10

<210> SEQ ID NO 208
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 208

Arg Gly Lys Leu Lys Leu Tyr Thr Gly Glu Ala Cys Arg
1 5 10

<210> SEQ ID NO 209
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 209

Gly Lys Leu Lys Leu Tyr Thr Gly Glu Ala Cys Arg Thr
1 5 10

<210> SEQ ID NO 210
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 210

Leu Lys Leu Tyr Thr Gly Glu Ala Cys Arg Thr Gly Asp
1 5 10

<210> SEQ ID NO 211
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 211

Lys Leu Tyr Thr Gly Glu Ala Cys Arg Thr Gly Asp Arg
1 5 10

<210> SEQ ID NO 212
<211> LENGTH: 13
<212> TYPE: PRT
<213> ORGANISM: Artificial Sequence
<220> FEATURE:
<223> OTHER INFORMATION: MHC class II binding epitope -continued

<400> SEQUENCE: 212

Thr Pro Leu Gly Pro Ala Ser Ser Leu Pro Gln Ser Phe
1 5 10

<210> SEQ ID NO 213
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 213

Ser Ser Leu Pro Gln Ser Phe Leu Leu Lys Cys Leu Glu
1 5 10

<210> SEQ ID NO 214
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 214

Gln Ser Phe Leu Leu Lys Cys Leu Glu Gln Val Arg Lys
1 5 10

<210> SEQ ID NO 215
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 215

Ser Phe Leu Leu Lys Cys Leu Glu Gln Val Arg Lys Ile
1 5 10

<210> SEQ ID NO 216
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 216

Phe Leu Leu Lys Cys Leu Glu Gln Val Arg Lys Ile Gln
1 5 10

<210> SEQ ID NO 217
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 217

Lys Cys Leu Glu Gln Val Arg Lys Ile Gln Gly Asp Gly
1 5 10

<210> SEQ ID NO 218
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 218

Glu Gln Val Arg Lys Ile Gln Gly Asp Gly Ala Ala Leu
1 5 10

<210> SEQ ID NO 219
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 219

Arg Lys Ile Gln Gly Asp Gly Ala Ala Leu Gln Glu Lys
1 5 10

<210> SEQ ID NO 220
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 220

Ala Ala Leu Gln Glu Lys Leu Val Ser Glu Cys Ala Thr
1 5 10

<210> SEQ ID NO 221
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 221

Glu Lys Leu Val Ser Glu Cys Ala Thr Tyr Lys Leu Cys
1 5 10

<210> SEQ ID NO 222
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 222

Lys Leu Val Ser Glu Cys Ala Thr Tyr Lys Leu Cys His
1 5 10

<210> SEQ ID NO 223
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 223

Ala Ala Leu Gln Glu Lys Leu Cys Ala Thr Tyr Lys Leu
1 5 10

<210> SEQ ID NO 224
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 224

-continued

Glu Lys Leu Cys Ala Thr Tyr Lys Leu Cys His Pro Glu
1 5 10

<210> SEQ ID NO 225
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 225

Ala Thr Tyr Lys Leu Cys His Pro Glu Glu Leu Val Leu
1 5 10

<210> SEQ ID NO 226
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 226

Tyr Lys Leu Cys His Pro Glu Glu Leu Val Leu Leu Gly
1 5 10

<210> SEQ ID NO 227
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 227

Glu Glu Leu Val Leu Leu Gly His Ser Leu Gly Ile Pro
1 5 10

<210> SEQ ID NO 228
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 228

Glu Leu Val Leu Leu Gly His Ser Leu Gly Ile Pro Trp
1 5 10

<210> SEQ ID NO 229
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 229

His Ser Leu Gly Ile Pro Trp Ala Pro Leu Ser Ser Cys
1 5 10

<210> SEQ ID NO 230
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 230

-continued

```
Ile Pro Trp Ala Pro Leu Ser Ser Cys Pro Ser Gln Ala
 1               5                   10


<210> SEQ ID NO 231
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 231

Ala Pro Leu Ser Ser Cys Pro Ser Gln Ala Leu Gln Leu
 1               5                   10


<210> SEQ ID NO 232
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 232

Gln Ala Leu Gln Leu Ala Gly Cys Leu Ser Gln Leu His
 1               5                   10


<210> SEQ ID NO 233
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 233

Gly Cys Leu Ser Gln Leu His Ser Gly Leu Phe Leu Tyr
 1               5                   10


<210> SEQ ID NO 234
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 234

Ser Gln Leu His Ser Gly Leu Phe Leu Tyr Gln Gly Leu
 1               5                   10


<210> SEQ ID NO 235
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 235

Ser Gly Leu Phe Leu Tyr Gln Gly Leu Leu Gln Ala Leu
 1               5                   10


<210> SEQ ID NO 236
<211> LENGTH: 13
<212> TYPE: PRT
<213> ORGANISM: Artificial Sequence
<220> FEATURE:
<223> OTHER INFORMATION: MHC class II binding epitope
```

-continued

<400> SEQUENCE: 236

Gly Leu Phe Leu Tyr Gln Gly Leu Leu Gln Ala Leu Glu
1 5 10

<210> SEQ ID NO 237
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 237

Leu Phe Leu Tyr Gln Gly Leu Leu Gln Ala Leu Glu Gly
1 5 10

<210> SEQ ID NO 238
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 238

Phe Leu Tyr Gln Gly Leu Leu Gln Ala Leu Glu Gly Ile
1 5 10

<210> SEQ ID NO 239
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 239

Gln Gly Leu Leu Gln Ala Leu Glu Gly Ile Ser Pro Glu
1 5 10

<210> SEQ ID NO 240
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 240

Gly Leu Leu Gln Ala Leu Glu Gly Ile Ser Pro Glu Leu
1 5 10

<210> SEQ ID NO 241
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 241

Gln Ala Leu Glu Gly Ile Ser Pro Glu Leu Gly Pro Thr
1 5 10

<210> SEQ ID NO 242
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 242

Glu Gly Ile Ser Pro Glu Leu Gly Pro Thr Leu Asp Thr
1 5 10

<210> SEQ ID NO 243
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 243

Pro Thr Leu Asp Thr Leu Gln Leu Asp Val Ala Asp Phe
1 5 10

<210> SEQ ID NO 244
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 244

Asp Thr Leu Gln Leu Asp Val Ala Asp Phe Ala Thr Thr
1 5 10

<210> SEQ ID NO 245
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 245

Leu Gln Leu Asp Val Ala Asp Phe Ala Thr Thr Ile Trp
1 5 10

<210> SEQ ID NO 246
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 246

Leu Asp Val Ala Asp Phe Ala Thr Thr Ile Trp Gln Gln
1 5 10

<210> SEQ ID NO 247
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 247

Thr Thr Ile Trp Gln Gln Met Glu Glu Leu Gly Met Ala
1 5 10

<210> SEQ ID NO 248
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 248

-continued

Thr Ile Trp Gln Gln Met Glu Glu Leu Gly Met Ala Pro
1 5 10

<210> SEQ ID NO 249
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 249

Gln Gln Met Glu Glu Leu Gly Met Ala Pro Ala Leu Gln
1 5 10

<210> SEQ ID NO 250
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 250

Glu Glu Leu Gly Met Ala Pro Ala Leu Gln Pro Thr Gln
1 5 10

<210> SEQ ID NO 251
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 251

Leu Gly Met Ala Pro Ala Leu Gln Pro Thr Gln Gly Ala
1 5 10

<210> SEQ ID NO 252
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 252

Pro Ala Leu Gln Pro Thr Gln Gly Ala Met Pro Ala Phe
1 5 10

<210> SEQ ID NO 253
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 253

Gly Ala Met Pro Ala Phe Ala Ser Ala Phe Gln Arg Arg
1 5 10

<210> SEQ ID NO 254
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 254

-continued

Pro Ala Phe Ala Ser Ala Phe Gln Arg Arg Ala Gly Gly
1 5 10

<210> SEQ ID NO 255
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 255

Ser Ala Phe Gln Arg Arg Ala Gly Gly Val Leu Val Ala
1 5 10

<210> SEQ ID NO 256
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 256

Gly Gly Val Leu Val Ala Ser His Leu Gln Ser Phe Leu
1 5 10

<210> SEQ ID NO 257
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 257

Gly Val Leu Val Ala Ser His Leu Gln Ser Phe Leu Glu
1 5 10

<210> SEQ ID NO 258
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 258

Val Leu Val Ala Ser His Leu Gln Ser Phe Leu Glu Val
1 5 10

<210> SEQ ID NO 259
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 259

Ser His Leu Gln Ser Phe Leu Glu Val Ser Tyr Arg Val
1 5 10

<210> SEQ ID NO 260
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 260

Gln Ser Phe Leu Glu Val Ser Tyr Arg Val Leu Arg His
 1               5                  10

<210> SEQ ID NO 261
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 261

Ser Phe Leu Glu Val Ser Tyr Arg Val Leu Arg His Leu
 1               5                  10

<210> SEQ ID NO 262
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 262

Leu Glu Val Ser Tyr Arg Val Leu Arg His Leu Ala Gln
 1               5                  10

<210> SEQ ID NO 263
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 263

Asn Asp Met Thr Pro Glu Gln Met Ala Thr Asn Val Asn
 1               5                  10

<210> SEQ ID NO 264
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 264

Asp Met Thr Pro Glu Gln Met Ala Thr Asn Val Asn Cys
 1               5                  10

<210> SEQ ID NO 265
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 265

Glu Gln Met Ala Thr Asn Val Asn Cys Ser Ser Pro Glu
 1               5                  10

<210> SEQ ID NO 266
<211> LENGTH: 13
<212> TYPE: PRT
<213> ORGANISM: Artificial Sequence
<220> FEATURE:
<223> OTHER INFORMATION: MHC class II binding epitope -continued

<400> SEQUENCE: 266

Thr Asn Val Asn Cys Ser Ser Pro Glu Arg His Thr Arg
1 5 10

<210> SEQ ID NO 267
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 267

Arg Ser Tyr Asp Tyr Met Glu Gly Gly Asp Ile Arg Val
1 5 10

<210> SEQ ID NO 268
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 268

Tyr Asp Tyr Met Glu Gly Gly Asp Ile Arg Val Arg Arg
1 5 10

<210> SEQ ID NO 269
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 269

Asp Tyr Met Glu Gly Gly Asp Ile Arg Val Arg Arg Leu
1 5 10

<210> SEQ ID NO 270
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 270

Gly Asp Ile Arg Val Arg Arg Leu Phe Cys Arg Thr Gln
1 5 10

<210> SEQ ID NO 271
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 271

Ile Arg Val Arg Arg Leu Phe Cys Arg Thr Gln Trp Tyr
1 5 10

<210> SEQ ID NO 272
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 272

Arg Arg Leu Phe Cys Arg Thr Gln Trp Tyr Leu Arg Ile
1 5 10

<210> SEQ ID NO 273
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 273

Arg Leu Phe Cys Arg Thr Gln Trp Tyr Leu Arg Ile Asp
1 5 10

<210> SEQ ID NO 274
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 274

Thr Gln Trp Tyr Leu Arg Ile Asp Lys Arg Gly Lys Val
1 5 10

<210> SEQ ID NO 275
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 275

Gln Trp Tyr Leu Arg Ile Asp Lys Arg Gly Lys Val Lys
1 5 10

<210> SEQ ID NO 276
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 276

Trp Tyr Leu Arg Ile Asp Lys Arg Gly Lys Val Lys Gly
1 5 10

<210> SEQ ID NO 277
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 277

Leu Arg Ile Asp Lys Arg Gly Lys Val Lys Gly Thr Gln
1 5 10

<210> SEQ ID NO 278
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 278

-continued

Gly Lys Val Lys Gly Thr Gln Glu Met Lys Asn Asn Tyr
1 5 10

<210> SEQ ID NO 279
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 279

Gln Glu Met Lys Asn Asn Tyr Asn Ile Met Glu Ile Arg
1 5 10

<210> SEQ ID NO 280
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 280

Asn Asn Tyr Asn Ile Met Glu Ile Arg Thr Val Ala Val
1 5 10

<210> SEQ ID NO 281
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 281

Tyr Asn Ile Met Glu Ile Arg Thr Val Ala Val Gly Ile
1 5 10

<210> SEQ ID NO 282
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 282

Asn Ile Met Glu Ile Arg Thr Val Ala Val Gly Ile Val
1 5 10

<210> SEQ ID NO 283
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 283

Met Glu Ile Arg Thr Val Ala Val Gly Ile Val Ala Ile
1 5 10

<210> SEQ ID NO 284
<211> LENGTH: 13
<212> TYPE: PRT
<213> ORGANISM: Artificial Sequence
<220> FEATURE:
<223> OTHER INFORMATION: MHC class II binding epitope -continued

<400> SEQUENCE: 284

Arg Thr Val Ala Val Gly Ile Val Ala Ile Lys Gly Val
1 5 10

<210> SEQ ID NO 285
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 285

Val Ala Val Gly Ile Val Ala Ile Lys Gly Val Glu Ser
1 5 10

<210> SEQ ID NO 286
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 286

Val Gly Ile Val Ala Ile Lys Gly Val Glu Ser Glu Phe
1 5 10

<210> SEQ ID NO 287
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 287

Val Ala Ile Lys Gly Val Glu Ser Glu Phe Tyr Leu Ala
1 5 10

<210> SEQ ID NO 288
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 288

Lys Gly Val Glu Ser Glu Phe Tyr Leu Ala Met Asn Lys
1 5 10

<210> SEQ ID NO 289
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 289

Ser Glu Phe Tyr Leu Ala Met Asn Lys Glu Gly Lys Leu
1 5 10

<210> SEQ ID NO 290
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 290

Glu Phe Tyr Leu Ala Met Asn Lys Glu Gly Lys Leu Tyr
1 5 10

<210> SEQ ID NO 291
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 291

Phe Tyr Leu Ala Met Asn Lys Glu Gly Lys Leu Tyr Ala
1 5 10

<210> SEQ ID NO 292
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 292

Leu Ala Met Asn Lys Glu Gly Lys Leu Tyr Ala Lys Lys
1 5 10

<210> SEQ ID NO 293
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 293

Gly Lys Leu Tyr Ala Lys Lys Glu Cys Asn Glu Asp Cys
1 5 10

<210> SEQ ID NO 294
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 294

Lys Leu Tyr Ala Lys Lys Glu Cys Asn Glu Asp Cys Asn
1 5 10

<210> SEQ ID NO 295
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 295

Cys Asn Phe Lys Glu Leu Ile Leu Glu Asn His Tyr Asn
1 5 10

<210> SEQ ID NO 296
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 296

-continued

Lys Glu Leu Ile Leu Glu Asn His Tyr Asn Thr Tyr Ala
1 5 10

<210> SEQ ID NO 297
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 297

Glu Leu Ile Leu Glu Asn His Tyr Asn Thr Tyr Ala Ser
1 5 10

<210> SEQ ID NO 298
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 298

Leu Ile Leu Glu Asn His Tyr Asn Thr Tyr Ala Ser Ala
1 5 10

<210> SEQ ID NO 299
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 299

Asn His Tyr Asn Thr Tyr Ala Ser Ala Lys Trp Thr His
1 5 10

<210> SEQ ID NO 300
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 300

Asn Thr Tyr Ala Ser Ala Lys Trp Thr His Asn Gly Gly
1 5 10

<210> SEQ ID NO 301
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 301

Ala Lys Trp Thr His Asn Gly Gly Glu Met Phe Val Ala
1 5 10

<210> SEQ ID NO 302
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 302

-continued

Gly Glu Met Phe Val Ala Leu Asn Gln Lys Gly Ile Pro
1 5 10

<210> SEQ ID NO 303
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 303

Glu Met Phe Val Ala Leu Asn Gln Lys Gly Ile Pro Val
1 5 10

<210> SEQ ID NO 304
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 304

Phe Val Ala Leu Asn Gln Lys Gly Ile Pro Val Arg Gly
1 5 10

<210> SEQ ID NO 305
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 305

Val Ala Leu Asn Gln Lys Gly Ile Pro Val Arg Gly Lys
1 5 10

<210> SEQ ID NO 306
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 306

Lys Gly Ile Pro Val Arg Gly Lys Lys Thr Lys Lys Glu
1 5 10

<210> SEQ ID NO 307
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 307

Ile Pro Val Arg Gly Lys Lys Thr Lys Lys Glu Gln Lys
1 5 10

<210> SEQ ID NO 308
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 308

Lys Thr Lys Lys Glu Gln Lys Thr Ala His Phe Leu Pro
1 5 10

<210> SEQ ID NO 309
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 309

Asp Ser Val Cys Pro Gln Gly Lys Tyr Ile His Pro Gln
1 5 10

<210> SEQ ID NO 310
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 310

Lys Tyr Ile His Pro Gln Asn Asn Ser Ile Cys Cys Thr
1 5 10

<210> SEQ ID NO 311
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 311

Asn Ser Ile Cys Cys Thr Lys Cys His Lys Gly Thr Tyr
1 5 10

<210> SEQ ID NO 312
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 312

Thr Tyr Leu Tyr Asn Asp Cys Pro Gly Pro Gly Gln Asp
1 5 10

<210> SEQ ID NO 313
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 313

Tyr Leu Tyr Asn Asp Cys Pro Gly Pro Gly Gln Asp Thr
1 5 10

<210> SEQ ID NO 314
<211> LENGTH: 13
<212> TYPE: PRT
<213> ORGANISM: Artificial Sequence
<220> FEATURE:
<223> OTHER INFORMATION: MHC class II binding epitope -continued

<400> SEQUENCE: 314

Asn His Leu Arg His Cys Leu Ser Cys Ser Lys Cys Arg
1 5 10

<210> SEQ ID NO 315
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 315

His Cys Leu Ser Cys Ser Lys Cys Arg Lys Glu Met Gly
1 5 10

<210> SEQ ID NO 316
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 316

Lys Glu Met Gly Gln Val Glu Ile Ser Ser Cys Thr Val
1 5 10

<210> SEQ ID NO 317
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 317

Gly Gln Val Glu Ile Ser Ser Cys Thr Val Asp Arg Asp
1 5 10

<210> SEQ ID NO 318
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 318

Val Glu Ile Ser Ser Cys Thr Val Asp Arg Asp Thr Val
1 5 10

<210> SEQ ID NO 319
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 319

Cys Thr Val Asp Arg Asp Thr Val Cys Gly Cys Arg Lys
1 5 10

<210> SEQ ID NO 320
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 320

-continued

Asp Thr Val Cys Gly Cys Arg Lys Asn Gln Tyr Arg His
1 5 10

<210> SEQ ID NO 321
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 321

Asn Gln Tyr Arg His Tyr Trp Ser Glu Asn Leu Phe Gln
1 5 10

<210> SEQ ID NO 322
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 322

Arg His Tyr Trp Ser Glu Asn Leu Phe Gln Cys Phe Asn
1 5 10

<210> SEQ ID NO 323
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 323

His Tyr Trp Ser Glu Asn Leu Phe Gln Cys Phe Asn Cys
1 5 10

<210> SEQ ID NO 324
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 324

Glu Asn Leu Phe Gln Cys Phe Asn Cys Ser Leu Cys Leu
1 5 10

<210> SEQ ID NO 325
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 325

Asn Leu Phe Gln Cys Phe Asn Cys Ser Leu Cys Leu Asn
1 5 10

<210> SEQ ID NO 326
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 326

-continued

Gln Cys Phe Asn Cys Ser Leu Cys Leu Asn Gly Thr Val
1 5 10

<210> SEQ ID NO 327
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 327

Cys Ser Leu Cys Leu Asn Gly Thr Val His Leu Ser Cys
1 5 10

<210> SEQ ID NO 328
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 328

Leu Cys Leu Asn Gly Thr Val His Leu Ser Cys Gln Glu
1 5 10

<210> SEQ ID NO 329
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 329

Gly Thr Val His Leu Ser Cys Gln Glu Lys Gln Asn Thr
1 5 10

<210> SEQ ID NO 330
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 330

Val His Leu Ser Cys Gln Glu Lys Gln Asn Thr Val Cys
1 5 10

<210> SEQ ID NO 331
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 331

Glu Lys Gln Asn Thr Val Cys Thr Cys His Ala Gly Phe
1 5 10

<210> SEQ ID NO 332
<211> LENGTH: 13
<212> TYPE: PRT
<213> ORGANISM: Artificial Sequence
<220> FEATURE:
<223> OTHER INFORMATION: MHC class II binding epitope -continued

<400> SEQUENCE: 332

Asn Thr Val Cys Thr Cys His Ala Gly Phe Phe Leu Arg
 1               5                   10

<210> SEQ ID NO 333
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 333

Gly Phe Phe Leu Arg Glu Asn Glu Cys Val Ser Cys Ser
 1               5                   10

<210> SEQ ID NO 334
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 334

Phe Phe Leu Arg Glu Asn Glu Cys Val Ser Cys Ser Asn
 1               5                   10

<210> SEQ ID NO 335
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 335

Glu Cys Val Ser Cys Ser Asn Cys Lys Lys Ser Leu Glu
 1               5                   10

<210> SEQ ID NO 336
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 336

Lys Ser Leu Glu Cys Thr Lys Leu Cys Leu Pro Gln Ile
 1               5                   10

<210> SEQ ID NO 337
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 337

Thr Lys Leu Cys Leu Pro Gln Ile Glu Asn Val Lys Gly
 1               5                   10

<210> SEQ ID NO 338
<211> LENGTH: 13
<212> TYPE: PRT
<213> ORGANISM: Artificial Sequence
<220> FEATURE:
<223> OTHER INFORMATION: MHC class II binding epitope -continued

<400> SEQUENCE: 338

Leu Cys Leu Pro Gln Ile Glu Asn Val Lys Gly Thr Glu
1 5 10

<210> SEQ ID NO 339
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 339

Pro Gln Ile Glu Asn Val Lys Gly Thr Glu Asp Ser Gly
1 5 10

<210> SEQ ID NO 340
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 340

Ser Gly Thr Thr Val Leu Leu Pro Leu Val Ile Phe Phe
1 5 10

<210> SEQ ID NO 341
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 341

Thr Pro Tyr Ala Pro Glu Pro Gly Ser Thr Cys Arg Leu
1 5 10

<210> SEQ ID NO 342
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 342

Cys Arg Leu Arg Glu Tyr Tyr Asp Gln Thr Ala Gln Met
1 5 10

<210> SEQ ID NO 343
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 343

Arg Glu Tyr Tyr Asp Gln Thr Ala Gln Met Cys Cys Ser
1 5 10

<210> SEQ ID NO 344
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 344

-continued

Glu Tyr Tyr Asp Gln Thr Ala Gln Met Cys Cys Ser Lys
1 5 10

<210> SEQ ID NO 345
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 345

Ala Gln Met Cys Cys Ser Lys Cys Ser Pro Gly Gln His
1 5 10

<210> SEQ ID NO 346
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 346

Lys Cys Ser Pro Gly Gln His Ala Lys Val Phe Cys Thr
1 5 10

<210> SEQ ID NO 347
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 347

Ala Lys Val Phe Cys Thr Lys Thr Ser Asp Thr Val Cys
1 5 10

<210> SEQ ID NO 348
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 348

Lys Val Phe Cys Thr Lys Thr Ser Asp Thr Val Cys Asp
1 5 10

<210> SEQ ID NO 349
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 349

Ser Thr Tyr Thr Gln Leu Trp Asn Trp Val Pro Glu Cys
1 5 10

<210> SEQ ID NO 350
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 350

-continued

Thr Gln Leu Trp Asn Trp Val Pro Glu Cys Leu Ser Cys
1 5 10

<210> SEQ ID NO 351
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 351

Gln Leu Trp Asn Trp Val Pro Glu Cys Leu Ser Cys Gly
1 5 10

<210> SEQ ID NO 352
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 352

Asn Trp Val Pro Glu Cys Leu Ser Cys Gly Ser Arg Cys
1 5 10

<210> SEQ ID NO 353
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 353

Glu Cys Leu Ser Cys Gly Ser Arg Cys Ser Ser Asp Gln
1 5 10

<210> SEQ ID NO 354
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 354

Ser Arg Cys Ser Ser Asp Gln Glu Val Thr Gln Ala Cys
1 5 10

<210> SEQ ID NO 355
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 355

Gln Glu Val Thr Gln Ala Cys Thr Arg Glu Gln Asn Arg
1 5 10

<210> SEQ ID NO 356
<211> LENGTH: 13
<212> TYPE: PRT
<213> ORGANISM: Artificial Sequence
<220> FEATURE:
<223> OTHER INFORMATION: MHC class II binding epitope -continued

<400> SEQUENCE: 356

Gln Asn Arg Ile Cys Thr Cys Arg Pro Gly Trp Tyr Cys
1 5 10

<210> SEQ ID NO 357
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 357

Asn Arg Ile Cys Thr Cys Arg Pro Gly Trp Tyr Cys Ala
1 5 10

<210> SEQ ID NO 358
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 358

Pro Gly Trp Tyr Cys Ala Leu Ser Lys Gln Glu Gly Cys
1 5 10

<210> SEQ ID NO 359
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 359

Gly Trp Tyr Cys Ala Leu Ser Lys Gln Glu Gly Cys Arg
1 5 10

<210> SEQ ID NO 360
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 360

Cys Ala Leu Ser Lys Gln Glu Gly Cys Arg Leu Cys Ala
1 5 10

<210> SEQ ID NO 361
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 361

Ala Pro Leu Arg Lys Cys Arg Pro Gly Phe Gly Val Ala
1 5 10

<210> SEQ ID NO 362
<211> LENGTH: 13
<212> TYPE: PRT
<213> ORGANISM: Artificial Sequence
<220> FEATURE:
<223> OTHER INFORMATION: MHC class II binding epitope -continued

<400> SEQUENCE: 362

Pro Gly Phe Gly Val Ala Arg Pro Gly Thr Glu Thr Ser
1 5 10

<210> SEQ ID NO 363
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 363

Phe Gly Val Ala Arg Pro Gly Thr Glu Thr Ser Asp Val
1 5 10

<210> SEQ ID NO 364
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 364

Ser Asp Val Val Cys Lys Pro Cys Ala Pro Gly Thr Phe
1 5 10

<210> SEQ ID NO 365
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 365

Gly Thr Phe Ser Asn Thr Thr Ser Ser Thr Asp Ile Cys
1 5 10

<210> SEQ ID NO 366
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 366

Thr Asp Ile Cys Arg Pro His Gln Ile Cys Asn Val Val
1 5 10

<210> SEQ ID NO 367
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 367

His Gln Ile Cys Asn Val Val Ala Ile Pro Gly Asn Ala
1 5 10

<210> SEQ ID NO 368
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 368

-continued

Ile Cys Asn Val Val Ala Ile Pro Gly Asn Ala Ser Arg
1 5 10

<210> SEQ ID NO 369
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 369

Cys Asn Val Val Ala Ile Pro Gly Asn Ala Ser Arg Asp
1 5 10

<210> SEQ ID NO 370
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 370

Asn Val Val Ala Ile Pro Gly Asn Ala Ser Arg Asp Ala
1 5 10

<210> SEQ ID NO 371
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 371

Val Ala Ile Pro Gly Asn Ala Ser Arg Asp Ala Val Cys
1 5 10

<210> SEQ ID NO 372
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 372

Asp Ala Val Cys Thr Ser Thr Thr Thr Pro Thr Arg Ser
1 5 10

<210> SEQ ID NO 373
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 373

Thr Arg Ser Met Ala Pro Gly Ala Val His Leu Pro Gln
1 5 10

<210> SEQ ID NO 374
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 374

-continued

Arg Ser Met Ala Pro Gly Ala Val His Leu Pro Gln Pro
1 5 10

<210> SEQ ID NO 375
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 375

Val His Leu Pro Gln Pro Val Ser Thr Arg Ser Gln His
1 5 10

<210> SEQ ID NO 376
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 376

Gln Pro Val Ser Thr Arg Ser Gln His Thr Gln Pro Thr
1 5 10

<210> SEQ ID NO 377
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 377

Pro Glu Pro Ser Thr Ala Pro Ser Thr Ser Phe Leu Leu
1 5 10

<210> SEQ ID NO 378
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 378

Ser Phe Leu Leu Pro Met Gly Pro Ser Pro Pro Ala Glu
1 5 10

<210> SEQ ID NO 379
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 379

Phe Leu Leu Pro Met Gly Pro Ser Pro Pro Ala Glu Gly
1 5 10

<210> SEQ ID NO 380
<211> LENGTH: 13
<212> TYPE: PRT
<213> ORGANISM: Artificial Sequence
<220> FEATURE:
<223> OTHER INFORMATION: MHC class II binding epitope -continued

<400> SEQUENCE: 380

Thr Pro Tyr Ala Pro Glu Pro Gly Ser Thr Cys Arg Leu
1 5 10

<210> SEQ ID NO 381
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 381

Cys Arg Leu Arg Glu Tyr Tyr Asp Gln Thr Ala Gln Met
1 5 10

<210> SEQ ID NO 382
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 382

Arg Glu Tyr Tyr Asp Gln Thr Ala Gln Met Cys Cys Ser
1 5 10

<210> SEQ ID NO 383
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 383

Glu Tyr Tyr Asp Gln Thr Ala Gln Met Cys Cys Ser Lys
1 5 10

<210> SEQ ID NO 384
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 384

Ala Gln Met Cys Cys Ser Lys Cys Ser Pro Gly Gln His
1 5 10

<210> SEQ ID NO 385
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 385

Lys Cys Ser Pro Gly Gln His Ala Lys Val Phe Cys Thr
1 5 10

<210> SEQ ID NO 386
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 386

Ala Lys Val Phe Cys Thr Lys Thr Ser Asp Thr Val Cys
1 5 10

<210> SEQ ID NO 387
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 387

Lys Val Phe Cys Thr Lys Thr Ser Asp Thr Val Cys Asp
1 5 10

<210> SEQ ID NO 388
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 388

Ser Thr Tyr Thr Gln Leu Trp Asn Trp Val Pro Glu Cys
1 5 10

<210> SEQ ID NO 389
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 389

Thr Gln Leu Trp Asn Trp Val Pro Glu Cys Leu Ser Cys
1 5 10

<210> SEQ ID NO 390
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 390

Gln Leu Trp Asn Trp Val Pro Glu Cys Leu Ser Cys Gly
1 5 10

<210> SEQ ID NO 391
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 391

Asn Trp Val Pro Glu Cys Leu Ser Cys Gly Ser Arg Cys
1 5 10

<210> SEQ ID NO 392
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 392

-continued

Glu Cys Leu Ser Cys Gly Ser Arg Cys Ser Ser Asp Gln
 1               5                   10

<210> SEQ ID NO 393
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 393

Ser Arg Cys Ser Ser Asp Gln Glu Val Thr Gln Ala Cys
 1               5                   10

<210> SEQ ID NO 394
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 394

Gln Glu Val Thr Gln Ala Cys Thr Arg Glu Gln Asn Arg
 1               5                   10

<210> SEQ ID NO 395
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 395

Gln Asn Arg Ile Cys Thr Cys Arg Pro Gly Trp Tyr Cys
 1               5                   10

<210> SEQ ID NO 396
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 396

Asn Arg Ile Cys Thr Cys Arg Pro Gly Trp Tyr Cys Ala
 1               5                   10

<210> SEQ ID NO 397
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 397

Pro Gly Trp Tyr Cys Ala Leu Ser Lys Gln Glu Gly Cys
 1               5                   10

<210> SEQ ID NO 398
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 398

-continued

Gly Trp Tyr Cys Ala Leu Ser Lys Gln Glu Gly Cys Arg
1 5 10

<210> SEQ ID NO 399
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 399

Cys Ala Leu Ser Lys Gln Glu Gly Cys Arg Leu Cys Ala
1 5 10

<210> SEQ ID NO 400
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 400

Ala Pro Leu Arg Lys Cys Arg Pro Gly Phe Gly Val Ala
1 5 10

<210> SEQ ID NO 401
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 401

Pro Gly Phe Gly Val Ala Arg Pro Gly Thr Glu Thr Ser
1 5 10

<210> SEQ ID NO 402
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 402

Phe Gly Val Ala Arg Pro Gly Thr Glu Thr Ser Asp Val
1 5 10

<210> SEQ ID NO 403
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 403

Ser Asp Val Val Cys Lys Pro Cys Ala Pro Gly Thr Phe
1 5 10

<210> SEQ ID NO 404
<211> LENGTH: 13
<212> TYPE: PRT
<213> ORGANISM: Artificial Sequence
<220> FEATURE:
<223> OTHER INFORMATION: MHC class II binding epitope -continued

<400> SEQUENCE: 404

Gly Thr Phe Ser Asn Thr Thr Ser Ser Thr Asp Ile Cys
1 5 10

<210> SEQ ID NO 405
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 405

Thr Asp Ile Cys Arg Pro His Gln Ile Cys Asn Val Val
1 5 10

<210> SEQ ID NO 406
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 406

His Gln Ile Cys Asn Val Val Ala Ile Pro Gly Asn Ala
1 5 10

<210> SEQ ID NO 407
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 407

Ile Cys Asn Val Val Ala Ile Pro Gly Asn Ala Ser Arg
1 5 10

<210> SEQ ID NO 408
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 408

Cys Asn Val Val Ala Ile Pro Gly Asn Ala Ser Arg Asp
1 5 10

<210> SEQ ID NO 409
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 409

Asn Val Val Ala Ile Pro Gly Asn Ala Ser Arg Asp Ala
1 5 10

<210> SEQ ID NO 410
<211> LENGTH: 13
<212> TYPE: PRT
<213> ORGANISM: Artificial Sequence
<220> FEATURE:
<223> OTHER INFORMATION: MHC class II binding epitope -continued

<400> SEQUENCE: 410

Val Ala Ile Pro Gly Asn Ala Ser Arg Asp Ala Val Cys
1 5 10

<210> SEQ ID NO 411
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 411

Asp Ala Val Cys Thr Ser Thr Thr Thr Pro Thr Arg Ser
1 5 10

<210> SEQ ID NO 412
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 412

Thr Arg Ser Met Ala Pro Gly Ala Val His Leu Pro Gln
1 5 10

<210> SEQ ID NO 413
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 413

Arg Ser Met Ala Pro Gly Ala Val His Leu Pro Gln Pro
1 5 10

<210> SEQ ID NO 414
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 414

Val His Leu Pro Gln Pro Val Ser Thr Arg Ser Gln His
1 5 10

<210> SEQ ID NO 415
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 415

Gln Pro Val Ser Thr Arg Ser Gln His Thr Gln Pro Thr
1 5 10

<210> SEQ ID NO 416
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 416

-continued

Pro Glu Pro Ser Thr Ala Pro Ser Thr Ser Phe Leu Leu
1 5 10

<210> SEQ ID NO 417
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 417

Ser Phe Leu Leu Pro Met Gly Pro Ser Pro Pro Ala Glu
1 5 10

<210> SEQ ID NO 418
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 418

Phe Leu Leu Pro Met Gly Pro Ser Pro Pro Ala Glu Gly
1 5 10

<210> SEQ ID NO 419
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 419

Pro Cys Ile Pro Lys Ser Phe Gly Tyr Ser Ser Val Val
1 5 10

<210> SEQ ID NO 420
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 420

Lys Ser Phe Gly Tyr Ser Ser Val Val Cys Val Cys Asn
1 5 10

<210> SEQ ID NO 421
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 421

Phe Gly Tyr Ser Ser Val Val Cys Val Cys Asn Ala Thr
1 5 10

<210> SEQ ID NO 422
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 422

-continued

Ser Ser Val Val Cys Val Cys Asn Ala Thr Tyr Cys Asp
1 5 10

<210> SEQ ID NO 423
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 423

Ser Val Val Cys Val Cys Asn Ala Thr Tyr Cys Asp Ser
1 5 10

<210> SEQ ID NO 424
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 424

Val Cys Val Cys Asn Ala Thr Tyr Cys Asp Ser Phe Asp
1 5 10

<210> SEQ ID NO 425
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 425

Ala Thr Tyr Cys Asp Ser Phe Asp Pro Pro Thr Phe Pro
1 5 10

<210> SEQ ID NO 426
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 426

Asp Ser Phe Asp Pro Pro Thr Phe Pro Ala Leu Gly Thr
1 5 10

<210> SEQ ID NO 427
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 427

Pro Thr Phe Pro Ala Leu Gly Thr Phe Ser Arg Tyr Glu
1 5 10

<210> SEQ ID NO 428
<211> LENGTH: 13
<212> TYPE: PRT
<213> ORGANISM: Artificial Sequence
<220> FEATURE:
<223> OTHER INFORMATION: MHC class II binding epitope -continued

<400> SEQUENCE: 428

Pro Ala Leu Gly Thr Phe Ser Arg Tyr Glu Ser Thr Arg
1 5 10

<210> SEQ ID NO 429
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 429

Gly Thr Phe Ser Arg Tyr Glu Ser Thr Arg Ser Gly Arg
1 5 10

<210> SEQ ID NO 430
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 430

Ser Arg Tyr Glu Ser Thr Arg Ser Gly Arg Arg Met Glu
1 5 10

<210> SEQ ID NO 431
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 431

Gly Arg Arg Met Glu Leu Ser Met Gly Pro Ile Gln Ala
1 5 10

<210> SEQ ID NO 432
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 432

Arg Arg Met Glu Leu Ser Met Gly Pro Ile Gln Ala Asn
1 5 10

<210> SEQ ID NO 433
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 433

Arg Met Glu Leu Ser Met Gly Pro Ile Gln Ala Asn His
1 5 10

<210> SEQ ID NO 434
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 434

Met Glu Leu Ser Met Gly Pro Ile Gln Ala Asn His Thr
1 5 10

<210> SEQ ID NO 435
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 435

Leu Ser Met Gly Pro Ile Gln Ala Asn His Thr Gly Thr
1 5 10

<210> SEQ ID NO 436
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 436

Met Gly Pro Ile Gln Ala Asn His Thr Gly Thr Gly Leu
1 5 10

<210> SEQ ID NO 437
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 437

Gly Pro Ile Gln Ala Asn His Thr Gly Thr Gly Leu Leu
1 5 10

<210> SEQ ID NO 438
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 438

Thr Gly Leu Leu Leu Thr Leu Gln Pro Glu Gln Lys Phe
1 5 10

<210> SEQ ID NO 439
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 439

Gly Leu Leu Leu Thr Leu Gln Pro Glu Gln Lys Phe Gln
1 5 10

<210> SEQ ID NO 440
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 440

-continued

Leu Leu Leu Thr Leu Gln Pro Glu Gln Lys Phe Gln Lys
1 5 10

<210> SEQ ID NO 441
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 441

Leu Thr Leu Gln Pro Glu Gln Lys Phe Gln Lys Val Lys
1 5 10

<210> SEQ ID NO 442
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 442

Thr Leu Gln Pro Glu Gln Lys Phe Gln Lys Val Lys Gly
1 5 10

<210> SEQ ID NO 443
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 443

Pro Glu Gln Lys Phe Gln Lys Val Lys Gly Phe Gly Gly
1 5 10

<210> SEQ ID NO 444
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 444

Gln Lys Phe Gln Lys Val Lys Gly Phe Gly Gly Ala Met
1 5 10

<210> SEQ ID NO 445
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 445

Gln Lys Val Lys Gly Phe Gly Gly Ala Met Thr Asp Ala
1 5 10

<210> SEQ ID NO 446
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 446

-continued

```
Lys Gly Phe Gly Gly Ala Met Thr Asp Ala Ala Ala Leu
 1               5                   10


<210> SEQ ID NO 447
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 447

Gly Phe Gly Gly Ala Met Thr Asp Ala Ala Ala Leu Asn
 1               5                   10


<210> SEQ ID NO 448
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 448

Gly Ala Met Thr Asp Ala Ala Ala Leu Asn Ile Leu Ala
 1               5                   10


<210> SEQ ID NO 449
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 449

Ala Met Thr Asp Ala Ala Ala Leu Asn Ile Leu Ala Leu
 1               5                   10


<210> SEQ ID NO 450
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 450

Met Thr Asp Ala Ala Ala Leu Asn Ile Leu Ala Leu Ser
 1               5                   10


<210> SEQ ID NO 451
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 451

Ala Ala Leu Asn Ile Leu Ala Leu Ser Pro Pro Ala Gln
 1               5                   10


<210> SEQ ID NO 452
<211> LENGTH: 13
<212> TYPE: PRT
<213> ORGANISM: Artificial Sequence
<220> FEATURE:
<223> OTHER INFORMATION: MHC class II binding epitope
```

-continued

<400> SEQUENCE: 452

Ala Leu Asn Ile Leu Ala Leu Ser Pro Pro Ala Gln Asn
1 5 10

<210> SEQ ID NO 453
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 453

Leu Asn Ile Leu Ala Leu Ser Pro Pro Ala Gln Asn Leu
1 5 10

<210> SEQ ID NO 454
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 454

Asn Ile Leu Ala Leu Ser Pro Pro Ala Gln Asn Leu Leu
1 5 10

<210> SEQ ID NO 455
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 455

Leu Ala Leu Ser Pro Pro Ala Gln Asn Leu Leu Leu Lys
1 5 10

<210> SEQ ID NO 456
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 456

Ala Leu Ser Pro Pro Ala Gln Asn Leu Leu Leu Lys Ser
1 5 10

<210> SEQ ID NO 457
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 457

Pro Ala Gln Asn Leu Leu Leu Lys Ser Tyr Phe Ser Glu
1 5 10

<210> SEQ ID NO 458
<211> LENGTH: 13
<212> TYPE: PRT
<213> ORGANISM: Artificial Sequence
<220> FEATURE:
<223> OTHER INFORMATION: MHC class II binding epitope -continued

<400> SEQUENCE: 458

Ala Gln Asn Leu Leu Leu Lys Ser Tyr Phe Ser Glu Glu
1 5 10

<210> SEQ ID NO 459
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 459

Gln Asn Leu Leu Leu Lys Ser Tyr Phe Ser Glu Glu Gly
1 5 10

<210> SEQ ID NO 460
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 460

Asn Leu Leu Leu Lys Ser Tyr Phe Ser Glu Glu Gly Ile
1 5 10

<210> SEQ ID NO 461
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 461

Leu Leu Leu Lys Ser Tyr Phe Ser Glu Glu Gly Ile Gly
1 5 10

<210> SEQ ID NO 462
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 462

Lys Ser Tyr Phe Ser Glu Glu Gly Ile Gly Tyr Asn Ile
1 5 10

<210> SEQ ID NO 463
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 463

Ser Tyr Phe Ser Glu Glu Gly Ile Gly Tyr Asn Ile Ile
1 5 10

<210> SEQ ID NO 464
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 464

-continued

Phe Ser Glu Glu Gly Ile Gly Tyr Asn Ile Ile Arg Val
 1               5                   10

<210> SEQ ID NO 465
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 465

Glu Gly Ile Gly Tyr Asn Ile Ile Arg Val Pro Met Ala
 1               5                   10

<210> SEQ ID NO 466
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 466

Gly Ile Gly Tyr Asn Ile Ile Arg Val Pro Met Ala Ser
 1               5                   10

<210> SEQ ID NO 467
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 467

Ile Gly Tyr Asn Ile Ile Arg Val Pro Met Ala Ser Cys
 1               5                   10

<210> SEQ ID NO 468
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 468

Tyr Asn Ile Ile Arg Val Pro Met Ala Ser Cys Asp Phe
 1               5                   10

<210> SEQ ID NO 469
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 469

Asn Ile Ile Arg Val Pro Met Ala Ser Cys Asp Phe Ser
 1               5                   10

<210> SEQ ID NO 470
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 470

-continued

Ile Ile Arg Val Pro Met Ala Ser Cys Asp Phe Ser Ile
1 5 10

<210> SEQ ID NO 471
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 471

Ile Arg Val Pro Met Ala Ser Cys Asp Phe Ser Ile Arg
1 5 10

<210> SEQ ID NO 472
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 472

Val Pro Met Ala Ser Cys Asp Phe Ser Ile Arg Thr Tyr
1 5 10

<210> SEQ ID NO 473
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 473

Pro Met Ala Ser Cys Asp Phe Ser Ile Arg Thr Tyr Thr
1 5 10

<210> SEQ ID NO 474
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 474

Ser Cys Asp Phe Ser Ile Arg Thr Tyr Thr Tyr Ala Asp
1 5 10

<210> SEQ ID NO 475
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 475

Cys Asp Phe Ser Ile Arg Thr Tyr Thr Tyr Ala Asp Thr
1 5 10

<210> SEQ ID NO 476
<211> LENGTH: 13
<212> TYPE: PRT
<213> ORGANISM: Artificial Sequence
<220> FEATURE:
<223> OTHER INFORMATION: MHC class II binding epitope -continued

<400> SEQUENCE: 476

Phe Ser Ile Arg Thr Tyr Thr Tyr Ala Asp Thr Pro Asp
1 5 10

<210> SEQ ID NO 477
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 477

Arg Thr Tyr Thr Tyr Ala Asp Thr Pro Asp Asp Phe Gln
1 5 10

<210> SEQ ID NO 478
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 478

Thr Tyr Thr Tyr Ala Asp Thr Pro Asp Asp Phe Gln Leu
1 5 10

<210> SEQ ID NO 479
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 479

Tyr Thr Tyr Ala Asp Thr Pro Asp Asp Phe Gln Leu His
1 5 10

<210> SEQ ID NO 480
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 480

Ala Asp Thr Pro Asp Asp Phe Gln Leu His Asn Phe Ser
1 5 10

<210> SEQ ID NO 481
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 481

Pro Asp Asp Phe Gln Leu His Asn Phe Ser Leu Pro Glu
1 5 10

<210> SEQ ID NO 482
<211> LENGTH: 13
<212> TYPE: PRT
<213> ORGANISM: Artificial Sequence
<220> FEATURE:
<223> OTHER INFORMATION: MHC class II binding epitope -continued

<400> SEQUENCE: 482

Asp Asp Phe Gln Leu His Asn Phe Ser Leu Pro Glu Glu
1 5 10

<210> SEQ ID NO 483
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 483

Phe Gln Leu His Asn Phe Ser Leu Pro Glu Glu Asp Thr
1 5 10

<210> SEQ ID NO 484
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 484

His Asn Phe Ser Leu Pro Glu Glu Asp Thr Lys Leu Lys
1 5 10

<210> SEQ ID NO 485
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 485

Phe Ser Leu Pro Glu Glu Asp Thr Lys Leu Lys Ile Pro
1 5 10

<210> SEQ ID NO 486
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 486

Ser Leu Pro Glu Glu Asp Thr Lys Leu Lys Ile Pro Leu
1 5 10

<210> SEQ ID NO 487
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 487

Glu Glu Asp Thr Lys Leu Lys Ile Pro Leu Ile His Arg
1 5 10

<210> SEQ ID NO 488
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 488

-continued

Thr Lys Leu Lys Ile Pro Leu Ile His Arg Ala Leu Gln
1 5 10

<210> SEQ ID NO 489
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 489

Lys Leu Lys Ile Pro Leu Ile His Arg Ala Leu Gln Leu
1 5 10

<210> SEQ ID NO 490
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 490

Leu Lys Ile Pro Leu Ile His Arg Ala Leu Gln Leu Ala
1 5 10

<210> SEQ ID NO 491
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 491

Ile Pro Leu Ile His Arg Ala Leu Gln Leu Ala Gln Arg
1 5 10

<210> SEQ ID NO 492
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 492

Pro Leu Ile His Arg Ala Leu Gln Leu Ala Gln Arg Pro
1 5 10

<210> SEQ ID NO 493
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 493

His Arg Ala Leu Gln Leu Ala Gln Arg Pro Val Ser Leu
1 5 10

<210> SEQ ID NO 494
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 494

-continued

```
Arg Ala Leu Gln Leu Ala Gln Arg Pro Val Ser Leu Leu
 1               5                  10


<210> SEQ ID NO 495
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 495

Ala Leu Gln Leu Ala Gln Arg Pro Val Ser Leu Leu Ala
 1               5                  10


<210> SEQ ID NO 496
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 496

Leu Gln Leu Ala Gln Arg Pro Val Ser Leu Leu Ala Ser
 1               5                  10


<210> SEQ ID NO 497
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 497

Arg Pro Val Ser Leu Leu Ala Ser Pro Trp Thr Ser Pro
 1               5                  10


<210> SEQ ID NO 498
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 498

Pro Val Ser Leu Leu Ala Ser Pro Trp Thr Ser Pro Thr
 1               5                  10


<210> SEQ ID NO 499
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 499

Val Ser Leu Leu Ala Ser Pro Trp Thr Ser Pro Thr Trp
 1               5                  10


<210> SEQ ID NO 500
<211> LENGTH: 13
<212> TYPE: PRT
```

-continued

<213> ORGANISM: Artificial Sequence
<220> FEATURE:
<223> OTHER INFORMATION: MHC class II binding epitope

<400> SEQUENCE: 500

Ser Leu Leu Ala Ser Pro Trp Thr Ser Pro Thr Trp Leu
1 5 10

<210> SEQ ID NO 501
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 501

Ser Pro Trp Thr Ser Pro Thr Trp Leu Lys Thr Asn Gly
1 5 10

<210> SEQ ID NO 502
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 502

Thr Ser Pro Thr Trp Leu Lys Thr Asn Gly Ala Val Asn
1 5 10

<210> SEQ ID NO 503
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 503

Pro Thr Trp Leu Lys Thr Asn Gly Ala Val Asn Gly Lys
1 5 10

<210> SEQ ID NO 504
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 504

Thr Trp Leu Lys Thr Asn Gly Ala Val Asn Gly Lys Gly
1 5 10

<210> SEQ ID NO 505
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 505

Gly Ala Val Asn Gly Lys Gly Ser Leu Lys Gly Gln Pro
1 5 10

<210> SEQ ID NO 506
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 506

Gly Ser Leu Lys Gly Gln Pro Gly Asp Ile Tyr His Gln
1 5 10

<210> SEQ ID NO 507
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 507

Gly Asp Ile Tyr His Gln Thr Trp Ala Arg Tyr Phe Val
1 5 10

<210> SEQ ID NO 508
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 508

Asp Ile Tyr His Gln Thr Trp Ala Arg Tyr Phe Val Lys
1 5 10

<210> SEQ ID NO 509
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 509

Gln Thr Trp Ala Arg Tyr Phe Val Lys Phe Leu Asp Ala
1 5 10

<210> SEQ ID NO 510
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 510

Trp Ala Arg Tyr Phe Val Lys Phe Leu Asp Ala Tyr Ala
1 5 10

<210> SEQ ID NO 511
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 511

Ala Arg Tyr Phe Val Lys Phe Leu Asp Ala Tyr Ala Glu
1 5 10

<210> SEQ ID NO 512
<211> LENGTH: 13
<212> TYPE: PRT
<213> ORGANISM: Artificial Sequence
<220> FEATURE:

-continued

<223> OTHER INFORMATION: MHC class II binding epitope

<400> SEQUENCE: 512

Arg Tyr Phe Val Lys Phe Leu Asp Ala Tyr Ala Glu His
1 5 10

<210> SEQ ID NO 513
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 513

Tyr Phe Val Lys Phe Leu Asp Ala Tyr Ala Glu His Lys
1 5 10

<210> SEQ ID NO 514
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 514

Phe Val Lys Phe Leu Asp Ala Tyr Ala Glu His Lys Leu
1 5 10

<210> SEQ ID NO 515
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 515

Val Lys Phe Leu Asp Ala Tyr Ala Glu His Lys Leu Gln
1 5 10

<210> SEQ ID NO 516
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 516

Lys Phe Leu Asp Ala Tyr Ala Glu His Lys Leu Gln Phe
1 5 10

<210> SEQ ID NO 517
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 517

Asp Ala Tyr Ala Glu His Lys Leu Gln Phe Trp Ala Val
1 5 10

<210> SEQ ID NO 518
<211> LENGTH: 13
<212> TYPE: PRT
<213> ORGANISM: Artificial Sequence
<220> FEATURE:
<223> OTHER INFORMATION: MHC class II binding epitope -continued

<400> SEQUENCE: 518

Tyr Ala Glu His Lys Leu Gln Phe Trp Ala Val Thr Ala
1 5 10

<210> SEQ ID NO 519
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 519

His Lys Leu Gln Phe Trp Ala Val Thr Ala Glu Asn Glu
1 5 10

<210> SEQ ID NO 520
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 520

Leu Gln Phe Trp Ala Val Thr Ala Glu Asn Glu Pro Ser
1 5 10

<210> SEQ ID NO 521
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 521

Gln Phe Trp Ala Val Thr Ala Glu Asn Glu Pro Ser Ala
1 5 10

<210> SEQ ID NO 522
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 522

Phe Trp Ala Val Thr Ala Glu Asn Glu Pro Ser Ala Gly
1 5 10

<210> SEQ ID NO 523
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 523

Trp Ala Val Thr Ala Glu Asn Glu Pro Ser Ala Gly Leu
1 5 10

<210> SEQ ID NO 524
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 524

Val Thr Ala Glu Asn Glu Pro Ser Ala Gly Leu Leu Ser
1 5 10

<210> SEQ ID NO 525
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 525

Pro Ser Ala Gly Leu Leu Ser Gly Tyr Pro Phe Gln Cys
1 5 10

<210> SEQ ID NO 526
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 526

Ala Gly Leu Leu Ser Gly Tyr Pro Phe Gln Cys Leu Gly
1 5 10

<210> SEQ ID NO 527
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 527

Gly Leu Leu Ser Gly Tyr Pro Phe Gln Cys Leu Gly Phe
1 5 10

<210> SEQ ID NO 528
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 528

Ser Gly Tyr Pro Phe Gln Cys Leu Gly Phe Thr Pro Glu
1 5 10

<210> SEQ ID NO 529
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 529

Tyr Pro Phe Gln Cys Leu Gly Phe Thr Pro Glu His Gln
1 5 10

<210> SEQ ID NO 530
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 530

-continued

Gln Cys Leu Gly Phe Thr Pro Glu His Gln Arg Asp Phe
1 5 10

<210> SEQ ID NO 531
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 531

Leu Gly Phe Thr Pro Glu His Gln Arg Asp Phe Ile Ala
1 5 10

<210> SEQ ID NO 532
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 532

Phe Thr Pro Glu His Gln Arg Asp Phe Ile Ala Arg Asp
1 5 10

<210> SEQ ID NO 533
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 533

Arg Asp Phe Ile Ala Arg Asp Leu Gly Pro Thr Leu Ala
1 5 10

<210> SEQ ID NO 534
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 534

Asp Phe Ile Ala Arg Asp Leu Gly Pro Thr Leu Ala Asn
1 5 10

<210> SEQ ID NO 535
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 535

Arg Asp Leu Gly Pro Thr Leu Ala Asn Ser Thr His His
1 5 10

<210> SEQ ID NO 536
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 536

-continued

Leu Gly Pro Thr Leu Ala Asn Ser Thr His His Asn Val
1 5 10

<210> SEQ ID NO 537
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 537

Pro Thr Leu Ala Asn Ser Thr His His Asn Val Arg Leu
1 5 10

<210> SEQ ID NO 538
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 538

His Asn Val Arg Leu Leu Met Leu Asp Asp Gln Arg Leu
1 5 10

<210> SEQ ID NO 539
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 539

Val Arg Leu Leu Met Leu Asp Asp Gln Arg Leu Leu Leu
1 5 10

<210> SEQ ID NO 540
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 540

Arg Leu Leu Met Leu Asp Asp Gln Arg Leu Leu Leu Pro
1 5 10

<210> SEQ ID NO 541
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 541

Leu Leu Met Leu Asp Asp Gln Arg Leu Leu Leu Pro His
1 5 10

<210> SEQ ID NO 542
<211> LENGTH: 13
<212> TYPE: PRT

-continued

<213> ORGANISM: Artificial Sequence
<220> FEATURE:
<223> OTHER INFORMATION: MHC class II binding epitope

<400> SEQUENCE: 542

Leu Met Leu Asp Asp Gln Arg Leu Leu Leu Pro His Trp
1 5 10

<210> SEQ ID NO 543
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 543

Asp Asp Gln Arg Leu Leu Leu Pro His Trp Ala Lys Val
1 5 10

<210> SEQ ID NO 544
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 544

Asp Gln Arg Leu Leu Leu Pro His Trp Ala Lys Val Val
1 5 10

<210> SEQ ID NO 545
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 545

Gln Arg Leu Leu Leu Pro His Trp Ala Lys Val Val Leu
1 5 10

<210> SEQ ID NO 546
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 546

Arg Leu Leu Leu Pro His Trp Ala Lys Val Val Leu Thr
1 5 10

<210> SEQ ID NO 547
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 547

Leu Leu Leu Pro His Trp Ala Lys Val Val Leu Thr Asp
1 5 10

<210> SEQ ID NO 548
<211> LENGTH: 13
<212> TYPE: PRT
<213> ORGANISM: Artificial Sequence -continued
<220> FEATURE:
<223> OTHER INFORMATION: MHC class II binding epitope

<400> SEQUENCE: 548

Pro His Trp Ala Lys Val Val Leu Thr Asp Pro Glu Ala
1 5 10

<210> SEQ ID NO 549
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 549

Trp Ala Lys Val Val Leu Thr Asp Pro Glu Ala Ala Lys
1 5 10

<210> SEQ ID NO 550
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 550

Ala Lys Val Val Leu Thr Asp Pro Glu Ala Ala Lys Tyr
1 5 10

<210> SEQ ID NO 551
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 551

Lys Val Val Leu Thr Asp Pro Glu Ala Ala Lys Tyr Val
1 5 10

<210> SEQ ID NO 552
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 552

Val Val Leu Thr Asp Pro Glu Ala Ala Lys Tyr Val His
1 5 10

<210> SEQ ID NO 553
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 553

Glu Ala Ala Lys Tyr Val His Gly Ile Ala Val His Trp
1 5 10

<210> SEQ ID NO 554
<211> LENGTH: 13
<212> TYPE: PRT
<213> ORGANISM: Artificial Sequence
<220> FEATURE:

<223> OTHER INFORMATION: MHC class II binding epitope

<400> SEQUENCE: 554

Ala Lys Tyr Val His Gly Ile Ala Val His Trp Tyr Leu
1 5 10

<210> SEQ ID NO 555
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 555

Lys Tyr Val His Gly Ile Ala Val His Trp Tyr Leu Asp
1 5 10

<210> SEQ ID NO 556
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 556

Tyr Val His Gly Ile Ala Val His Trp Tyr Leu Asp Phe
1 5 10

<210> SEQ ID NO 557
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 557

His Gly Ile Ala Val His Trp Tyr Leu Asp Phe Leu Ala
1 5 10

<210> SEQ ID NO 558
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 558

Ile Ala Val His Trp Tyr Leu Asp Phe Leu Ala Pro Ala
1 5 10

<210> SEQ ID NO 559
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 559

Val His Trp Tyr Leu Asp Phe Leu Ala Pro Ala Lys Ala
1 5 10

<210> SEQ ID NO 560
<211> LENGTH: 13
<212> TYPE: PRT
<213> ORGANISM: Artificial Sequence
<220> FEATURE:
<223> OTHER INFORMATION: MHC class II binding epitope -continued

<400> SEQUENCE: 560

His Trp Tyr Leu Asp Phe Leu Ala Pro Ala Lys Ala Thr
1 5 10

<210> SEQ ID NO 561
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 561

Trp Tyr Leu Asp Phe Leu Ala Pro Ala Lys Ala Thr Leu
1 5 10

<210> SEQ ID NO 562
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 562

Leu Asp Phe Leu Ala Pro Ala Lys Ala Thr Leu Gly Glu
1 5 10

<210> SEQ ID NO 563
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 563

Asp Phe Leu Ala Pro Ala Lys Ala Thr Leu Gly Glu Thr
1 5 10

<210> SEQ ID NO 564
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 564

Ala Lys Ala Thr Leu Gly Glu Thr His Arg Leu Phe Pro
1 5 10

<210> SEQ ID NO 565
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 565

Ala Thr Leu Gly Glu Thr His Arg Leu Phe Pro Asn Thr
1 5 10

<210> SEQ ID NO 566
<211> LENGTH: 13
<212> TYPE: PRT
<213> ORGANISM: Artificial Sequence
<220> FEATURE:
<223> OTHER INFORMATION: MHC class II binding epitope -continued

<400> SEQUENCE: 566

Gly Glu Thr His Arg Leu Phe Pro Asn Thr Met Leu Phe
1 5 10

<210> SEQ ID NO 567
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 567

Glu Thr His Arg Leu Phe Pro Asn Thr Met Leu Phe Ala
1 5 10

<210> SEQ ID NO 568
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 568

Thr His Arg Leu Phe Pro Asn Thr Met Leu Phe Ala Ser
1 5 10

<210> SEQ ID NO 569
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 569

His Arg Leu Phe Pro Asn Thr Met Leu Phe Ala Ser Glu
1 5 10

<210> SEQ ID NO 570
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 570

Arg Leu Phe Pro Asn Thr Met Leu Phe Ala Ser Glu Ala
1 5 10

<210> SEQ ID NO 571
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 571

Phe Pro Asn Thr Met Leu Phe Ala Ser Glu Ala Cys Val
1 5 10

<210> SEQ ID NO 572
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 572

Asn Thr Met Leu Phe Ala Ser Glu Ala Cys Val Gly Ser
1 5 10

<210> SEQ ID NO 573
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 573

Thr Met Leu Phe Ala Ser Glu Ala Cys Val Gly Ser Lys
1 5 10

<210> SEQ ID NO 574
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 574

Met Leu Phe Ala Ser Glu Ala Cys Val Gly Ser Lys Phe
1 5 10

<210> SEQ ID NO 575
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 575

Ala Cys Val Gly Ser Lys Phe Trp Glu Gln Ser Val Arg
1 5 10

<210> SEQ ID NO 576
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 576

Gly Ser Lys Phe Trp Glu Gln Ser Val Arg Leu Gly Ser
1 5 10

<210> SEQ ID NO 577
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 577

Ser Lys Phe Trp Glu Gln Ser Val Arg Leu Gly Ser Trp
1 5 10

<210> SEQ ID NO 578
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 578

-continued

Lys Phe Trp Glu Gln Ser Val Arg Leu Gly Ser Trp Asp
1 5 10

<210> SEQ ID NO 579
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 579

Gln Ser Val Arg Leu Gly Ser Trp Asp Arg Gly Met Gln
1 5 10

<210> SEQ ID NO 580
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 580

Val Arg Leu Gly Ser Trp Asp Arg Gly Met Gln Tyr Ser
1 5 10

<210> SEQ ID NO 581
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 581

Arg Leu Gly Ser Trp Asp Arg Gly Met Gln Tyr Ser His
1 5 10

<210> SEQ ID NO 582
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 582

Gly Ser Trp Asp Arg Gly Met Gln Tyr Ser His Ser Ile
1 5 10

<210> SEQ ID NO 583
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 583

Trp Asp Arg Gly Met Gln Tyr Ser His Ser Ile Ile Thr
1 5 10

<210> SEQ ID NO 584
<211> LENGTH: 13
<212> TYPE: PRT

-continued

<213> ORGANISM: Artificial Sequence
<220> FEATURE:
<223> OTHER INFORMATION: MHC class II binding epitope

<400> SEQUENCE: 584

Arg Gly Met Gln Tyr Ser His Ser Ile Ile Thr Asn Leu
1 5 10

<210> SEQ ID NO 585
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 585

Met Gln Tyr Ser His Ser Ile Ile Thr Asn Leu Leu Tyr
1 5 10

<210> SEQ ID NO 586
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 586

Gln Tyr Ser His Ser Ile Ile Thr Asn Leu Leu Tyr His
1 5 10

<210> SEQ ID NO 587
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 587

Tyr Ser His Ser Ile Ile Thr Asn Leu Leu Tyr His Val
1 5 10

<210> SEQ ID NO 588
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 588

His Ser Ile Ile Thr Asn Leu Leu Tyr His Val Val Gly
1 5 10

<210> SEQ ID NO 589
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 589

Ser Ile Ile Thr Asn Leu Leu Tyr His Val Val Gly Trp
1 5 10

<210> SEQ ID NO 590
<211> LENGTH: 13
<212> TYPE: PRT
<213> ORGANISM: Artificial Sequence -continued
<220> FEATURE:
<223> OTHER INFORMATION: MHC class II binding epitope

<400> SEQUENCE: 590

Thr Asn Leu Leu Tyr His Val Val Gly Trp Thr Asp Trp
1 5 10

<210> SEQ ID NO 591
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 591

Asn Leu Leu Tyr His Val Val Gly Trp Thr Asp Trp Asn
1 5 10

<210> SEQ ID NO 592
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 592

Leu Leu Tyr His Val Val Gly Trp Thr Asp Trp Asn Leu
1 5 10

<210> SEQ ID NO 593
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 593

Tyr His Val Val Gly Trp Thr Asp Trp Asn Leu Ala Leu
1 5 10

<210> SEQ ID NO 594
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 594

His Val Val Gly Trp Thr Asp Trp Asn Leu Ala Leu Asn
1 5 10

<210> SEQ ID NO 595
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 595

Val Val Gly Trp Thr Asp Trp Asn Leu Ala Leu Asn Pro
1 5 10

<210> SEQ ID NO 596
<211> LENGTH: 13
<212> TYPE: PRT
<213> ORGANISM: Artificial Sequence
<220> FEATURE:

<223> OTHER INFORMATION: MHC class II binding epitope

<400> SEQUENCE: 596

Val Gly Trp Thr Asp Trp Asn Leu Ala Leu Asn Pro Glu
1 5 10

<210> SEQ ID NO 597
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 597

Thr Asp Trp Asn Leu Ala Leu Asn Pro Glu Gly Gly Pro
1 5 10

<210> SEQ ID NO 598
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 598

Trp Asn Leu Ala Leu Asn Pro Glu Gly Gly Pro Asn Trp
1 5 10

<210> SEQ ID NO 599
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 599

Leu Ala Leu Asn Pro Glu Gly Gly Pro Asn Trp Val Arg
1 5 10

<210> SEQ ID NO 600
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 600

Pro Asn Trp Val Arg Asn Phe Val Asp Ser Pro Ile Ile
1 5 10

<210> SEQ ID NO 601
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 601

Asn Trp Val Arg Asn Phe Val Asp Ser Pro Ile Ile Val
1 5 10

<210> SEQ ID NO 602
<211> LENGTH: 13
<212> TYPE: PRT
<213> ORGANISM: Artificial Sequence
<220> FEATURE:
<223> OTHER INFORMATION: MHC class II binding epitope -continued

<400> SEQUENCE: 602

Arg Asn Phe Val Asp Ser Pro Ile Ile Val Asp Ile Thr
 1               5                   10

<210> SEQ ID NO 603
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 603

Asn Phe Val Asp Ser Pro Ile Ile Val Asp Ile Thr Lys
 1               5                   10

<210> SEQ ID NO 604
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 604

Ser Pro Ile Ile Val Asp Ile Thr Lys Asp Thr Phe Tyr
 1               5                   10

<210> SEQ ID NO 605
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 605

Pro Ile Ile Val Asp Ile Thr Lys Asp Thr Phe Tyr Lys
 1               5                   10

<210> SEQ ID NO 606
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 606

Ile Ile Val Asp Ile Thr Lys Asp Thr Phe Tyr Lys Gln
 1               5                   10

<210> SEQ ID NO 607
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 607

Val Asp Ile Thr Lys Asp Thr Phe Tyr Lys Gln Pro Met
 1               5                   10

<210> SEQ ID NO 608
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 608

Asp Thr Phe Tyr Lys Gln Pro Met Phe Tyr His Leu Gly
1 5 10

<210> SEQ ID NO 609
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 609

Thr Phe Tyr Lys Gln Pro Met Phe Tyr His Leu Gly His
1 5 10

<210> SEQ ID NO 610
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 610

Gln Pro Met Phe Tyr His Leu Gly His Phe Ser Lys Phe
1 5 10

<210> SEQ ID NO 611
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 611

Pro Met Phe Tyr His Leu Gly His Phe Ser Lys Phe Ile
1 5 10

<210> SEQ ID NO 612
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 612

Met Phe Tyr His Leu Gly His Phe Ser Lys Phe Ile Pro
1 5 10

<210> SEQ ID NO 613
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 613

Tyr His Leu Gly His Phe Ser Lys Phe Ile Pro Glu Gly
1 5 10

<210> SEQ ID NO 614
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 614

-continued

Gly His Phe Ser Lys Phe Ile Pro Glu Gly Ser Gln Arg
 1               5                   10

<210> SEQ ID NO 615
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 615

Ser Lys Phe Ile Pro Glu Gly Ser Gln Arg Val Gly Leu
 1               5                   10

<210> SEQ ID NO 616
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 616

Lys Phe Ile Pro Glu Gly Ser Gln Arg Val Gly Leu Val
 1               5                   10

<210> SEQ ID NO 617
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 617

Ile Pro Glu Gly Ser Gln Arg Val Gly Leu Val Ala Ser
 1               5                   10

<210> SEQ ID NO 618
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 618

Gln Arg Val Gly Leu Val Ala Ser Gln Lys Asn Asp Leu
 1               5                   10

<210> SEQ ID NO 619
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 619

Val Gly Leu Val Ala Ser Gln Lys Asn Asp Leu Asp Ala
 1               5                   10

<210> SEQ ID NO 620
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 620

-continued

Gly Leu Val Ala Ser Gln Lys Asn Asp Leu Asp Ala Val
1 5 10

<210> SEQ ID NO 621
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 621

Ser Gln Lys Asn Asp Leu Asp Ala Val Ala Leu Met His
1 5 10

<210> SEQ ID NO 622
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 622

Asn Asp Leu Asp Ala Val Ala Leu Met His Pro Asp Gly
1 5 10

<210> SEQ ID NO 623
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 623

Asp Ala Val Ala Leu Met His Pro Asp Gly Ser Ala Val
1 5 10

<210> SEQ ID NO 624
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 624

Val Ala Leu Met His Pro Asp Gly Ser Ala Val Val Val
1 5 10

<210> SEQ ID NO 625
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 625

Ala Leu Met His Pro Asp Gly Ser Ala Val Val Val Val
1 5 10

<210> SEQ ID NO 626
<211> LENGTH: 13
<212> TYPE: PRT

-continued

<213> ORGANISM: Artificial Sequence
<220> FEATURE:
<223> OTHER INFORMATION: MHC class II binding epitope

<400> SEQUENCE: 626

Ser Ala Val Val Val Val Leu Asn Arg Ser Ser Lys Asp
1 5 10

<210> SEQ ID NO 627
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 627

Ala Val Val Val Val Leu Asn Arg Ser Ser Lys Asp Val
1 5 10

<210> SEQ ID NO 628
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 628

Val Val Val Val Leu Asn Arg Ser Ser Lys Asp Val Pro
1 5 10

<210> SEQ ID NO 629
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 629

Val Val Val Leu Asn Arg Ser Ser Lys Asp Val Pro Leu
1 5 10

<210> SEQ ID NO 630
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 630

Val Val Leu Asn Arg Ser Ser Lys Asp Val Pro Leu Thr
1 5 10

<210> SEQ ID NO 631
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 631

Lys Asp Val Pro Leu Thr Ile Lys Asp Pro Ala Val Gly
1 5 10

<210> SEQ ID NO 632
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 632

Val Pro Leu Thr Ile Lys Asp Pro Ala Val Gly Phe Leu
1 5 10

<210> SEQ ID NO 633
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 633

Pro Leu Thr Ile Lys Asp Pro Ala Val Gly Phe Leu Glu
1 5 10

<210> SEQ ID NO 634
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 634

Leu Thr Ile Lys Asp Pro Ala Val Gly Phe Leu Glu Thr
1 5 10

<210> SEQ ID NO 635
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 635

Pro Ala Val Gly Phe Leu Glu Thr Ile Ser Pro Gly Tyr
1 5 10

<210> SEQ ID NO 636
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 636

Val Gly Phe Leu Glu Thr Ile Ser Pro Gly Tyr Ser Ile
1 5 10

<210> SEQ ID NO 637
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 637

Gly Phe Leu Glu Thr Ile Ser Pro Gly Tyr Ser Ile His
1 5 10

<210> SEQ ID NO 638
<211> LENGTH: 13
<212> TYPE: PRT
<213> ORGANISM: Artificial Sequence
<220> FEATURE:

-continued

```
<223> OTHER INFORMATION: MHC class II binding epitope

<400> SEQUENCE: 638

Phe Leu Glu Thr Ile Ser Pro Gly Tyr Ser Ile His Thr
 1               5                  10


<210> SEQ ID NO 639
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 639

Glu Thr Ile Ser Pro Gly Tyr Ser Ile His Thr Tyr Leu
 1               5                  10


<210> SEQ ID NO 640
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 640

Pro Gly Tyr Ser Ile His Thr Tyr Leu Trp His Arg Gln
 1               5                  10


<210> SEQ ID NO 641
<211> LENGTH: 13
<212> TYPE: PRT
<213> ORGANISM: Artificial Sequence
<220> FEATURE:
<223> OTHER INFORMATION: MHC class II binding epitope

<400> SEQUENCE: 641

Pro Gly Tyr Ser Ile His Thr Tyr Leu Trp Arg Arg Gln
 1               5                  10


<210> SEQ ID NO 642
<211> LENGTH: 121
<212> TYPE: PRT
<213> ORGANISM: Mus Musculus

<400> SEQUENCE: 642

Gln Val Gln Leu Gln Gln Pro Gly Ala Glu Leu Val Lys Pro Gly Ala
 1               5                  10                  15

Ser Val Lys Leu Ser Cys Lys Ala Ser Gly Tyr Thr Phe Thr Ser His
            20                  25                  30

Trp Met His Trp Val Lys Gln Arg Ala Gly Gln Gly Leu Glu Trp Ile
        35                  40                  45

Gly Glu Phe Asn Pro Ser Asn Gly Arg Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Ser Arg Asp Tyr Asp Tyr Asp Gly Arg Tyr Phe Asp Tyr Trp Gly
            100                 105                 110

Gln Gly Thr Thr Leu Thr Val Ser Ser
        115                 120
```

-continued

<210> SEQ ID NO 643
<211> LENGTH: 106
<212> TYPE: PRT
<213> ORGANISM: Mus Musculus

<400> SEQUENCE: 643

```
Gln Ile Val Leu Thr Gln Ser Pro Ala Ile Met Ser Ala Ser Pro Gly
 1               5                  10                  15

Glu Lys Val Thr Met Thr Cys Ser Ala Ser Ser Ser Val Thr Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser His Ile Phe Thr
                85                  90                  95

Phe Gly Ser Gly Thr Lys Leu Glu Ile Lys
            100                 105
```

<210> SEQ ID NO 644
<211> LENGTH: 121
<212> TYPE: PRT
<213> ORGANISM: Artificial Sequence
<220> FEATURE:
<223> OTHER INFORMATION: MHC class II binding epitope

<400> SEQUENCE: 644

```
Gln Val Gln Leu Val Gln Ser Gly Ala Glu Leu Val Lys Pro Gly Ala
 1               5                  10                  15

Ser Val Lys Leu Ser Cys Lys Ala Ser Gly Tyr Thr Phe Thr Ser His
            20                  25                  30

Trp Met His Trp Val Lys Gln Ala Ala Gly Gln Gly Leu Glu Trp Ile
        35                  40                  45

Gly Glu Phe Asn Pro Ser Asn Gly Arg Thr Asn Tyr Asn Glu Lys Phe
    50                  55                  60

Lys Ser Arg Ala Thr Leu Thr Val Asp Lys Ser Thr Ser Thr Ala Tyr
65                  70                  75                  80

Met Gln Leu Ser Ser Leu Thr Ser Glu Asp Ser Ala Val Tyr Tyr Cys
                85                  90                  95

Ala Ser Arg Asp Tyr Asp Tyr Asp Gly Arg Tyr Phe Asp Tyr Trp Gly
            100                 105                 110

Gln Gly Thr Thr Leu Thr Val Ser Ser
        115                 120
```

<210> SEQ ID NO 645
<211> LENGTH: 106
<212> TYPE: PRT
<213> ORGANISM: Artificial Sequence
<220> FEATURE:
<223> OTHER INFORMATION: MHC class II binding epitope

<400> SEQUENCE: 645

```
Gln Ile Val Leu Thr Gln Ser Pro Ala Thr Leu Ser Ala Ser Pro Gly
 1               5                  10                  15

Glu Arg Ala Thr Met Ser Cys Ser Ala Ser Ser Ser Val Thr Tyr Met
            20                  25                  30
```

-continued

```
Tyr Trp Tyr Gln Gln Lys Pro Gly Gln Ser Pro Arg Leu Leu Ile Tyr
        35                  40                  45

Asp Thr Ser Asn Leu Ala Ser Gly Val Pro Ala Arg Phe Ser Gly Ser
    50                  55                  60

Gly Ser Gly Thr Ser Tyr Thr Leu Thr Ile Ser Ser Leu Glu Ala Glu
65                  70                  75                  80

Asp Ala Ala Thr Tyr Tyr Cys Gln Gln Trp Ser Ser His Ile Phe Thr
                85                  90                  95

Phe Gly Gln Gly Thr Lys Leu Glu Ile Lys
            100                 105


<210> SEQ ID NO 646
<211> LENGTH: 121
<212> TYPE: PRT
<213> ORGANISM: Artificial Sequence
<220> FEATURE:
<223> OTHER INFORMATION: MHC class II binding epitope

<400> SEQUENCE: 646

Gln Val Gln Leu Val Gln Ser Gly Ala Glu Leu Val Lys Pro Gly Ala
 1               5                  10                  15

Ser Val Lys Leu Ser Cys Lys Ala Ser Gly Tyr Thr Phe Thr Ser His
            20                  25                  30

Trp Met His Trp Val Lys Gln Ala Pro Gly Gln Gly Pro Glu Trp Ala
        35                  40                  45

Gly Glu Phe Asn Pro Ser Asn Gly Arg Thr Asn Tyr Asn Glu Lys Phe
    50                  55                  60

Lys Ser Arg Val Thr Ile Thr Val Asp Lys Ser Thr Ser Thr Ala Tyr
65                  70                  75                  80

Met Gln Leu Ser Ser Leu Thr Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
            100                 105                 110

Gln Gly Thr Thr Leu Thr Val Ser Ser
        115                 120


<210> SEQ ID NO 647
<211> LENGTH: 104
<212> TYPE: PRT
<213> ORGANISM: Artificial Sequence
<220> FEATURE:
<223> OTHER INFORMATION: De-immunized MHC class II binding epitope

<400> SEQUENCE: 647

Gln Ile Val Leu Thr Gln Ser Pro Ala Thr Leu Ser Ala Ser Pro Gly
 1               5                  10                  15

Glu Arg Ala Thr Met Ser Cys Ser Ala Ser Ser Ser Val Thr Tyr Met
            20                  25                  30

Tyr Trp His Gln Gln Lys Pro Gly Gln Ser Pro Arg Leu Leu Ile Tyr
        35                  40                  45

Asp Asn Leu Ala Ser Gly Val Pro Ala Arg Phe Ser Gly Ser Gly Ser
    50                  55                  60

Gly Thr Ser Tyr Thr Leu Thr Ile Ser Ser Leu Glu Ala Glu Asp Ala
65                  70                  75                  80

Ala Thr Tyr Tyr Cys Gln Gln Trp Ser Ser His Pro Phe Thr Phe Gly
                85                  90                  95

Gln Gly Thr Lys Val Glu Ile Lys
```

-continued

100

<210> SEQ ID NO 648
<211> LENGTH: 121
<212> TYPE: PRT
<213> ORGANISM: Artificial Sequence
<220> FEATURE:
<223> OTHER INFORMATION: De-immunized MHC class II binding epitope

<400> SEQUENCE: 648

Gln Val Gln Leu Val Gln Ser Gly Ala Glu Leu Val Lys Pro Gly Ala
1 5 10 15

Ser Val Lys Leu Ser Cys Lys Ala Ser Gly Tyr Thr Phe Thr Ser His
20 25 30

Trp Met His Trp Val Lys Gln Ala Pro Gly Gln Gly Pro Glu Trp Ile
35 40 45

Gly Glu Phe Asn Pro Ser Asn Gly Arg Thr Asn Tyr Asn Glu Lys Phe
50 55 60

Lys Ser Arg Val Thr Ile Thr Val Asp Lys Ser Thr Ser Thr Ala Tyr
65 70 75 80

Met Gln Leu Ser Ser Leu Thr Ser Glu Asp Thr Ala Val Tyr Tyr Cys
85 90 95

Ala Ser Arg Asp Tyr Asp Tyr Asp Gly Arg Tyr Phe Asp Tyr Trp Gly
100 105 110

Gln Gly Thr Thr Leu Thr Val Ser Ser
115 120

<210> SEQ ID NO 649
<211> LENGTH: 106
<212> TYPE: PRT
<213> ORGANISM: Artificial Sequence
<220> FEATURE:
<223> OTHER INFORMATION: De-immunized MHC class II binding epitope

<400> SEQUENCE: 649

Gln Ile Val Leu Thr Gln Ser Pro Ala Thr Leu Ser Ala Ser Pro Gly
1 5 10 15

Glu Arg Ala Thr Met Ser Cys Ser Ala Ser Ser Ser Val Thr Tyr Met
20 25 30

Tyr Trp His Gln Gln Lys Pro Gly Gln Ser Pro Arg Ala Leu Ile Tyr
35 40 45

Asp Thr Ser Asn Leu Ala Ser Gly Val Pro Ala Arg Phe Ser Gly Ser
50 55 60

Gly Ser Gly Thr Ser Tyr Thr Leu Thr Ile Ser Ser Leu Glu Ala Glu
65 70 75 80

Asp Ala Ala Thr Tyr Tyr Cys Gln Gln Trp Ser Ser His Pro Phe Thr
85 90 95

Phe Gly Gln Gly Thr Lys Val Glu Ile Lys
100 105

<210> SEQ ID NO 650
<211> LENGTH: 121
<212> TYPE: PRT

-continued

<213> ORGANISM: Artificial Sequence
<220> FEATURE:
<223> OTHER INFORMATION: De-immunized MHC class II binding epitope

<400> SEQUENCE: 650

```
Gln Val Gln Leu Val Gln Ser Gly Ala Glu Leu Val Lys Pro Gly Ala
 1               5                  10                  15

Ser Val Lys Leu Ser Cys Lys Ala Ser Gly Tyr Thr Phe Thr Ser His
            20                  25                  30

Trp Met His Trp Val Lys Gln Ala Pro Gly Gln Gly Leu Glu Trp Ile
        35                  40                  45

Gly Glu Phe Asn Pro Ser Asn Gly Arg Thr Asn Tyr Asn Glu Lys Phe
    50                  55                  60

Lys Ser Arg Val Thr Ile Thr Val Asp Lys Ser Thr Ser Thr Ala Tyr
65                  70                  75                  80

Met Gln Leu Ser Ser Leu Thr Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
            100                 105                 110

Gln Gly Thr Thr Leu Thr Val Ser Ser
        115                 120
```

<210> SEQ ID NO 651
<211> LENGTH: 106
<212> TYPE: PRT
<213> ORGANISM: Artificial Sequence
<220> FEATURE:
<223> OTHER INFORMATION: de-immunized MHC class II binding epitope

<400> SEQUENCE: 651

```
Gln Ile Val Leu Thr Gln Ser Pro Ala Thr Leu Ser Ala Ser Pro Gly
 1               5                  10                  15

Glu Arg Ala Thr Met Ser Cys Ser Ala Ser Ser Ser Val Thr Tyr Met
            20                  25                  30

Tyr Trp His Gln Gln Lys Pro Gly Gln Ser Pro Arg Leu Leu Ile Tyr
        35                  40                  45

Asp Thr Ser Asn Leu Ala Ser Gly Val Pro Ala Arg Phe Ser Gly Ser
    50                  55                  60

Gly Ser Gly Thr Ser Tyr Thr Leu Thr Ile Ser Ser Leu Glu Ala Glu
65                  70                  75                  80

Asp Ala Ala Thr Tyr Tyr Cys Gln Gln Trp Ser Ser His Pro Phe Thr
                85                  90                  95

Phe Gly Gln Gly Thr Lys Val Glu Ile Lys
            100                 105
```

<210> SEQ ID NO 652
<211> LENGTH: 121
<212> TYPE: PRT
<213> ORGANISM: Artificial Sequence
<220> FEATURE:
<223> OTHER INFORMATION: MHC class II binding epitope

<400> SEQUENCE: 652

```
Gln Val Gln Leu Val Gln Ser Gly Ala Glu Leu Val Lys Pro Gly Ala
 1               5                  10                  15

Ser Val Lys Leu Ser Cys Lys Ala Ser Gly Tyr Thr Phe Thr Ser His
            20                  25                  30

Trp Met His Trp Val Lys Gln Ala Pro Gly Gln Gly Leu Glu Trp Ile
        35                  40                  45
```

-continued

```
Gly Glu Phe Asn Pro Ser Asn Gly Arg Thr Asn Tyr Asn Glu Lys Phe
    50                  55                  60

Lys Ser Arg Ala Thr Leu Thr Val Asp Lys Ser Thr Ser Thr Ala Tyr
65                  70                  75                  80

Met Gln Leu Ser Ser Leu Thr Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
            100                 105                 110

Gln Gly Thr Thr Leu Thr Val Ser Ser
        115                 120


<210> SEQ ID NO 653
<211> LENGTH: 106
<212> TYPE: PRT
<213> ORGANISM: Artificial Sequence
<220> FEATURE:
<223> OTHER INFORMATION: De-immunized MHC class II binding epitope

<400> SEQUENCE: 653

Gln Ile Val Leu Thr Gln Ser Pro Ala Thr Leu Ser Ala Ser Pro Gly
 1               5                  10                  15

Glu Arg Ala Thr Met Ser Cys Ser Ala Ser Ser Ser Val Thr Tyr Met
            20                  25                  30

Tyr Trp His Gln Gln Lys Pro Gly Gln Ser Pro Arg Leu Leu Ile Tyr
        35                  40                  45

Asp Thr Ser Asn Leu Ala Ser Gly Val Pro Ala Arg Phe Ser Gly Ser
    50                  55                  60

Gly Ser Gly Thr Ser Tyr Thr Leu Thr Ile Ser Ser Leu Glu Ala Glu
65                  70                  75                  80

Asp Ala Ala Thr Tyr Tyr Cys Gln Gln Trp Ser Ser His Ile Phe Thr
                85                  90                  95

Phe Gly Gln Gly Thr Lys Val Glu Ile Lys
            100                 105


<210> SEQ ID NO 654
<211> LENGTH: 121
<212> TYPE: PRT
<213> ORGANISM: Artificial Sequence
<220> FEATURE:
<223> OTHER INFORMATION: De-immunized MHC class II binding epitope

<400> SEQUENCE: 654

Gln Val Gln Leu Val Gln Ser Gly Ala Glu Leu Val Lys Pro Gly Ala
 1               5                  10                  15

Ser Val Lys Leu Ser Cys Lys Ala Ser Gly Tyr Thr Phe Thr Ser His
            20                  25                  30

Trp Met His Trp Val Lys Gln Ala Ala Gly Gln Gly Leu Glu Trp Ile
        35                  40                  45

Gly Glu Phe Asn Pro Ser Asn Gly Arg Thr Asn Tyr Asn Glu Lys Phe
    50                  55                  60

Lys Ser Arg Ala Thr Leu Thr Val Asp Lys Ser Thr Ser Thr Ala Tyr
65                  70                  75                  80

Met Gln Leu Ser Ser Leu Thr Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
            100                 105                 110
```

-continued

```
Gln Gly Thr Thr Leu Thr Val Ser Ser
        115                 120


<210> SEQ ID NO 655
<211> LENGTH: 106
<212> TYPE: PRT
<213> ORGANISM: Artificial Sequence
<220> FEATURE:
<223> OTHER INFORMATION: De-immunized MHC class II binding epitope

<400> SEQUENCE: 655

Gln Ile Val Leu Thr Gln Ser Pro Ala Thr Leu Ser Ala Ser Pro Gly
 1               5                  10                  15

Glu Arg Ala Thr Met Ser Cys Ser Ala Ser Ser Ser Val Thr Tyr Met
            20                  25                  30

Tyr Trp Tyr Gln Gln Lys Pro Gly Gln Ser Pro Arg Leu Leu Ile Tyr
        35                  40                  45

Asp Thr Ser Asn Leu Ala Ser Gly Val Pro Ala Arg Phe Ser Gly Ser
    50                  55                  60

Gly Ser Gly Thr Ser Tyr Thr Leu Thr Ile Ser Ser Leu Glu Ala Glu
65                  70                  75                  80

Asp Ala Ala Thr Tyr Tyr Cys Gln Gln Trp Ser Ser His Ile Phe Thr
                85                  90                  95

Phe Gly Gln Gly Thr Lys Val Glu Ile Lys
            100                 105


<210> SEQ ID NO 656
<211> LENGTH: 121
<212> TYPE: PRT
<213> ORGANISM: Artificial Sequence
<220> FEATURE:
<223> OTHER INFORMATION: De-immunized MHC class II binding epitope

<400> SEQUENCE: 656

Gln Val Gln Leu Gln Gln Pro Gly Ala Glu Leu Val Lys Pro Gly Ala
 1               5                  10                  15

Ser Val Lys Leu Ser Cys Lys Ala Ser Gly Tyr Thr Phe Thr Ser His
            20                  25                  30

Trp Met His Trp Val Lys Gln Ala Pro Gly Gln Gly Leu Glu Trp Ile
        35                  40                  45

Gly Glu Phe Asn Pro Ser Asn Gly Arg Thr Asn Tyr Asn Glu Lys Phe
    50                  55                  60

Lys Ser Arg Val Thr Ile Thr Val Asp Lys Ser Ser Ser Thr Ala Tyr
65                  70                  75                  80

Met Gln Leu Ser Ser Leu Thr Ser Glu Asp Thr Ala Val Tyr Tyr Cys
                85                  90                  95

Ala Ser Arg Asp Tyr Asp Tyr Asp Gly Arg Tyr Phe Asp Tyr Trp Gly
            100                 105                 110

Gln Gly Thr Thr Leu Thr Val Ser Ser
        115                 120


<210> SEQ ID NO 657
<211> LENGTH: 106
<212> TYPE: PRT
<213> ORGANISM: Artificial Sequence
<220> FEATURE:
<223> OTHER INFORMATION: De-immunized MHC class II binding epitope

<400> SEQUENCE: 657
```

-continued

Gln Ile Val Leu Thr Gln Ser Pro Ala Thr Leu Ser Ala Ser Pro Gly
1 5 10 15

Glu Lys Ala Thr Met Thr Cys Ser Ala Ser Ser Ser Val Thr Tyr Met
20 25 30

Tyr Trp Tyr Gln Gln Lys Pro Gly Ser Ser Pro Arg Leu Leu Ile Tyr
35 40 45

Asp Thr Ser Asn Leu Ala Ser Gly Val Pro Val Arg Phe Ser Gly Ser
50 55 60

Gly Ser Gly Thr Ser Tyr Ser Leu Thr Ile Ser Arg Leu Glu Ala Glu
65 70 75 80

Asp Ala Ala Thr Tyr Tyr Cys Gln Gln Trp Ser Ser His Ile Phe Thr
85 90 95

Phe Gly Gln Gly Thr Lys Val Glu Ile Lys
100 105

<210> SEQ ID NO 658
<211> LENGTH: 116
<212> TYPE: PRT
<213> ORGANISM: Artificial Sequence
<220> FEATURE:
<223> OTHER INFORMATION: MHC class II binding epitope

<400> SEQUENCE: 658

Gln Ile Gln Leu Val Gln Ser Gly Pro Glu Leu Lys Lys Pro Gly Ser
1 5 10 15

Ser Val Lys Ile Ser Cys Lys Ala Ser Gly Tyr Thr Phe Thr Asn Tyr
20 25 30

Gly Met Asn Trp Val Lys Gln Ala Pro Gly Gln Gly Leu Lys Trp Met
35 40 45

Gly Trp Ile Asn Thr Tyr Thr Gly Glu Pro Thr Tyr Ala Asp Asp Phe
50 55 60

Lys Gly Arg Phe Thr Phe Thr Leu Glu Thr Ser Thr Ser Thr Ala Tyr
65 70 75 80

Leu Gln Leu Asn Asn Leu Arg Ser Glu Asp Met Ala Thr Tyr Phe Cys
85 90 95

Val Arg Phe Ile Ser Lys Gly Asp Tyr Trp Gly Gln Gly Thr Thr Val
100 105 110

Thr Val Ser Ser
115

<210> SEQ ID NO 659
<211> LENGTH: 106
<212> TYPE: PRT
<213> ORGANISM: Artificial Sequence
<220> FEATURE:
<223> OTHER INFORMATION: MHC class II binding epitope

<400> SEQUENCE: 659

Gln Ile Leu Leu Thr Gln Ser Pro Ala Ser Leu Ala Val Ser Pro Gly
1 5 10 15

Gln Arg Ala Thr Ile Thr Cys Ser Ala Ser Ser Ser Val Ser Tyr Met
20 25 30

Leu Trp Tyr Gln Gln Lys Pro Gly Gln Pro Pro Lys Pro Trp Ile Phe
35 40 45

Asp Thr Ser Asn Leu Ala Ser Gly Phe Pro Ala Arg Phe Ser Gly Ser
50 55 60

Gly Ser Gly Thr Ser Tyr Thr Leu Thr Ile Asn Ser Leu Glu Ala Glu
65 70 75 80

-continued

```
Asp Ala Ala Thr Tyr Tyr Cys His Gln Arg Ser Gly Tyr Pro Tyr Thr
                85                  90                  95

Phe Gly Gly Gly Thr Lys Val Glu Ile Lys
            100                 105


<210> SEQ ID NO 660
<211> LENGTH: 116
<212> TYPE: PRT
<213> ORGANISM: Artificial Sequence
<220> FEATURE:
<223> OTHER INFORMATION: De-immunized MHC class II binding epitope

<400> SEQUENCE: 660

Gln Ile Gln Leu Val Gln Ser Gly Pro Glu Leu Lys Lys Pro Gly Ser
 1               5                  10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Thr Ile Thr Ala Glu Thr Ser Thr Ser Thr Leu Tyr
65                  70                  75                  80

Leu Gln Leu Asn Asn Leu Arg Ser Glu Asp Thr Ala Thr Tyr Phe Cys
                85                  90                  95

Val Arg Phe Met Ser Lys Gly Asp Tyr Trp Gly Gln Gly Thr Thr Val
            100                 105                 110

Thr Val Ser Ser
        115


<210> SEQ ID NO 661
<211> LENGTH: 106
<212> TYPE: PRT
<213> ORGANISM: Artificial Sequence
<220> FEATURE:
<223> OTHER INFORMATION: De-immunized MHC class II binding epitope

<400> SEQUENCE: 661

Gln Ile Val Leu Thr Gln Ser Pro Ala Ser Leu Ala Val Ser Pro Gly
 1               5                  10                  15

Gln Arg Ala Thr Ile Thr Cys Ser Ala Ser Ser Ser Val Ser Tyr Ile
            20                  25                  30

Leu Trp Tyr Gln Gln Lys Pro Gly Gln Pro Pro Lys Pro Trp Ile Phe
        35                  40                  45

Asp Thr Ser Asn Leu Ala Ser Gly Phe Pro Ser Arg Phe Ser Gly Ser
    50                  55                  60

Gly Ser Gly Thr Ser Tyr Thr Leu Thr Ile Asn Ser Leu Glu Ala Glu
65                  70                  75                  80

Asp Ala Ala Thr Tyr Tyr Cys His Gln Arg Ser Gly Tyr Pro Tyr Thr
                85                  90                  95

Phe Gly Gly Gly Thr Lys Val Glu Ile Lys
            100                 105


<210> SEQ ID NO 662
<211> LENGTH: 116
<212> TYPE: PRT
<213> ORGANISM: Artificial Sequence
<220> FEATURE:
<223> OTHER INFORMATION: De-immunized MHC class II binding epitope
```

-continued

<400> SEQUENCE: 662

Gln Ile Gln Leu Val Gln Ser Gly Pro Glu Leu Lys Lys Pro Gly Ser
1 5 10 15

Ser Val Lys Ile Ser Cys Lys Ala Ser Gly Tyr Thr Phe Thr Asn Tyr
20 25 30

Gly Met Asn Trp Val Arg Gln Ala Pro Gly Lys Gly Leu Lys Trp Met
35 40 45

Gly Trp Ile Asn Thr Tyr Thr Gly Glu Pro Thr Tyr Ala Asp Asp Phe
50 55 60

Lys Gly Arg Phe Thr Ile Thr Ala Glu Thr Ser Thr Ser Thr Leu Tyr
65 70 75 80

Leu Gln Leu Asn Asn Leu Arg Ser Glu Asp Thr Ala Thr Tyr Phe Cys
85 90 95

Val Arg Phe Ile Ser Lys Gly Asp Tyr Trp Gly Gln Gly Thr Thr Val
100 105 110

Thr Val Ser Ser
115

<210> SEQ ID NO 663
<211> LENGTH: 106
<212> TYPE: PRT
<213> ORGANISM: Artificial Sequence
<220> FEATURE:
<223> OTHER INFORMATION: De-immunized MHC class II binding epitope

<400> SEQUENCE: 663

Gln Ile Val Leu Thr Gln Ser Pro Ala Ser Leu Ala Val Ser Pro Gly
1 5 10 15

Gln Arg Ala Thr Ile Thr Cys Ser Ala Ser Ser Ser Val Ser Tyr Met
20 25 30

Leu Trp Tyr Gln Gln Lys Pro Gly Gln Pro Pro Lys Pro Trp Ile Phe
35 40 45

Asp Thr Ser Asn Leu Ala Ser Gly Phe Pro Ser Arg Phe Ser Gly Ser
50 55 60

Gly Ser Gly Thr Ser Tyr Thr Leu Thr Ile Asn Ser Leu Glu Ala Glu
65 70 75 80

Asp Ala Ala Thr Tyr Tyr Cys His Gln Arg Ser Gly Tyr Pro Tyr Thr
85 90 95

Phe Gly Gly Gly Thr Lys Val Glu Ile Lys
100 105

<210> SEQ ID NO 664
<211> LENGTH: 116
<212> TYPE: PRT
<213> ORGANISM: Artificial Sequence
<220> FEATURE:
<223> OTHER INFORMATION: De-immunized MHC class II binding epitope

<400> SEQUENCE: 664

Gln Ile Gln Leu Val Gln Ser Gly Pro Glu Leu Lys Lys Pro Gly Ser
1 5 10 15

Ser Val Lys Ile Ser Cys Lys Ala Ser Gly Tyr Thr Phe Thr Asn Tyr
20 25 30

Gly Met Asn Trp Val Arg Gln Ala Pro Gly Lys Gly Leu Lys Trp Met
35 40 45

Gly Trp Ile Asn Thr Tyr Thr Gly Glu Pro Thr Tyr Ala Asp Asp Phe
50 55 60

```
Lys Gly Arg Phe Thr Ile Thr Leu Glu Thr Ser Thr Ser Thr Ala Tyr
65                  70                  75                  80

Leu Gln Leu Asn Asn Leu Arg Ser Glu Asp Thr Ala Thr Tyr Phe Cys
                85                  90                  95

Val Arg Phe Ile Ser Lys Gly Asp Tyr Trp Gly Gln Gly Thr Thr Val
            100                 105                 110

Thr Val Ser Ser
        115


<210> SEQ ID NO 665
<211> LENGTH: 106
<212> TYPE: PRT
<213> ORGANISM: Artificial Sequence
<220> FEATURE:
<223> OTHER INFORMATION: De-immunized MHC class II binding epitope

<400> SEQUENCE: 665

Gln Ile Leu Leu Thr Gln Ser Pro Ala Ser Leu Ala Val Ser Pro Gly
 1               5                  10                  15

Gln Arg Ala Thr Ile Thr Cys Ser Ala Ser Ser Ser Val Ser Tyr Met
            20                  25                  30

Leu Trp Tyr Gln Gln Lys Pro Gly Gln Pro Pro Lys Pro Trp Ile Phe
        35                  40                  45

Asp Thr Ser Asn Leu Ala Ser Gly Phe Pro Ser Arg Phe Ser Gly Ser
    50                  55                  60

Gly Ser Gly Thr Ser Tyr Thr Leu Thr Ile Asn Ser Leu Glu Ala Glu
65                  70                  75                  80

Asp Ala Ala Thr Tyr Tyr Cys His Gln Arg Ser Gly Tyr Pro Tyr Thr
                85                  90                  95

Phe Gly Gly Gly Thr Lys Val Glu Ile Lys
            100                 105


<210> SEQ ID NO 666
<211> LENGTH: 116
<212> TYPE: PRT
<213> ORGANISM: Artificial Sequence
<220> FEATURE:
<223> OTHER INFORMATION: De-immunized MHC class II binding epitope

<400> SEQUENCE: 666

Gln Ile Gln Leu Val Gln Ser Gly Pro Glu Leu Lys Lys Pro Gly Ser
 1               5                  10                  15

Ser Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Thr Ile Thr Leu Glu Thr Ser Thr Ser Thr Ala Tyr
65                  70                  75                  80

Leu Gln Leu Asn Asn Leu Arg Ser Glu Asp Thr Ala Thr Tyr Phe Cys
                85                  90                  95

Val Arg Phe Ile Ser Lys Gly Asp Tyr Trp Gly Gln Gly Thr Thr Val
            100                 105                 110

Thr Val Ser Ser
        115
```

-continued

<210> SEQ ID NO 667
<211> LENGTH: 106
<212> TYPE: PRT
<213> ORGANISM: Artificial Sequence
<220> FEATURE:
<223> OTHER INFORMATION: De-immunized MHC class II binding epitope

<400> SEQUENCE: 667

```
Gln Ile Leu Leu Thr Gln Ser Pro Ala Ser Leu Ala Val Ser Pro Gly
 1               5                  10                  15

Gln Arg Ala Thr Ile Thr Cys Ser Ala Ser Ser Ser Val Ser Tyr Met
            20                  25                  30

Leu Trp Tyr Gln Gln Lys Pro Gly Gln Pro Pro Lys Pro Trp Ile Phe
        35                  40                  45

Asp Thr Ser Asn Leu Ala Ser Gly Phe Pro Ala Arg Phe Ser Gly Ser
    50                  55                  60

Gly Ser Gly Thr Ser Tyr Thr Leu Thr Ile Asn Ser Leu Glu Ala Glu
65                  70                  75                  80

Asp Ala Ala Thr Tyr Tyr Cys His Gln Arg Ser Gly Tyr Pro Tyr Thr
                85                  90                  95

Phe Gly Gly Gly Thr Lys Val Glu Ile Lys
            100                 105
```

<210> SEQ ID NO 668
<211> LENGTH: 116
<212> TYPE: PRT
<213> ORGANISM: Artificial Sequence
<220> FEATURE:
<223> OTHER INFORMATION: De-immunized MHC class II binding epitope

<400> SEQUENCE: 668

```
Gln Ile Gln Leu Val Gln Ser Gly Pro Glu Leu Lys Lys Pro Gly Ser
 1               5                  10                  15

Ser Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Thr Leu Glu Thr Ser Thr Ser Thr Ala Tyr
65                  70                  75                  80

Leu Gln Leu Asn Asn Leu Arg Ser Glu Asp Thr Ala Thr Tyr Phe Cys
                85                  90                  95

Val Arg Phe Ile Ser Lys Gly Asp Tyr Trp Gly Gln Gly Thr Thr Val
            100                 105                 110

Thr Val Ser Ser
        115
```

<210> SEQ ID NO 669
<211> LENGTH: 106
<212> TYPE: PRT
<213> ORGANISM: Artificial Sequence
<220> FEATURE:
<223> OTHER INFORMATION: De-immunized MHC class II binding epitope

<400> SEQUENCE: 669

```
Gln Ile Leu Leu Thr Gln Ser Pro Ala Ser Leu Ala Val Ser Pro Gly
 1               5                  10                  15

Gln Arg Ala Thr Ile Thr Cys Ser Ala Ser Ser Ser Val Ser Tyr Met
            20                  25                  30
```

-continued

```
Leu Trp Tyr Gln Gln Lys Pro Gly Ser Ser Pro Lys Pro Trp Ile Tyr
        35                  40                  45

Asp Thr Ser Asn Leu Ala Ser Gly Phe Pro Ala Arg Phe Ser Gly Ser
    50                  55                  60

Gly Ser Gly Thr Ser Tyr Thr Leu Thr Ile Asn Ser Leu Glu Ala Glu
65                  70                  75                  80

Asp Ala Ala Thr Tyr Tyr Cys His Gln Arg Ser Gly Tyr Pro Tyr Thr
                85                  90                  95

Phe Gly Gly Gly Thr Lys Val Glu Ile Lys
            100                 105


<210> SEQ ID NO 670
<211> LENGTH: 116
<212> TYPE: PRT
<213> ORGANISM: Artificial Sequence
<220> FEATURE:
<223> OTHER INFORMATION: MHC class II binding epitope

<400> SEQUENCE: 670

Gln Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Phe Thr Asn Tyr
            20                  25                  30

Gly Met Asn Trp Val Arg Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Val Phe Ser Leu Glu Thr Ser Ala Ser Thr Ala Phe
65                  70                  75                  80

Leu Gln Leu Asn Asn Leu Arg Ser Glu Asp Thr Ala Thr Tyr Phe Cys
                85                  90                  95

Val Arg Phe Ile Ser Lys Gly Asp Tyr Trp Gly Gln Gly Thr Ser Val
            100                 105                 110

Thr Val Ser Ser
        115


<210> SEQ ID NO 671
<211> LENGTH: 106
<212> TYPE: PRT
<213> ORGANISM: Artificial Sequence
<220> FEATURE:
<223> OTHER INFORMATION: MHC class II binding epitope

<400> SEQUENCE: 671

Gln Ile Val Leu Thr Gln Ser Pro Ala Thr Leu Ser Ala Ser Pro Gly
 1               5                  10                  15

Glu Arg Val Thr Ile Thr Cys Ser Ala Ser Ser Ser Val Ser Tyr Met
            20                  25                  30

Leu Trp Tyr Leu Gln Lys Pro Gly Ser Ser Pro Lys Pro Trp Ile Phe
        35                  40                  45

Asp Thr Ser Asn Leu Ala Ser Gly Phe Pro Ser Arg Phe Ser Gly Ser
    50                  55                  60

Gly Ser Gly Thr Thr Tyr Ser Leu Ile Ile Ser Ser Leu Glu Ala Glu
65                  70                  75                  80

Asp Ala Ala Thr Tyr Tyr Cys His Gln Arg Ser Gly Tyr Pro Tyr Thr
                85                  90                  95
```

Phe Gly Gly Gly Thr Lys Leu Glu Ile Lys
100 105

<210> SEQ ID NO 672
<211> LENGTH: 116
<212> TYPE: PRT
<213> ORGANISM: Mus Musculus

<400> SEQUENCE: 672

Gln Ile Gln Leu Val Gln Ser Gly Pro Glu Leu Lys Lys Pro Gly Glu
1 5 10 15

Thr Val Lys Ile Ser Cys Lys Ala Ser Gly Tyr Thr Phe Thr Asn Tyr
20 25 30

Gly Met Asn Trp Val Lys Gln Thr Pro Gly Lys Gly Leu Lys Trp Met
35 40 45

Gly Trp Ile Asn Thr Tyr Thr Gly Glu Pro Thr Tyr Ala Asp Asp Phe
50 55 60

Lys Gly Arg Phe Ala Phe Ser Leu Glu Thr Ser Ala Ser Thr Ala Phe
65 70 75 80

Leu Gln Ile Asn Asn Leu Arg Asn Glu Asp Met Ala Thr Tyr Phe Cys
85 90 95

Val Arg Phe Ile Ser Lys Gly Asp Tyr Trp Gly Gln Gly Thr Ser Val
100 105 110

Thr Val Ser Ser
115

<210> SEQ ID NO 673
<211> LENGTH: 106
<212> TYPE: PRT
<213> ORGANISM: Mus Musculus

<400> SEQUENCE: 673

Gln Ile Leu Leu Thr Gln Ser Pro Ala Ile Met Ser Ala Ser Pro Gly
1 5 10 15

Glu Lys Val Thr Met Thr Cys Ser Ala Ser Ser Ser Val Ser Tyr Met
20 25 30

Leu Trp Tyr Gln Gln Lys Pro Gly Ser Ser Pro Lys Pro Trp Ile Phe
35 40 45

Asp Thr Ser Asn Leu Ala Ser Gly Phe Pro Ala Arg Phe Ser Gly Ser
50 55 60

Gly Ser Gly Thr Ser Tyr Ser Leu Ile Ile Ser Ser Met Glu Ala Glu
65 70 75 80

Asp Ala Ala Thr Tyr Tyr Cys His Gln Arg Ser Gly Tyr Pro Tyr Thr
85 90 95

Phe Gly Gly Gly Thr Lys Leu Glu Ile Lys
100 105

<210> SEQ ID NO 674
<211> LENGTH: 113
<212> TYPE: PRT
<213> ORGANISM: Artificial Sequence
<220> FEATURE:
<223> OTHER INFORMATION: MHC class II binding epitope

<400> SEQUENCE: 674

Glu Val Gln Leu Leu Gln Ser Gly Pro Glu Leu Lys Lys Pro Gly Ala
1 5 10 15

-continued

```
Ser Val Lys Ile Ser Cys Lys Ala Ser Gly Ser Ser Phe Thr Gly Tyr
            20                  25                  30

Asn Met Asn Trp Val Arg Gln Ala Pro Gly Gln Arg Leu Glu Trp Ile
        35                  40                  45

Gly Ala Ile Asp Pro Tyr Tyr Gly Gly Thr Ser Tyr Asn Gln Lys Phe
    50                  55                  60

Lys Gly Arg Ala Thr Leu Ser Val Asp Lys Ser Ser Ser Gln Ala Tyr
65                  70                  75                  80

Met His Leu Lys Ser Leu Thr Ser Glu Asp Ser Ala Val Tyr Tyr Cys
                85                  90                  95

Val Ser Gly Met Glu Tyr Trp Gly Gln Gly Thr Thr Val Thr Val Ser
            100                 105                 110

Ser


<210> SEQ ID NO 675
<211> LENGTH: 113
<212> TYPE: PRT
<213> ORGANISM: Artificial Sequence
<220> FEATURE:
<223> OTHER INFORMATION: MHC class II binding epitope

<400> SEQUENCE: 675

Asp Val Val Met Thr Gln Ser Pro Gly Thr Leu Pro Val Ser Leu Gly
 1               5                  10                  15

Glu Arg Ala Thr Ile Ser Cys Arg Ser Ser Gln Ser Leu Val His Arg
            20                  25                  30

Asn Gly Asn Thr Tyr Leu His Trp Tyr Leu Gln Lys Pro Gly Gln Ser
        35                  40                  45

Pro Lys Leu Leu Ile His Lys Val Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Arg Leu Glu Ala Glu Asp Leu Ala Val Tyr Phe Cys Ser Gln Ser
                85                  90                  95

Thr His Val Pro Pro Leu Thr Phe Gly Gln Gly Thr Lys Leu Glu Ile
            100                 105                 110

Lys


<210> SEQ ID NO 676
<211> LENGTH: 113
<212> TYPE: PRT
<213> ORGANISM: Artificial Sequence
<220> FEATURE:
<223> OTHER INFORMATION: De-immunized MHC class II binding epitope

<400> SEQUENCE: 676

Glu Val Gln Leu Leu Gln Ser Gly Pro Glu Leu Lys Lys Pro Gly Ala
 1               5                  10                  15

Ser Val Lys Ile Ser Cys Lys Ala Ser Gly Ser Ser Phe Thr Gly Tyr
            20                  25                  30

Asn Met Asn Trp Val Arg Gln Ala Ile Gly Gln Arg Leu Glu Trp Ile
        35                  40                  45

Gly Leu Ile Asp Pro Tyr Tyr Gly Gly Thr Ser Tyr Asn Gln Lys Phe
    50                  55                  60

Lys Ser Arg Val Thr Ile Thr Ala Asp Lys Ser Ser Ser Gln Ala Tyr
65                  70                  75                  80
```

-continued

```
Met His Leu Lys Ser Leu Thr Ser Glu Asp Thr Ala Val Tyr Tyr Cys
                85                  90                  95

Val Ser Gly Met Glu Tyr Trp Gly Gln Gly Thr Thr Val Thr Val Ser
            100                 105                 110

Ser
```

<210> SEQ ID NO 677
<211> LENGTH: 113
<212> TYPE: PRT
<213> ORGANISM: Artificial Sequence
<220> FEATURE:
<223> OTHER INFORMATION: De-immunized MHC class II binding epitope

<400> SEQUENCE: 677

```
Asp Val Val Met Thr Gln Ser Pro Gly Thr Leu Pro Val Ser Leu Gly
 1               5                  10                  15

Glu Arg Ala Thr Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Arg Leu Glu Ala Glu Asp Met Ala Val Tyr Phe Cys Ser Gln Ser
                85                  90                  95

Thr His Val Pro Pro Pro Thr Phe Gly Gln Gly Thr Lys Val Glu Ile
            100                 105                 110

Lys
```

<210> SEQ ID NO 678
<211> LENGTH: 113
<212> TYPE: PRT
<213> ORGANISM: Artificial Sequence
<220> FEATURE:
<223> OTHER INFORMATION: De-immunized MHC class II binding epitope

<400> SEQUENCE: 678

```
Glu Val Gln Leu Leu Gln Ser Gly Pro Glu Leu Lys Lys Pro Gly Ala
 1               5                  10                  15

Ser Val Lys Ile Ser Cys Lys Ala Ser Gly Ser Ser Phe Thr Gly Tyr
            20                  25                  30

Asn Met Asn Trp Val Arg Gln Ala Pro Gly Gln Arg Thr Glu Trp Ile
        35                  40                  45

Gly Ala Ile Asp Pro Tyr Tyr Gly Gly Thr Ser Tyr Asn Gln Lys Phe
    50                  55                  60

Lys Ser Arg Val Thr Ile Thr Ala Asp Lys Ser Ser Ser Gln Ala Tyr
65                  70                  75                  80

Met His Leu Lys Ser Leu Thr Ser Glu Asp Thr Ala Val Tyr Tyr Cys
                85                  90                  95

Val Ser Gly Met Glu Tyr Trp Gly Gln Gly Thr Thr Val Thr Val Ser
            100                 105                 110

Ser
```

<210> SEQ ID NO 679
<211> LENGTH: 113
<212> TYPE: PRT
<213> ORGANISM: Artificial Sequence
<220> FEATURE:
<223> OTHER INFORMATION: De-immunized MHC class II binding epitope

<400> SEQUENCE: 679

Asp Val Val Met Thr Gln Ser Pro Gly Thr Leu Pro Val Ser Leu Gly
1 5 10 15

Glu Arg Ala Thr Ile Ser Cys Arg Ser Ser Gln Ser Leu Val His Ser
20 25 30

Asn Gly Asn Thr Tyr Leu His Trp Tyr Leu Gln Lys Pro Gly Gln Ser
35 40 45

Pro Lys Met Leu Ile His Lys Val Ser Asn Arg Phe Ser Gly Val Pro
50 55 60

Asp Arg Phe Ser Gly Ser Gly Ser Gly Thr Asp Phe Thr Leu Thr Ile
65 70 75 80

Ser Arg Leu Glu Ala Glu Asp Met Ala Val Tyr Phe Cys Ser Gln Ser
85 90 95

Thr His Val Pro Pro Pro Thr Phe Gly Gln Gly Thr Lys Val Glu Ile
100 105 110

Lys

<210> SEQ ID NO 680
<211> LENGTH: 113
<212> TYPE: PRT
<213> ORGANISM: Artificial Sequence
<220> FEATURE:
<223> OTHER INFORMATION: De-immunized MHC class II binding epitope

<400> SEQUENCE: 680

Glu Val Gln Leu Leu Gln Ser Gly Pro Glu Leu Lys Lys Pro Gly Ala
1 5 10 15

Ser Val Lys Ile Ser Cys Lys Ala Ser Gly Ser Ser Phe Thr Gly Tyr
20 25 30

Asn Met Asn Trp Val Arg Gln Ala Pro Gly Gln Arg Thr Glu Trp Ile
35 40 45

Gly Ala Ile Asp Pro Tyr Tyr Gly Gly Thr Ser Tyr Asn Gln Lys Phe
50 55 60

Lys Gly Arg Val Thr Ile Thr Ala Asp Lys Ser Ser Ser Gln Ala Tyr
65 70 75 80

Met His Leu Lys Ser Leu Thr Ser Glu Asp Thr Ala Val Tyr Tyr Cys
85 90 95

Val Ser Gly Met Glu Tyr Trp Gly Gln Gly Thr Thr Val Thr Val Ser
100 105 110

Ser

<210> SEQ ID NO 681
<211> LENGTH: 113
<212> TYPE: PRT
<213> ORGANISM: Artificial Sequence
<220> FEATURE:
<223> OTHER INFORMATION: De-immunized MHC class II binding epitope

<400> SEQUENCE: 681

Asp Val Val Met Thr Gln Ser Pro Gly Thr Leu Pro Val Ser Leu Gly
1 5 10 15

Glu Arg Ala Thr Ile Ser Cys Arg Ser Ser Gln Ser Leu Val His Ser
20 25 30

Asn Gly Asn Thr Tyr Leu His Trp Tyr Leu Gln Lys Pro Gly Gln Ser
35 40 45

-continued

```
Pro Lys Met Leu Ile His Lys Val Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Arg Leu Glu Ala Glu Asp Met Ala Val Tyr Phe Cys Ser Gln Ser
                85                  90                  95

Thr His Val Pro Pro Thr Thr Phe Gly Gly Gly Thr Lys Val Glu Ile
            100                 105                 110

Lys


<210> SEQ ID NO 682
<211> LENGTH: 113
<212> TYPE: PRT
<213> ORGANISM: Artificial Sequence
<220> FEATURE:
<223> OTHER INFORMATION: De-immunized MHC class II binding epitope

<400> SEQUENCE: 682

Glu Val Gln Leu Leu Gln Ser Gly Pro Glu Leu Lys Lys Pro Gly Ala
 1               5                  10                  15

Ser Val Lys Ile Ser Cys Lys Ala Ser Gly Ser Ser Phe Thr Gly Tyr
            20                  25                  30

Asn Met Asn Trp Val Arg Gln Ala Pro Gly Gln Arg Thr Glu Trp Ile
        35                  40                  45

Gly Ala Ile Asp Pro Tyr Tyr Gly Gly Thr Ser Tyr Asn Gln Lys Phe
    50                  55                  60

Lys Gly Arg Val Thr Ile Thr Val Asp Lys Ser Ser Ser Gln Ala Tyr
65                  70                  75                  80

Met His Leu Lys Ser Leu Thr Ser Glu Asp Thr Ala Val Tyr Tyr Cys
                85                  90                  95

Val Ser Gly Met Glu Tyr Trp Gly Gln Gly Thr Thr Val Thr Val Ser
            100                 105                 110

Ser


<210> SEQ ID NO 683
<211> LENGTH: 113
<212> TYPE: PRT
<213> ORGANISM: Artificial Sequence
<220> FEATURE:
<223> OTHER INFORMATION: De-immunized MHC class II binding epitope

<400> SEQUENCE: 683

Asp Val Val Met Thr Gln Ser Pro Gly Thr Leu Pro Val Ser Leu Gly
 1               5                  10                  15

Glu Arg Ala Thr Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Met Leu Ile His Lys Val Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Arg Leu Glu Ala Glu Asp Met Ala Val Tyr Phe Cys Ser Gln Ser
                85                  90                  95
```

```
Thr His Val Pro Pro Leu Thr Phe Gly Gly Gly Thr Lys Val Glu Ile
            100                 105                 110

Lys


<210> SEQ ID NO 684
<211> LENGTH: 113
<212> TYPE: PRT
<213> ORGANISM: Artificial Sequence
<220> FEATURE:
<223> OTHER INFORMATION: De-immunized MHC class II binding epitope

<400> SEQUENCE: 684

Glu Val Gln Leu Leu Gln Ser Gly Pro Glu Leu Lys Lys Pro Gly Ala
 1               5                  10                  15

Ser Val Lys Ile Ser Cys Lys Ala Ser Gly Ser Ser Phe Thr Gly Tyr
            20                  25                  30

Asn Met Asn Trp Val Arg Gln Ala Ile Gly Gln Arg Leu Glu Trp Ile
        35                  40                  45

Gly Ala Ile Asp Pro Tyr Tyr Gly Gly Thr Ser Tyr Asn Gln Lys Phe
    50                  55                  60

Lys Gly Arg Val Thr Ile Thr Val Asp Lys Ser Ser Ser Gln Ala Tyr
65                  70                  75                  80

Met His Leu Lys Ser Leu Thr Ser Glu Asp Thr Ala Val Tyr Tyr Cys
                85                  90                  95

Val Ser Gly Met Glu Tyr Trp Gly Gln Gly Thr Thr Val Thr Val Ser
            100                 105                 110

Ser


<210> SEQ ID NO 685
<211> LENGTH: 113
<212> TYPE: PRT
<213> ORGANISM: Artificial Sequence
<220> FEATURE:
<223> OTHER INFORMATION: De-immunized MHC class II binding epitope

<400> SEQUENCE: 685

Asp Val Val Met Thr Gln Ser Pro Gly Thr Leu Pro Val Ser Leu Gly
 1               5                  10                  15

Glu Arg Ala Thr Ile Ser Cys Arg Ser Ser Gln Ser Leu Val His Arg
            20                  25                  30

Asn Gly Asn Thr Tyr Leu His Trp Tyr Leu Gln Lys Pro Gly Gln Ser
        35                  40                  45

Pro Lys Met Leu Ile His Lys Val Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Arg Leu Glu Ala Glu Asp Met Ala Val Tyr Phe Cys Ser Gln Ser
                85                  90                  95

Thr His Val Pro Pro Leu Thr Phe Gly Gly Gly Thr Lys Val Glu Ile
            100                 105                 110

Lys


<210> SEQ ID NO 686
<211> LENGTH: 113
<212> TYPE: PRT
<213> ORGANISM: Artificial Sequence
<220> FEATURE:
<223> OTHER INFORMATION: MHC class II binding epitope
```

-continued

<400> SEQUENCE: 686

```
Glu Val Gln Leu Val Gln Ser Gly Pro Glu Val Glu Lys Pro Ser Ala
 1               5                  10                  15

Ser Val Lys Ile Ser Cys Lys Ala Ser Gly Ser Ser Phe Thr Gly Tyr
            20                  25                  30

Asn Met Asn Trp Val Arg Gln Ala Ile Gly Lys Ser Leu Glu Trp Ile
        35                  40                  45

Gly Ala Ile Asp Pro Tyr Tyr Gly Gly Thr Ser Tyr Asn Gln Lys Phe
    50                  55                  60

Lys Gly Arg Ala Thr Leu Thr Val Asp Lys Ser Ser Ser Thr Ala Tyr
65                  70                  75                  80

Met His Leu Lys Ser Leu Thr Ser Glu Asp Thr Ala Val Tyr Tyr Cys
                85                  90                  95

Val Ser Gly Met Glu Tyr Trp Gly Gln Gly Thr Thr Val Thr Val Ser
            100                 105                 110

Ser
```

<210> SEQ ID NO 687
<211> LENGTH: 113
<212> TYPE: PRT
<213> ORGANISM: Artificial Sequence
<220> FEATURE:
<223> OTHER INFORMATION: MHC class II binding epitope

<400> SEQUENCE: 687

```
Asp Val Val Met Thr Gln Thr Pro Gly Ser Leu Pro Val Ser Ala Gly
 1               5                  10                  15

Asp Gln Ala Ser Ile Ser Cys Arg Ser Ser Gln Ser Leu Val His Arg
            20                  25                  30

Asn Gly Asn Thr Tyr Leu His Trp Tyr Leu Gln Lys Pro Gly Gln Ser
        35                  40                  45

Pro Lys Leu Leu Ile His Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Ser Gly Val Tyr Phe Cys Ser Gln Ser
                85                  90                  95

Thr His Val Pro Pro Leu Thr Phe Gly Ala Gly Thr Lys Leu Glu Leu
            100                 105                 110

Lys
```

<210> SEQ ID NO 688
<211> LENGTH: 113
<212> TYPE: PRT
<213> ORGANISM: Mus Musculus

<400> SEQUENCE: 688

```
Glu Val Gln Leu Leu Gln Ser Gly Pro Glu Leu Glu Lys Pro Ser Ala
 1               5                  10                  15

Ser Val Met Ile Ser Cys Lys Ala Ser Gly Ser Ser Phe Thr Gly Tyr
            20                  25                  30

Asn Met Asn Trp Val Arg Gln Asn Ile Gly Lys Ser Leu Glu Trp Ile
        35                  40                  45

Gly Ala Ile Asp Pro Tyr Tyr Gly Gly Thr Ser Tyr Asn Gln Lys Phe
    50                  55                  60
```

-continued

```
Lys Gly Arg Ala Thr Leu Thr Val Asp Lys Ser Ser Ser Thr Ala Tyr
65                  70                  75                  80

Met His Leu Lys Ser Leu Thr Ser Glu Asp Ser Ala Val Tyr Tyr Cys
                85                  90                  95

Val Ser Gly Met Glu Tyr Trp Gly Gln Gly Thr Ser Val Thr Val Ser
            100                 105                 110

Ser


<210> SEQ ID NO 689
<211> LENGTH: 113
<212> TYPE: PRT
<213> ORGANISM: Mus Musculus

<400> SEQUENCE: 689

Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Arg
            20                  25                  30

Asn Gly Asn Thr Tyr Leu His Trp Tyr Leu Gln Lys Pro Gly Gln Ser
        35                  40                  45

Pro Lys Leu Leu Ile His Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Leu Thr Phe Gly Ala Gly Thr Lys Leu Glu Leu
            100                 105                 110

Lys
```

ARTIFICIAL PROTEINS WITH REDUCED IMMUNOGENICITY

This application is a division of U.S. application patent Ser. No. 10/468,370, filed on Aug. 19, 2003, now U.S. Pat. No. 7,189,830, which is the National Stage of International Application No. PCT/EP02/01690, filed on Feb. 18, 2002, each of which is incorporated herein by reference.

TECHNICAL FIELD OF THE INVENTION

The invention relates to modified artificial proteins, preferably fusion proteins, having a reduced immunogenicity compared to the parent non-modified molecule when exposed to a species in vivo. Especially, the invention relates to proteins that are as single component normally not strongly immunogenic, but which have enhanced immunogenicity when attached to a second protein moiety to form an, as a rule, artificial fusion protein. The invention relates, above all, to modified and, thus, novel immunoglobulin (Ig) fusion proteins which essentially consist of an immunoglobulin molecule or a fragment thereof covalently fused via its C-terminus to the N-terminus of a biologically active non-immunoglobulin molecule, preferably a polypeptide or protein or a biologically active fragment thereof. In a specific embodiment, the invention relates to fusion proteins consisting of an Fc portion of an antibody which is fused as mentioned to the non-immunological target molecule which elicits biological or pharmacological efficacy.

The molecules of the invention have amino acid sequences which are altered in one or more amino acid residue positions but have in principal the same biological activity as compared with the non-altered molecules. The changes are made in regions of the molecules which are identified as T-cell epitopes, which contribute to an immune reaction in a living host. Thus, the invention also relates to a novel method for preparing said fusion proteins by identifying said epitopes comprising calculation of T-cell epitope values for MHC Class II molecule binding sites in a peptide by computer-aided methods.

BACKGROUND OF THE INVENTION

Therapeutic fusion proteins are, as a rule, artificial molecules, which are produced to combine known favorable properties of the single components or to create new properties. For example, a fusion protein may contain an immunogenic moiety that causes a normally non-immunogenic fusion partner to become immunogenic. In other cases, each of the components are immunogenic and the fusion molecule has kept this usually undesired property. Finally, it is possible that fusing non or less immunogenic components the fusion product is immunogenic by creating the bonds, especially the junction region.

Fusion proteins of specific interests in this context are immunoconjugates. Immunoconjugates are known since a couple of years and many of them have shown pharmacological efficacy in vitro and in vivo. Immunoconjugates are chimeric molecules consisting, as a rule, of a portion deriving from an immunoglobulin or a fragment thereof and a target polypeptide or protein which is linked to the immunoglobulin molecule. Originally, immunoconjugates were prepared consisting of a complete antibody and a cytotoxic agent like a cytokine which was fused via its N-terminus to the C-terminus of the constant domain of the immunoglobulin, or alternatively, via its C-terminus to the N-terminus of the variable region of the antibody (see, for example EP 0439 095, WO 92/08495, U.S. Pat. No. 5,349,053, EP 0659 439, EP 0706 799). These chimeric molecules are bi-functional by targeting a specific antigen, for example, on a tumor cell surface by means of the binding sites within the CDRs of the variable domain of the antibody portion or a fragment thereof, and by the simultaneous cytotoxic effect of the cytokine which is coupled to the immunoglobulin and thus can, theoretically, only or predominantly attack the targeted cell. In this context, also tri- and multi-functional immunoconjugates were developed including constructs consisting of sFv-, Fab-, Fab' or F(ab')2 fragments of different antibodies, wherein in each case the targeting function of the immunoglobulin portion was advantageously used.

Another immunoglobulin modification is the use of the Fc region of antibodies. Antibodies comprise two functionally independent parts, a variable domain known as "Fab", "Fab", "F(ab')2", dependent on the kind of digestion of the molecule, which bind antigen, and a constant domain, known as "Fc" which provides the link to effector functions such as complement or phagocytic cells. The Fc portion of an immunoglobulin has a long plasma half-life, whereas the Fab fragments are short-lived (Capon, et al., Nature 337: 525-531 (1989)).

Therapeutic protein products have been constructed using the Fc domain to provide longer half-life or to incorporate functions such as Fc receptor binding, protein A binding, complement fixation and placental transfer which all reside in the Fc proteins of immunoglobulins. For example, the Fc region of an IgG1 antibody has been fused to the N-terminal end of CD30-L, a molecule which binds CD30 receptors expressed on Hodgkin's Disease tumor cells, anaplastic lymphoma cells, T-cell leukemia cells and other malignant cell types (U.S. Pat. No. 5,480,981). IL-10, an anti-inflammatory and antirejection agent has been fused to murine Fcγ2a in order to increase the cytokine's short circulating half-life (Zheng et al., The Journal of Immunology, 154: 5590-5600 (1995)). Studies have also evaluated the use of tumor necrosis factor receptor linked with the Fc protein of human IgG1 to treat patients with septic shock (Fisher et al., N. Engl. J. Med., 334:1697-1702 (1996); Van Zee et al., The Journal of Immunology, 156:2221-2230 (1996)). Fc has also been fused with CD4 receptor to produce a therapeutic protein for treatment of AIDS (see: Capon et al., Nature, 337:525-531 (1989)). Principally, Fc can be fused to the target protein or peptide via its C- or N-terminus using the N- and C-terminus of the protein, respectively. A chimer of Fc and TNF and EPO was disclosed in EP 0464 533 (Hoechst/General Hospital), wherein the N-terminus of Fc was coupled to the C-terminus of the protein (X-Fc). The identical conjunction was selected for leptin-Fc chimers disclosed in WO 97/00319 (SKB) and WO 97/24440 (Genentech). There are a lot of publications and patent applications describing the opposite linkage of Fc-protein chimers (Fc-X), such as Fc-(IL-2), Fc-EPO, Fc-PSMA, Fc-(IL-12), Fc-TNFa, Fc-(GM-CSF), Fc-TNFR, Fc-endostatin, Fc, angiostatin, Fc-gp120, Fc-leptin, Fc-IFNa, Fc-(G-CSF). Examples are WO 96/08570, (Fuji/Merck KGaA), WO 98/28427 (Amgen), WO 99/02709 (Beth Israel Medical Care Center) and WO 99/58662 (Fuji/Merck KGaA). WO 00/24782 (Amgen) discloses a huge number of possible Fc-X conjugates, wherein the linkage between the two partners may be Fc-X or X-Fc. An extensive development of Fc-X molecules was realized by Lexigen/Merck KgaA as disclosed in U.S. Pat. No. 5,541,087, WO 99/43713, WO 99/29732, WO 99/52562, WO 99/53958, WO 00/11033, WO 01/07081, PCT/EP00/10843. Thus, X-Fc and Fc-X molecules which have "lost" their antigen binding sites, as well as molecules, wherein the binding sites und thus their antigen-specific targeting functions are conserved, are of great interest as promising therapeutic proteins and there exists a further need to develop analogue compositions for different clinical application.

Non-natural therapeutic proteins are often particularly immunogenic. For example, Enbrel is a fusion protein consisting of an extracellular domain of a Tumor Necrosis Factor Receptor (TNF-R) fused to an Fc region of an antibody. About 16% of patients treated with Enbrel have been reported to develop antibodies to this fusion protein (*Physician's Desk Reference [*2001] p. 3372). Similarly, a fusion protein consisting of erythropoietin (Epo) and granulocyte/macrophage-colony stimulating factor (GMCSF) was found to be highly immunogenic (Coscarella A, et al., [1998] Cytokine 10:964-9; Coscarella A, Mol Biotechnol. [1998] 10:115-22). When injected into a primate, Epo-GMCSF fusion proteins were found to induce a strong antibody response to the Epo moiety of the fusion protein, resulting in anemia. Ceredase™ and Cerezyme™ are forms of the lysosomal enzyme glucocerebrosidase used to treat Gaucher's disease; as a result of genetic engineering, glucocerebrosidase is attached to an unusual high-mannose glycosylation. Patients with Gaucher's disease lack glucocerebrosidase in their lysosomes, and as a result the patients' macrophages tend to accumulate lipids and become foam cells (*The Metabolic and Molecular Bases of Inherited Disease,* 8$^{th}$ Edition [2001] Scriver et al., eds., Chapter 146, "Gaucher Disease," p. 3635-3668). After administration of Ceredase™ or Cerezyme™, the therapeutic protein is bound by mannose receptors on macrophages, endocytosed, and trafficked through the endosomes to the lysosome, which is its proper location. Patients treated with Ceredase often develop antibodies to glucocerebrosidase (Pastores G M, et al., Blood [1993] 82:408-16*; Physicians' Desk Reference [*2001] p. 1325-1326). Such antibodies can interfere with treatment (Brady R O, et al., Pediatrics [1997] 100(6):E11.). In a Phase I clinical trial using an antibody-cytokine fusion protein, several patients developed antibody responses to the therapeutic fusion protein. In this case, the antibody moiety was a humanized form of the 14.18 antibody, and the cytokine was interleukin-2 (IL-2). Many of the reactive patients' sera included significant levels of anti-idiotype antibodies.

Therapeutic use of a number of peptides, polypeptides and proteins is curtailed because of their immunogenicity in mammals, especially humans. For example, when murine antibodies are administered to patients who are not immunosuppressed, a majority of such patients exhibit an immune reaction to the introduced foreign material by making human anti-murine antibodies (HAMA) (e.g. Schroff, R. W. et al., *Cancer Res.* 45:879-885 (1985); Shawler, D. L. et al., *J. Immunol.* 135:1530-1535 (1985)). There are two serious consequences. First, the patient's anti-murine antibody may bind and clear the therapeutic antibody or immunoconjugate before it has a chance to bind, for example to a tumor, and perform its therapeutic function. Second, the patient may develop an allergic sensitivity to the murine antibody and be at risk of anaphylactic shock upon any future exposure to murine immunoglobulin.

Several techniques have been employed to address the HAMA problem and thus enable the use in humans of therapeutic monoclonal antibodies (see, for example, WO89/09622, EP0239400, EP0438310, WO91/09967). These recombinant DNA approaches have generally reduced the mouse genetic information in the final antibody construct whilst increasing the human genetic information in the final construct. Notwithstanding, the resultant "humanized" antibodies have, in several cases, still elicited an immune response in patients (Issacs, J. D., *Sem. Immunol.* 2:449, 456 (1990); Rebello, P. R. et al., *Transplantation* 68:1417-1420 (1999)).

A common aspect of these methodologies has been the introduction into the therapeutic antibody, usually of rodent origin, of amino acid residues, even significant tracts of amino acid residue sequences, identical to those present in human antibody proteins. For antibodies, this process is possible owing to the relatively high degree of structural (and functional) conservatism among antibody molecules of different species. For potentially therapeutic peptides, polypeptides and proteins, however, where no structural homologue may exist in the host species (e.g., human) for the therapeutic protein, such processes are not applicable.

Furthermore, these methods have assumed that the general introduction of a human amino acid residue sequence will render the re-modeled antibody non-immunogenic. It is known, however, that certain short peptide sequences ("T-cell epitopes") can be released during the degradation of peptides, polypeptides or proteins within cells and subsequently be presented by molecules of the major histocompatability complex (MHC) in order to trigger the activation of T-cells. For peptides presented by MHC Class II, such activation of T-cells can then give rise to an antibody response by direct stimulation of B-cells to produce such antibodies. Accordingly, it would be desirable to eliminate potential T-cell epitopes from a peptide, polypeptide or a protein. Even proteins of human origin and with the same amino acid sequences as occur within humans can still induce an immune response in humans. Notable examples include therapeutic use of granulocyte-macrophage colony stimulating factor (Wadhwa, M. et al., Clin. Cancer Res. 5:1353-1361 (1999)) and interferon alpha 2 (Russo, D. et al., *Bri. J. Haem.* 94:300-305 (1996); Stein, R. et al., *New Engl. J. Med.* 318:1409-1413 (1988)).

During the last couple of years several techniques were published which suggest solutions for rendering antibodies and target proteins having different biological functions non- or at least less immunogenic. Examples are: WO 92/10755 and WO 96/40792 (Novo Nordisk), EP 0519 596 (Merck & Co.), EP 0699 755(Centro de Immunologia Moelcular), WO 98/52976 and WO 98/59244 and WO 00/34317 (Biovation Ltd.).

The general methods disclosed in the prior art and regarding the elimination of T-cell epitopes from proteins (e.g. WO 98/52976, WO 00/34317) comprise the following steps:

(a) Determining the amino acid sequence of the polypeptide or part thereof (b) Identifying one or more potential T-cell epitopes within the amino acid sequence of the protein by any method including determination of the binding of the peptides to MHC molecules using in vitro or in silico techniques or biological assays.

(c) Designing new sequence variants with one or more amino acids within the identified potential T-cell epitopes modified in such a way to substantially reduce or eliminate the activity of the T-cell epitope as determined by the binding of the peptides to MHC molecules using in vitro or in silico techniques or biological assays. Such sequence variants are created in such a way to avoid creation of new potential T-cell epitopes by the sequence variations unless such new potential T-cell epitopes are, in turn, modified in such a way to substantially reduce or eliminate the activity of the T-cell epitope.

(d) Constructing such sequence variants by recombinant DNA techniques and testing said variants in order to identify one or more variants with desirable properties.

Other techniques exploiting soluble complexes of recombinant MHC molecules in combination with synthetic peptides and able to bind to T-cell clones from peripheral blood samples from human or experimental animal subjects have been used in the art [Kern, F. et al., *Nature Medicine* 4:975-978 (1998); Kwok, W. W. et al., *TRENDS in Immunology* 22:583-588 (2001)] and may also be exploited in an epitope identification strategy.

The potential T-cell epitopes are generally defined as any amino acid residue sequence with the ability to bind to MHC Class II molecules. Such potential T-cell epitopes can be measured to establish MHC binding. In the general understanding the term "T-cell epitope" is an epitope which when bound to MHC molecules can be recognized by the T-cell receptor, and which can, at least in principle, cause the activation of these T-cells. It is, however, usually understood that certain peptides which are found to bind to MHC Class II molecules may be retained in a protein sequence because such peptides are tolerated by the immune within the organism into which the final protein is administered.

The invention is conceived to overcome the practical reality that soluble proteins introduced into an autologous host with therapeutic intent, can trigger an immune response resulting in development of host antibodies that bind to the soluble protein. One example amongst others is interferon alpha 2 to which a proportion of human patients make antibodies despite the fact that this protein is produced endogenously [Russo, D. et al., *Brit. J. Haem.* 94:300-305 (1996); Stein, R. et al., *New Engl. J. Med.* 318:1409-1413 (1988)].

MHC Class II molecules are a group of highly polymorphic proteins which play a central role in helper T-cell selection and activation. The human leukocyte antigen group DR (HLA-DR) are the predominant isotype of this group of proteins and the major focus of the present invention. However, isotypes HLA-DQ and HLA-DP perform similar functions, hence the present invention is equally applicable to these. MHC HLA-DR molecules are homo-dimers where each "half" is a hetero-dimer consisting of α and β chains. Each hetero-dimer possesses a ligand binding domain which binds to peptides varying between 9 and 20 amino acids in length, although the binding groove can accommodate a maximum of 9-11 amino acids. The ligand binding domain is comprised of amino acids 1 to 85 of the α chain, and amino acids 1 to 94 of the β chain. DQ molecules have recently been shown to have an homologous structure and the DP family proteins are also expected to be very similar. In humans approximately 70 different allotypes of the DR isotype are known, for DQ there are 30 different allotypes and for DP 47 different allotypes are known. Each individual bears two to four DR alleles, two DQ and two DP alleles. The structure of a number of DR molecules has been solved and such structures point to an open-ended peptide binding groove with a number of hydrophobic pockets which engage hydrophobic residues (pocket residues) of the peptide [Brown et al., *Nature* 364:33 (1993); Stem et al., *Nature* 368:215 (1994)].

Polymorphism identifying the different allotypes of class II molecule contributes to a wide diversity of different binding surfaces for peptides within the peptide binding grove and at the population level ensures maximal flexibility with regard to the ability to recognize foreign proteins and mount an immune response to pathogenic organisms.

There is a considerable amount of polymorphism within the ligand binding domain with distinct "families" within different geographical populations and ethnic groups. This polymorphism affects the binding characteristics of the peptide binding domain, thus different "families" of DR molecules will have specificities for peptides with different sequence properties, although there may be some overlap. This specificity determines recognition of Th-cell epitopes (Class II T-cell response) which are ultimately responsible for driving the antibody response to B-cell epitopes present on the same protein from which the Th-cell epitope is derived. Thus, the immune response to a protein in an individual is heavily influenced by T-cell epitope recognition which is a function of the peptide binding specificity of that individual's HLA-DR allotype. Therefore, in order to identify T-cell epitopes within a protein or peptide in the context of a global population, it is desirable to consider the binding properties of as diverse a set of HLA-DR allotypes as possible, thus covering as high a percentage of the world population as possible.

A principal factor in the induction of an immune response is the presence within the protein of peptides that can stimulate the activity of T-cell via presentation on MHC class II molecules. In order to eliminate or reduce immunogenicity, it is thus desirable to identify and remove T-cell epitopes from the protein.

According to the above-cited methods and related processes several biological molecules, basically usual target proteins and antibodies have been prepared which reveal reduced immunogenicity and allergenicity. Examples are: WO 99/55369 (SKB), WO 99/40198 and WO 96/21016 (Leuven Research & Development VZW), WO 00/08196 (Duke University), WO 96/21036 (Chiron Viragen), WO 97/31025 (Chiron Corp.), WO 98/30706 (Alliance Pharmaceutical Corp.).

In all these applications cited above single proteins or antibodies eliciting a lower immune response were disclosed; there is no hint that fusion proteins, above all immunoglobulin fusion proteins were completely or partially de-immunized, especially by reducing the number of T-cell epitopes within the sequence of said molecules by means of partially computational methods. In WO 97/24137 (Tannox Biosystems Inc.) a IFNα-Fc chimer is disclosed which contains a non-immunogenic linker molecule between the N-terminus of the Fc portion and the C-terminus of IFNα.

Therefore, it is still a need to provide for biological molecules, such as immunoconjugates, which are not or less immunogenic. Above all, it is of specific interest to provide for Fc-conjugates, preferably Fc-X chimers, wherein X is a selected protein or polypeptide of therapeutic interest.

SUMMARY OF THE INVENTION

The present invention relates to four general aspects:

(a) a novel application of the details of the immune response mechanism to situations involving fusion proteins and other artificial proteins, to help determine when an engineered or novel protein is likely to be immunogenic and therefore when application of a deimmunization methodology is appropriate, (b) novel biologically active artificial proteins to be administered especially to humans and in particular for therapeutic use, (c) a method of designing improved, less immunogenic artificial proteins that normally have enhanced immunogenicity, the method comprising identification of one or more candidate T-cell epitopes in the artificial protein and introducing a mutation that removes one or more T-cell epitopes, and (d) a convenient and effective computational method for the identification and calculation of T-cell epitopes for a globally diverse number of MHC Class II molecules and, based on this knowledge, for designing and constructing new sequence variants of biological molecules with improved properties. Once T-cell epitopes have been identified in an artificial protein, they are removed by mutation as described in (c).

Artificial proteins that have a component capable of binding to a surface receptor on a cell of the immune system are, in general, particularly immunogenic. Artificial proteins that are immunogenic as a consequence of having a moiety that binds to an immune cell surface receptor are particularly good candidates for the methods of the invention for reducing immunogenicity.

Without wishing to be bound by theory, FIGS. 1-6 present diagrams of artificial proteins containing moieties that bind to immune cell surface receptors such as an Fc receptor, a cytokine receptor, or an oligosaccharide receptor.

One method of the invention consists of the steps of identifying artificial proteins that contain moieties that bind to an immune cell surface receptor, which may be done by sequence inspection, identifying candidate T-cell epitopes in the artificial protein, designing mutant derivatives of the artificial protein in which the number of T-cell epitopes is reduced, producing one or more mutant derivatives, testing the mutant derivatives for activity and optionally other desired properties, and choosing a mutant derivative that has an optimal balance of reduced T-cell epitopes, retained activity, and optionally other retained desired properties. Other desired properties may include, but are not limited to, pharmacokinetic properties and protein expression and assembly characteristics.

Artificial proteins that tend to form aggregates are a second category of proteins that can be improved by the methods of the invention.

One class of artificial proteins that can particularly be improved by the invention are Ig fusion proteins, such as fusion proteins comprising an entire antibody, as well as Fc-X and X-Fc fusion proteins. In particular, immunoglobulin fusion proteins comprising a functional Fc receptor binding site can be particularly improved by methods of the invention.

The invention provides improved forms of such antibody fusion proteins, which include fusion proteins comprising V regions that recognize tumor-specific antigens, other tissue-specific antigens, or other disease-specific antigens. In one preferred embodiment, each of these antibodies is fused to a cytokine, such as IL-2.

For example, the invention provides fusion proteins comprising the tumor-directed anti-EpCAM antibody KS 1/4 and anti-GD2 antibody 14.18, in which the V regions of the antibody contain mutations that remove T-cell epitopes.

In a distinct embodiment, the moiety that is fused to the antibody moiety is mutated such that T-cell epitopes are removed. For example, the invention discloses an antibody-IL-2 fusion protein in which the IL-2 moiety has been altered to remove T-cell epitopes.

A second general class of Ig fusion proteins that can be significantly improved are the Fc-X and X-Fc fusion proteins. Without wishing to be bound by theory, it is thought that these proteins are particularly immunogenic because the Fc receptor binding site, which is normally somewhat sterically blocked by the light chain in an intact antibody, is exposed. In any case, it has been empirically established that an Fc fusion protein can be more immunogenic than the fusion partner by itself (WO 01/07081).

Another class of immunogenic fusion proteins are proteins that are fused to a cytokine. Without wishing to be bound by theory, it may be that these proteins are particularly immunogenic because when the fusion partner protein binds to an immune cell, for example a cell bearing an antibody that recognizes the fusion partner protein, the cytokine stimulates the cell in some way (see FIG. 4).

A class of artificial proteins that are particularly immunogenic are normal proteins that contain an inappropriate oligosaccharide. For example, a protein containing an oligosaccharide that is bound by a specific receptor on an immune cell is often found to be immunogenic. For example, a protein, preferably a protein such as beta-glucocerebrosidase that can be used to treat a lysosomal storage disorder, contains a high mannose oligosaccharide. Such an immunogenic protein shows significantly reduced immunogenicity when modified according to the invention.

The invention provides less immunogenic forms of the following protein moieties that are incorporated into otherwise immunogenic fusion proteins such as: erythropoietin, leptin, keratinocyte growth factor, G-CSF GM-CSF, IL-1R antagonist, sTNFR, TNF inhibitor, sTNFR-Fc (Enbrel®), BNTF, CNTF, members of the interferon family, hGH, β-glucocerebrosidase. All these biologically active protein moieties listed above derive from well known non-modified (parent) protein moieties according to the invention.

The modified proteins according to the invention may be produced by the method indicated in Section "Detailed Description of the Invention". The method includes a novel method for identification T-cell epitopes by computational means. This method step is preferred according to the invention and described in more detail in EXAMPLE 1.

The invention discloses and claims as preferred embodiments of the invention altered or modified fusion proteins derived from parent fusion proteins, said parent fusion protein essentially consisting of an immunoglobulin molecule or a fragment thereof and a non-immunoglobulin target polypeptide (X), which is linked preferably by its N-terminal to the C-terminal of the immunoglobulin molecule or a fragment thereof, wherein the altered fusion protein has an amino acid sequence different from that of said parent fusion protein and exhibits reduced immunogenicity relative to the parent fusion protein when exposed to the immune system of a given species, that is preferably human.

The strategies that are used in practice according to the invention to reduce the immunogenicity of an immunogenic fusion protein are illustrated in detail for the antibody-cytokine fusions. These general strategies include:

Examining the amino acid sequences in the fusion protein and prioritizing them with respect to likely immunogenicity, based on the expected presence and abundance of the sequences during negative selection of T-cells in the thymus. For example, completely non-self epitopes are identified, and are the highest priority for removal of T-cell epitopes by mutation. The lowest priority for removal of T-cell epitopes are sequences that are present in abundant serum proteins, such as antibody constant regions or sequences that are found in un-rearranged antibody V regions. An intermediate priority for removal of T-cell epitopes by mutation are self sequences that are found in low abundance proteins, such as cytokines. Without wishing to be bound by theory, it is expected that low abundance proteins may not be present in the thymus in high enough amounts to promote negative T-cell selection, and may thus be recognized as non-self T-cell epitopes.

When a region is chosen for removal of T-cell epitopes by mutation, it is compared with naturally occurring human sequences found in abundant proteins. Mutations are introduced to make any non-self sequences more similar to self sequences. For example, to reduce the immunogenicity of a mouse V region, the sequence is compared to un-rearranged human V regions and the most closely related sequence is found. "Veneering" changes are introduced, in which some amino acids are converted from mouse to human. This has the effect of converting some non-self T-cell epitopes into self T-cell epitopes, a method for reducing immunogenicity disclosed by U.S. Pat. No. 5,712,120, and also has the effect of removing some B cell epitopes. However, it is still necessary to remove T-cell epitopes that derive from hypervariable region sequences.

To remove most or all of the remaining T-cell epitopes, mutations are introduced that, by the computer-based criteria defined above, prevent binding of a peptide into a groove of an MHC Class II molecule. In the case of antibody V regions, it is preferable to introduce mutations that lie outside the CDRs themselves, to avoid interfering with antigen binding.

In the case of fusion proteins of any type, it is generally the case that the fusion junction will contain non-self T-cell epitopes. These T-cell epitopes may be also removed by mutation.

As a specific embodiment the invention includes chimeric immunoglobulins or fragments thereof wherein the reduced immunogenicity, the reduced number of T-cell epitopes or the reduced number of peptides binding to MHC class II molecules is located to the target polypeptide portion X as well as to the immunoglobulin portion or fragments thereof of the altered fusion protein.

The invention includes also chimeric immunoglobulins as defined according to the invention wherein the immunoglobulin molecule and the non-immunoglobulin target polypeptide (X) are fused via a linker molecule (L). As a specific embodiment of the invention this linker molecule itself has no or lower immunogenicity. Thus, the invention may include immunoconjugates, wherein the linker molecule alone is de-immunized. Linker molecules which have reduced or no immunogenicity are known in the art or can be prepared by known methods or by the method according to the invention. The invention also includes such immunoglobulin fusion proteins, wherein the immunoglobulin portion as well as the target protein (X) portion of the fusion molecule and optionally the linker molecule and the junction region (see below) are immunogenicly modified. Alternatively, only one or more but not all portions of the molecule are modified according to the invention.

The invention relates, furthermore, to above-said immunoconjugates which may derive, in principal, from all immunoglobulin classes; however IgG is preferred. It is an object of the invention to provide such chimeric immunoglobulins which derive from IgG1, IgG2, IgG3 and IgG4. IgG1 and IgG2 immunoglobulins are preferred; IgG2 immunoglobulins are most preferred.

Since it has been shown that even recombinant proteins of human origin and humanized antibodies may elicit an undesirable immune response in humans it is object of this invention to provide fusion proteins wherein the immunoglobulin portion as well as the target polypeptide portion (X) may be selected from non-human as well as from human origin. Since humanized or human-derived molecules have, as a rule, a less number of T-cell epitopes, such molecules are preferred for de-immunization, because a less number of amino acid residues has to be modified.

Immunoconjugates (immunoglobulin (Ig) fusion proteins) according to the invention include also fragments of antibodies like sFv, Fab, Fab', F(ab')2 and Fc. It is a specific and preferred object of the invention to provide said above- and below-defined fusion proteins, wherein the immunoglobulin portion is a Fc domain of an antibody, preferably an IgG1 or IgG2 antibody. Fc-X molecules according to the invention which have reduced affinity to Fc receptors are a preferred object of the invention. Fc molecules having a reduced affinity to Fc receptors are well known in the art and can be prepared by modifying the amino acid sequence of the Fc domain (e.g. WO 99/43713).

In detail, the invention refers to:

an immunogenicly modified fusion protein derived from a parent fusion protein, essentially consisting of a first protein/polypeptide and a second protein/polypeptide, wherein the first protein is an immunoglobulin molecule or a fragment thereof and the second protein/polypeptide is non-immunoglobulin target polypeptide (X) each linked to the other directly or by a linker molecule; said modified fusion protein having an amino acid sequence different from that of said parent fusion protein and exhibiting reduced immunogenicity by a reduced number of T-cell epitopes within its amino acid sequence relative to the parent fusion protein when exposed to the immune system of a given species;

a corresponding fusion protein, wherein said T-cell epitopes are peptide sequences able to bind to MCH class II molecule binding groups;

a corresponding fusion protein, wherein the target polypeptide (X) is linked by its N-terminal to the C-terminal of the immunoglobulin moiety;

a correspondingly modified fusion protein, wherein the given species is a human;

a corresponding fusion protein, wherein the fusion components are fused via a linker molecule L;

a modified fusion protein according to claim 4, wherein said linker molecule L is non-immunogenic or less immunogenic;

a corresponding fusion protein, wherein the junction region represented by the C-terminal region of the immunoglobulin portion and the N-terminal region of the non-immunoglobulin target polypeptide (X) has no or a reduced number of T-cell epitopes;

a corresponding fusion protein, wherein the immunoglobulin portion or a fragment thereof or the target polypeptide (X) portion is less immunogenic;

a corresponding fusion protein, wherein said immunoglobulin molecule or fragment thereof is IgG1 or IgG2;

a corresponding fusion protein, wherein said immunoglobulin fragment is a Fc portion, wherein, preferably, said Fc portion has a reduced affinity to Fc receptors;

an immunogenicly modified fusion protein according having the formula $$Fc\text{-}L_n\text{-}X$$

wherein

Fc is the Fc portion of an immunoglobulin molecule (antibody),

X is a non-immunoglobulin target polypeptide

L is a linker peptide, n=0 or 1, and wherein X and/or L comprises amino acid residue modifications which elicit a reduced immunogenicity compared to the parent molecule.

Preferred embodiments of these immunogenicly modified Fc fusion molecules are:

Fc-$X^m$, wherein X is modified only,

Fc-$L^m$-$X^m$, wherein X and L are modified to have a reduced immunogenicity,

Fc-$X^m$, wherein X and the junction region between Fc and X are modified,

Fc-$L^m$-$X^m$, wherein X and L and the junction regions between Fc, X and L are modified;

a corresponding Fc-(L)-X fusion protein wherein at least X is immunogenicly modified;

an immunogenicly modified fusion protein having the formula

A-$L_n$-X wherein

A is a whole antibody or its sFv, Fab, Fab', F(ab')$_2$ fragments

X is a non-immunoglobulin target polypeptide

L is a linker peptide, n=0 or 1, and wherein A and/or X and/or L comprise amino acid residue modifications which elicit a reduced immunogenicity compared to the parent molecule;

Preferred embodiments of these immunogenicly modified fusion molecules are:

A-$X^m$, wherein X is modified only, optionally the A-X junction region, $A^m$-$X^m$, wherein A and X are modified, optionally their junction region, A-$L^m$-$X^m$, wherein X and L are modified only to have a reduced immunogenicity, $A^m$-X, wherein A has reduced immunogenicity only, optionally the A-X junction region, $A^m$-$L^m$-$X^m$, wherein A, L and X are immunogenicly modified, optionally the A-L-X junction regions;

a corresponding A-(L)-X fusion molecule, wherein at least X or A is immunogenicly modified;

a corresponding fusion protein, wherein A is selected from the group:

anti-EGF receptor (HER1) antibodies anti-HER2 antibodies anti-CDx antibodies, wherein x is an integer from 1 -25 anti-cytokine receptor antibodies anti-17-1A antibodies, anti-KSA antibodies anti-GP IIb/IIIa antibodies anti-integrin receptor antibodies anti-VEGF receptor antibodies;

a correspondingly fusion protein, wherein the antibody is selected from the group:

monoclonal antibody 225 and derivatives, monoclonal antibody 425 and derivatives monoclonal antibody KS 1/4 and derivatives monoclonal antibody 14.18 and derivatives monoclonal antibody 4D5/HER2 (Herceptin®) and derivatives monoclonal antibody 17-1A and derivatives monoclonal anti-CD3 antibodies monoclonal antibody 7E3 and derivatives monoclonal antibodies LM609, P1F6 and 14D9.F8 and derivatives monoclonal antibody DC-101 and derivatives monoclonal anti-IL-2R antibody (Zenapax®) and derivatives a corresponding fusion protein, wherein the target polypeptide X is selected from the group:

cytokines, integrin inhibitors, soluble cytokine receptors, glycoproteins, hormones, glycoprotein hormones, leptin, growth hormones, growth factors, antihemophilic factors, antigens, cytokine receptor antagonists;

a corresponding fusion protein, wherein the target polypeptide X is selected from the group:

IL-2, G-CSF, GM-CSF, EPO, TPO, members of the interferon family, TNFα, soluble TNF receptor, IL-12, IL-8, factor VIII, FGF, TGF, EGF, VEGF, PMSA, IGF, insulin, RGD-peptides, endostatin, angiostatin, BDNF, CNTF, protein c, factor VIII and IX, and and biologically active fragments thereof;

a more specidied corresponding fusion protein selected from the group:

MAb KS 1/4-IL2, MAb 14.18-IL2

MAb 425-IL2, MAb c425-IL2, MAb h425-IL2, MAb 425-TNFa

MAb 225-IL2, MAb c225-IL2

MAb 4D5-IL2, MAb DC101-Il2, MAb LM609-IL2,

Fc-IL2, Fc-TNFa, Fc-G-CSF, Fc-EPO, Fc-Leptin, Fc-KGF,

Fc-BFNF, FC-β-Cerebrosidase, Fc-TPO, Fc-GM-CSF;

an immunogenicly modified artificial protein selected from the group:

(i) Y-(L)-X, wherein Y is a cytokine and X, (L) is a molecule as defined above, (ii) P-(L)-X, wherein P is a protein with unusual glycosylation moieties and X, (L) is a molecule as defined above, (iii) A-(L)-X, wherein A, X (L) is a molecule as defined above, derived from a parent artificial protein having an amino acid sequence which is different from that of said parent artificial protein and exhibits reduced immunogenicity by a reduced number of T-cell epitopes relative to the parent fusion protein when exposed to the immune system of a given species, wherein said T-cell epitopes are peptide sequences able to bind to MCH class II molecule binding groups obtainable or obtained by a method as specified in this invention;

a DNA sequence encoding any fusion protein as specified above and below;

a DNA sequence encoding a corresponding fusion protein, comprising (i) a signal sequence (ii) a DNA sequence encoding all domains or a Fc, sFV, Fab, Fab' or F(ab')2 domain of an IgG1, IgG2 or IgG3 antibody, and (ii) a DNA sequence encoding the polypeptide (X), and optionally (iii) a DNA sequence encoding the linker molecule;

an expression vector comprising a corresponding DNA sequence;

a pharmaceutical composition comprising a fusion protein as specified above and below, optionally together with a suitable carrier, excipient or diluent or another therapeutically effective drug, such as chemotherapeutics or cytotoxic drugs;

a method for preparing an immunogenicly modified fusion protein as specified comprising the steps:

(i) determining the amino acid sequence of the parent fusion protein or part thereof;

(ii) identifying one or more potential T-cell epitopes within the amino acid sequence of the fusion protein by any method including determination of the binding of the peptides to MHC molecules using in vitro or in silico techniques or biological assays, (iii) designing new sequence variants by alteration of at least one amino acid residue within the originally identified T-cell epitope sequences, said variants are modified in such a way to substantially reduce or eliminate the activity or number of the T-cell epitope sequences and/or the number of MHC allotypes able to bind peptides derived from said biological molecule as determined by the binding of the peptides to MHC molecules using in vitro or in silico techniques or biological assays or by binding of peptide-MHC complexes to T-cells, (iv) constructing such sequence variants by recombinant DNA techniques and testing said variants in order to identify one or more variants with desirable properties, and (v) optionally repeating steps (ii)-(iv), characterized in that the identification of T-cell epitope sequences according to step (ii) is achieved by (a) selecting a region of the peptide having a known amino acid residue sequence; (b) sequentially sampling overlapping amino acid residue segments of predetermined uniform size and constituted by at least three amino acid residues from the selected region; (c) calculating MHC Class II molecule binding score for each said sampled segment by summing assigned values for each hydrophobic amino acid residue side chain present in said sampled amino acid residue segment; and (d) identifying at least one of said segments suitable for modification, based on the calculated MHC Class II molecule binding score for that segment, to change overall MHC Class II binding score for the peptide without substantially the reducing therapeutic utility of the peptide;

a corresponding method, wherein step (c) is carried out by using a Böhm scoring function modified to include 12-6 van der Waal's ligand-protein energy repulsive term and ligand conformational energy term by (1) providing a first data base of MHC Class II molecule models; (2) providing a second data base of allowed peptide backbones for said MHC Class II molecule models; (3) selecting a model from said first data base; (4) selecting an allowed peptide backbone from said second data base; (5) identifying amino acid residue side chains present in each sampled segment; (6) determining the binding affinity value for all side chains present in each sampled segment; and optionally (7) repeating steps (1) through (5) for each said model and each said backbone;

a corresponding method, wherein the sampled amino acid residue segment is constituted by 13 amino acid residues and/or consecutive sampled amino acid residue segments overlap by one to five amino acid residues;

a corresponding method, wherein 1-9 amino acid residues, preferably one amino acid residue, in any of the originally present T-cell epitope sequences (is) are altered;

a corresponding method, wherein the alteration of the amino acid residues is substitution, deletion or addition of originally present amino acid(s) residue(s) by other amino acid residue(s) at specific position(s);

a corresponding method, wherein additionally further alteration by substitution, deletion or addition is conducted to restore biological activity of said biological molecule.

The polypeptides according to the invention include also antigens, like PMSA and others. Antigens which elicit a not desired and too strong immune response can be modified according to the method of the invention and result in antigens which have a reduced immunogenicity which is however strong enough for using the antigen e.g. as vaccine. The invention includes also variants and other modification of a specific polypeptide, protein, fusion protein, immunoglobulin or immunoconjugate which have in principal the same biological activity and a similar (reduced) immunogenicity. All proteins mentioned above are well known and described in the art or are already commercially available. Most of them are known to have a proved therapeutic benefit. The leader or signal sequences and linker sequences may be optional.

Preparing the fusion protein by linking the immunoglobulin component by its C-terminus or its fragment to the N-terminus of the non-immunoglobulin target polypeptide (X), optionally via the linker molecule according to step (ii) as described above, is carried out by:

(i) preparing a gene construct comprising a DNA sequence encoding the polypeptide X, a DNA sequence encoding the immunoglobulin molecule or fragments thereof [sFv, Fab, Fab', $F(ab')_2$, Fc], and optionally the DNA sequence of a the linker molecule, and (ii) expressing the gene construct by an expression system.

The immunoconjugates according to the present invention reveal enhanced properties. Thus decreased protein degradation, increased stability and enhanced serum circulation half-life can be measured as well as a distinctly reduced immunogenicity and/or allergenicity. Surprisingly, the reduced immunogenicity leads in many cases to a further increase of half-life, especially in cases where Fc-X molecules according to the invention are used. The reduced immunogenicity makes the fusion proteins according to the invention more tolerable for a given species compared to the non-modified fusion proteins and, therefore, can be administered in higher dosages if necessary.

BRIEF DESCRIPTION OF THE DRAWINGS

FIG. 1*a* shows a protein ("X") fused to an Fc moiety binding to a cell bearing an Fc receptor. FIG. 1*b* shows the fusion protein being processed such that the "X" moiety is preferentially degraded. FIG. 1*c* shows a peptide remnant of "X" being presented by an MHC molecule to a T-cell.

FIG. 2*a* shows the binding of the fusion protein to a B cell that expresses an antibody specific for "X" on its surface. The fusion protein is bound by both the specific antibody and by Fc receptors that are not already bound by the antibody.

FIG. 1*a* shows a protein ("X") fused to an cytokine moiety binding to a B cell with a surface-bound antibody. FIG. 3*b* shows the fusion protein being processed. FIG. 3*c* shows a peptide remnant of "X" being presented by an MHC molecule to a T-cell, at the same time that additional X-cytokine fusion protein is bound to the surface of the B cell.

FIG. 5*a* shows the binding of a protein bearing a glycosylation moiety to a specific cell-surface receptor for that glycosylation moiety on an immune cell. FIG. 5*b* shows the uptake and degradation of the glycosylated protein. FIG. 5*c* shows the presentation of a peptide remnant of the glycosylated protein to a T-cell via an MHC molecule.

FIG. 6*a* shows the binding of the antibody-cytokine fusion protein to a B cell that expresses an antibody specific for the CDRs of the antibody-cytokine fusion protein. The fusion protein is bound by both the specific antibody and by Fc receptors that are not already bound by the antibody. FIG. 6*b* shows the fusion protein being processed. FIG. 6*c* shows a peptide remnant of the CDRs being presented by an MHC molecule to a T-cell, at the same time that additional antibody-cytokine fusion protein is bound to the surface of the B cell.

DETAILED DESCRIPTION OF THE INVENTION

Figure 1:
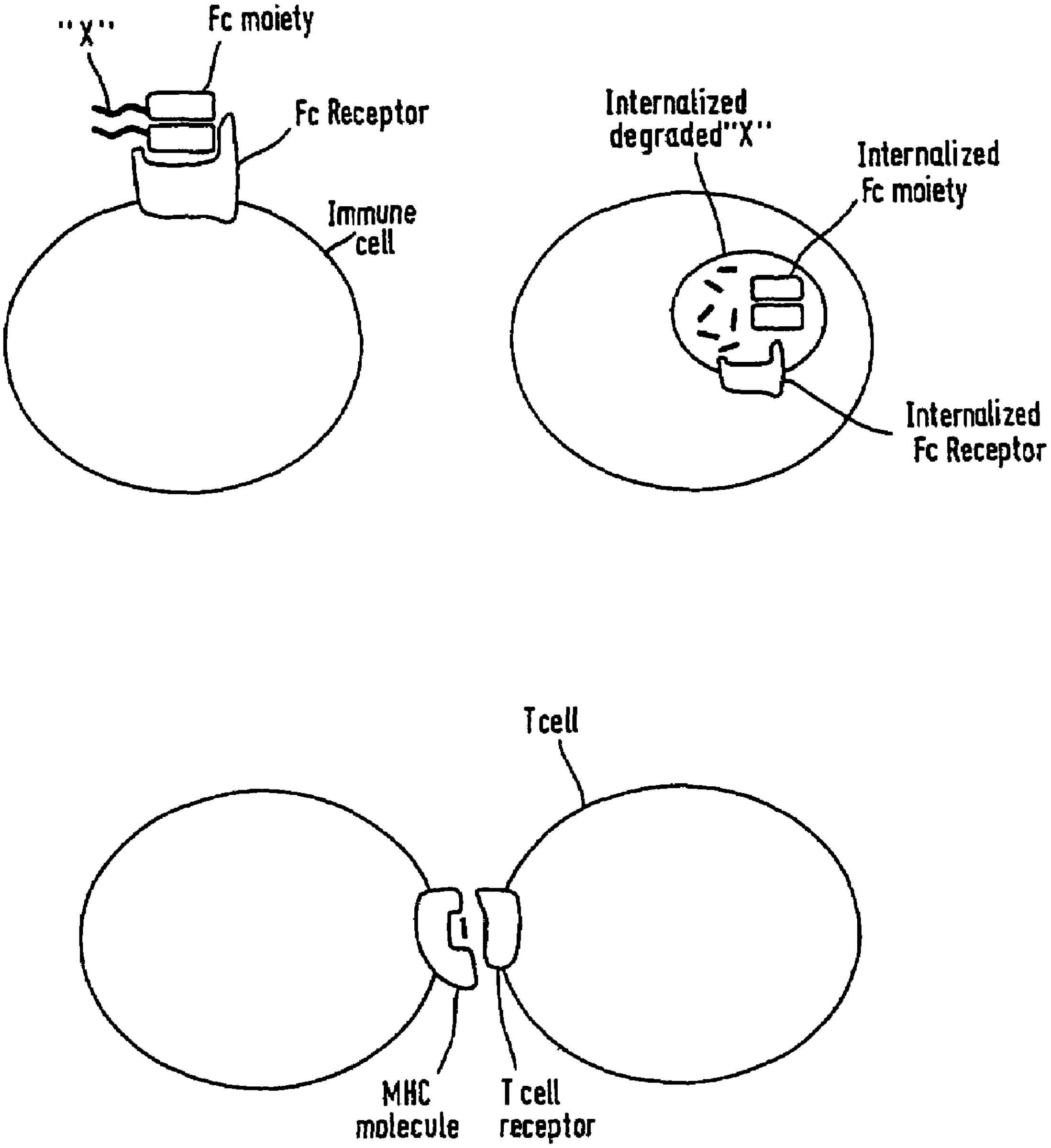
FIG. 1 illustrates one of the mechanisms by which fusion proteins displays enhanced immunogenicity.

The term "T-cell epitope" means according to the understanding of this invention an amino acid sequence which is able to bind with reasonable efficiency MHC class II molecules (or their equivalent in a non-human species), able to stimulate T-cells and/or also to bind (without necessarily measurably activating) T-cells in complex with MHC class II.

The term "peptide" as used herein and in the appended claims, is a compound that includes two or more amino acids. The amino acids are linked together by a peptide bond (defined herein below). There are 20 different naturally occurring amino acids involved in the biological production of peptides, and any number of them may be linked in any order to form a peptide chain or ring. The naturally occurring amino acids employed in the biological production of peptides all have the L-configuration. Synthetic peptides can be prepared employing conventional synthetic methods, utilizing L-amino acids, D-amino acids, or various combinations of amino acids of the two different configurations. Some peptides contain only a few amino acid units. Short peptides, e.g., having less than ten amino acid units, are sometimes referred to as "oligopeptides". Other peptides contain a large number of amino acid residues, e.g. up to 100 or more, and are referred to as "polypeptides". By convention, a "polypeptide" may be considered as any peptide chain containing three or more amino acids, whereas a "oligopeptide" is usually considered as a particular type of "short" polypeptide.

Thus, as used herein, it is understood that any reference to a "polypeptide" also includes an oligopeptide. Further, any reference to a "peptide" includes polypeptides, oligopeptides, and proteins. Each different arrangement of amino acids forms different polypeptides or proteins. The number of polypeptides- and hence the number of different proteins-that can be formed is practically unlimited.

The term "less or reduced immunogenic(ity)" used before and thereafter is a relative term and relates to the immunogenicity of the respective original source molecule when exposed in vivo to the same type of species compared with the molecule modified according to the invention.

The term "modified protein" as used according to this invention describes a protein which has reduced number of T-cell epitopes and elicits therefore a reduced immunogenicity relative to the parent protein when exposed to the immune system of a given species. The term "non-modified protein" as used according to this invention describes the "parent" protein as compared to the "modified protein" and has a larger number of T-cell epitopes and, therefore, an enhanced immunogenicity relative to the modified protein when exposed to the immune system of a given species.

The term "biologically active protein" as used here and in the claims includes according to the invention polypeptides, proteins, immunoglobulins such as antibodies, antibody fragments, fusion proteins, enzymes, antigens and so on, if not defined otherwise, which elicit a biological and/or therapeutic effect.

The term "cytokine" is used herein to describe proteins, analogs thereof, and fragments thereof which are produced and excreted by a cell, and which elicit a specific response in a cell which has a receptor for that cytokine. Preferably, cytokines include interleukins such as interleukin-2 (IL-2), hematopoietic factors such as granulocyte-macrophage colony stimulating factor (GM-CSF), tumor necrosis factor (TNF) such as TNFa, and lymphokines such as lymphotoxin. Preferably, the antibody-cytokine fusion protein of the present invention displays cytokine biological activity. In principal, the inventions encompasses all cytokines as recently classified according to their receptor code (Inglot, 1997, Archivum Immunologiae et Therapiae Experimentalis, 45: 353).

The phrase "single chain Fv" or "scFv" refers to an antibody in which the heavy chain and the light chain of a traditional two chain antibody have been joined to form one chain. Typically, a linker peptide is inserted between the two chains to allow for proper folding and creation of an active binding site.

The term "Fc region" or "Fc domain" as used in this invention is understood to mean the carboxyl terminal portion of an immunoglobulin heavy chain constant region, or an analog or portion thereof capable of binding an Fc receptor. As is known, each immunoglobulin heavy chain constant region comprises four or five domains. The domains are named sequentially as follows: CH1-hinge-CH2-CH3(-CH4). CH4 is present in IgM, which has no hinge region. The immunoglobulin heavy chain constant region useful in the practice of the invention preferably comprises an immunoglobulin hinge region, and preferably also includes a CH3 domain. The immunoglobulin heavy chain constant region most preferably comprises an immunoglobulin hinge region, a CH2 domain and a CH3 domain. The preferred Fc domain according to this invention consists thus of the hinge-CH2-CH3 domain.

As used herein, the term immunoglobulin "hinge region" is understood to mean an entire immunoglobulin hinge region or at least a portion of the immunoglobulin hinge region sufficient to form one or more disulfide bonds with a second immunoglobulin hinge region. As used herein, the term "signal sequence" is understood to mean a segment which directs the secretion of the fusion protein and thereafter is cleaved following translation in the host cell. The signal sequence of the invention is a polynucleotide which encodes an amino acid sequence which initiates transport of a protein across the membrane of the endoplasmic reticulum. Signal sequences which are useful in the invention include antibody light chain signal sequences, e.g., antibody 14.18 (Gillies et al., J. Immunol. Meth. 125 :191 (1989), and any other signal sequences which are known in the art (see, e.g., Watson, Nucleic Acid Research 12:5145 (1984)).

The term "mutant or variant" used with respect to a particular protein encompasses any molecule such as a truncated or other derivative of the relevant protein which retains substantially the same activity in humans as the relevant protein. Such other derivatives can be prepared by the addition, deletion, substitution, or rearrangement of amino acids or by chemical modifications thereof.

It is contemplated that suitable immunoglobulin heavy chain constant regions may be derived from antibodies belonging to each of the immunoglobulin classes referred to as IgA, IgD, IgE, IgG, and IgM, however, immunoglobulin heavy chain constant regions from the IgG class are preferred.

Furthermore, it is contemplated that immunoglobulin heavy chain constant regions may be derived from any of the IgG antibody subclasses referred to in the art as IgG1, IgG2, IgG3, and IgG4. Immunoglobulin heavy chain constant region domains have cross-homology among the immunoglobulin classes. For example, the CH2 domain of IgG is homologous to the CH2 domain of IgA and IgD, and to the CH3 domain of IgM and IgE. The choice of appropriate immunoglobulin heavy chain constant regions is discussed in detail in U.S. Pat. Nos. 5,541,087 and 5,726,044. The choice of particular immunoglobulin heavy chain constant region sequences from certain immunoglobulin classes and subclasses to achieve a particular result is considered to be within the level of skill in the art. It may be useful, in some circumstances, to modify the immunoglobulin heavy chain constant region, for example, by mutation, deletion or other changes mediated by genetic engineering or other approaches, so that certain activities, such as complement fixation or stimulation of antibody-dependent cell-mediated cytotoxicity (ADCC) are reduced or eliminated.

The Fc region is considered non- or weakly immunogenic if the immunoglobulin heavy chain constant region fails to generate a detectable antibody response. Furthermore, it is contemplated that substitution or deletion of amino acids within the immunoglobulin heavy chain constant regions may be useful in the practice of the invention. One example may include introducing amino acid substitutions in the upper CH2 region to create a Fc variant with reduced affinity for Fc receptors (Cole et al., J. Immunol. 159:3613 (1997)). An antibody-based fusion protein with an enhanced in vivo circulating half-life can be obtained by constructing a fusion protein having reduced binding affinity for a Fc receptor, and avoiding the use of sequences from antibody isotypes that bind to Fc receptors (WO 99/43713). For example, of the four known IgG isotypes, IgG1 (Cγ1) and IgG3 (Cγ3) are known to bind FcRγ1 with high affinity, whereas IgG4 has a 10-fold lower binding affinity, and IgG2 (Cγ2) does not bind to FcRγ1. Thus, an antibody-based fusion protein with reduced binding affinity for a Fc receptor could be obtained by constructing a fusion protein with a Cγ2 constant region (Fc region) or a Cγ4 Fc region, and avoiding constructs with a Cγ1 Fc region or a Cγ3 Fc region. An antibody-based fusion protein with an enhanced in vivo circulating half-life can be obtained by modifying sequences necessary for binding to Fc receptors in isotypes that have binding affinity for an Fc receptor, in order to reduce or eliminate binding. The important sequences for FcγR binding are Leu-Leu-Gly-Gly (residues 234 through 237 in Cγ1), located in the CH2 domain adjacent to the hinge (Canfield and Morrison, J. Exp. Med. 173:1483-1491 (1991)). Another important structural component necessary for effective FcR binding is the presence of an N-linked carbohydrate chain covalently bound to $Asn_{297}$. Enzymatic removal of this structure or mutation of the Asn residue effectively abolish, or at least dramatically reduce, binding to all classes of FcγR.

The resulting antibody-based fusion proteins have a longer in vivo circulating half-life than the unlinked second non-immunoglobulin protein. Dimerization of a ligand can increase the apparent binding affinity between the ligand and its receptor. For instance, if one X moiety of an Fc-X fusion protein can bind to a receptor on a cell with a certain affinity, the second X moiety of the same Fc-Interferon-alpha fusion protein may bind to a second receptor on the same cell with a much higher avidity (apparent affinity). This may occur because of the physical proximity of the second X moiety to the receptor after the first X moiety already is bound. In the case of an antibody binding to an antigen, the apparent affinity may be increased by at least ten thousand-fold. Each protein subunit, i.e., "X," has its own independent function so that in a multivalent molecule, the functions of the protein subunits may be additive or synergistic. Thus, fusion of the normally dimeric Fc molecule or another antibody fragment to a polypeptide X may increase the activity of X.

Nucleic acid sequences encoding, and amino acid sequences defining a human immunoglobulin Fc region, especially a Fcγ1, Fcγ2 and Fcγ3, useful in the practice of the invention are set forth in the prior, such as disclosed in (WO 00/40615, WO 00/69913, WO 00/24782) or in the Genbank and/or EMBL databases, for example, AF045536.1 (*Macaca fuscicularis*), AF045537.1 (*Macaca mulatta*), AB016710 (*Felix catus*), K00752 (*Oryctolagus cuniculus*), U03780 (*Sus scrofa*), 248947 (*Camelus dromedarius*), X62916 (*Bos taurus*), L07789 (*Mustela vison*), X69797 (*Ovis aries*), U17 166 (*Cricetulus migratorius*), X07189 (*Rattus rattus*), AF57619.1 (*Trichosurus vulpecula*), or AF035195 (*Monodelphis domestica*).

Thus, vectors reported earlier (Lo et al., Protein Engineering 11:495-500 (1998)) were modified by replacing the human IgG1 Fc sequence with sequences from cDNA encoding the mouse IgG2a Fc (U.S. Pat. No. 5,726,044).

The invention encompasses mutations in the immunoglobulin component which eliminate undesirable properties of the native immunoglobulin, such as Fc receptor binding and/or introduce desirable properties such as stability. For example, Angal S., King D. J., Bodmer M. W., Turner A., Lawson A. D. G., Roberts G., Pedley B. and Adair R., Molecular Immunology, 130: 105-108 (1993), describe an IgG4 molecule where residue 241 (Kabat numbering) is altered from serine to proline. This change increases the serum half-life of the IgG4 molecule. Canfield S. M. and Morrison S. L., Journal of Experimental Medicine, 173:1483-1491, describe the alteration of residue 248 (Kabat numbering) from leucine to glutamate in IgG3 and from glutamate to leucine in mouse IgG2b. Substitution of leucine for glutamate in the former decreases the affinity of the immunoglobulin molecule concerned for the FcγR1 receptor, and substitution of glutamate for leucine in the latter increases the affinity. EP 0307 434 discloses various mutations including an L to E mutation at residue 248 (Kabat numbering) in IgG. The constant domain(s) or fragment thereof is preferably the whole or a substantial part of the constant region of the heavy chain of human IgG. The IgG component suitably comprises the CH2 and CH3 domains and the hinge region including cysteine residues contributing to inter-heavy chain disulphide bonding. For example when the IgG component is derived from IgG4 it includes cysteine residues 8 and 11 of the IgG4 hinge region (Pinck J. R. and Milstein C., Nature, 121:941-942 (1967)).

The process of the invention may be performed by conventional recombinant techniques such as described in Maniatis et al., (Molecular Cloning-A Laboratory Manual; Cold Spring Harbor, 1982) and DNA Cloning Vols I, II and III (D. M. Glover ed., IRL Press Ltd) or Sambrook et al., (Molecular Cloning, A Laboratory Manual, Cold Spring Harbor Laboratory Press, NY, USA, 1989).

In particular, the process may comprise the steps of:

(i) preparing a replicable expression vector capable, in a host cell, of expressing a DNA polymer comprising a nucleotide sequence that encodes said compound;

(ii) transforming a host cell with said vector;

(iii) culturing said transformed host cell under conditions permitting expression of said DNA polymer to produce said compound; and (iv) recovering said compound.

The invention also provides a process for preparing the DNA polymer by the condensation of appropriate mono-, di- or oligomeric nucleotide units. The preparation may be carried out chemically, enzymatically, or by a combination of the two methods, in virro or in vivo as appropriate. Thus, the DNA polymer may be prepared by the enzymatic ligation of appropriate DNA fragments, by conventional methods such as those described by D. M. Roberts et al., in Biochemistry 24:5090-5098 (1985). The DNA fragments may be obtained by digestion of DNA containing the required sequences of nucleotides with appropriate restriction enzymes, by chemical synthesis, by enzymatic polymerisation on DNA or RNA templates, or by a combination of these methods. Digestion with restriction enzymes may be performed in an appropriate buffer at a temperature of 20°-70° C. with 0.1-10 μg DNA. Enzymatic polymerisation of DNA may be carried out in vitro using a DNA polymerase such as DNA polymerase I (Klenow fragment) in an appropriate buffer containing the nucleoside uiphosphates dATP, dCTP, dGTP and dlTP as required at a temperature of 10°-37° C., generally in a volume of 50μl or less. Enzymatic ligation of DNA fragments may be carried out using a DNA ligase such as T4 DNA ligase in an appropriate buffer at a temperature of 40° C. to ambient, generally in a volume of 50 μl or less.

The chemical synthesis of the DNA polymer or fragments may be carried out by conventional phosphotriester, phosphite or phosphoramidite chemistry, using solid phase techniques such as those described in "Chemical and Enzymatic Synthesis of Gene Fragments—A Laboratory Manual" (ed. H. G. Gassen and A. Lang), Verlag Chemie, Weinheim (1982), or in other scientific publications, for example M. J. Gait, H. W. D. Matthes, M. Singh, B. S. Sproat, and R. C. Titmas, Nucleic Acids Research, 10:6243 (1982); B. S. Sproat and W. Bannwarth, Tetrahedron Letters, 24:5771 (1983); M. D. Matteucci and M. H Caruthers, Tetrahedron Letters, 21:719 (1980); M. D. Matteucci and M. H. Caruthers, Journal of the American Chemical Society, 103:3185 (1981); S. P. Adams et al., Journal of the American Chemical Society, 105:661 (1983); N. D. Sinha, J. Biemat, J. McMannus, and H. Koester, Nucleic Acids Research, 12:4539 (1984); and H. W. D. Matthes et al., EMBO Journal, 3:801 (1984). Preferably an automated DNA synthesizer is employed.

The DNA molecules may be obtained by the digestion with suitable restriction enzymes of vectors carrying the required coding sequences or by use of polymerase chain reaction technology. The precise structure of the DNA molecules and the way in which they are obtained depends upon the structure of the desired product. The design of a suitable strategy for the construction of the DNA molecule coding for the compound is a routine matter for the skilled worker in the art.

The expression of the DNA polymer encoding the compound in a recombinant host cell may be carried out by means of a replicable expression vector capable, in the host cell, of expressing the DNA polymer. The expression vector is novel and also forms part of the invention. The replicable expression vector may be prepared in accordance with the invention, by cleaving a vector compatible with the host cell to provide a linear DNA segment having an intact replicon, and combining said linear segment with one or more DNA molecules which, together with said linear segment, encode the compound, under ligating conditions. The ligation of the linear segment and more than one DNA molecule may be carried out simultaneously or sequentially as desired. Thus, the DNA polymer may be preformed or formed during the construction of the vector, as desired. A useful expression vector is described at Lo et al., Protein Engineering 11:495 (1988), in which the transcription of the Fc-X gene utilizes the enhancer/promoter of the human cytomegalovirus and the SV40 polyadenylation signal. Suitable vectors include plasmids, bacteriophages, cosmids and recombinant viruses derived from, for example, baculoviruses, vaccinia or Semliki Forest virus. Thus, vectors reported earlier (Lo et al., Protein Engineering 11:495-500 (1998)) were modified by replacing the human IgG1 Fc sequence with sequences from cDNA encoding the mouse IgG2a Fc (U.S. Pat. No. 5,726,044).

The choice of vector will be determined in part by the host cell, which may be prokaryotic, such as *E. coli*, or eukaryotic, such as mouse C127, mouse myeloma, Chinese hamster ovary, COS or Hela cells, fungi e.g. filamentous fungi or unicellular yeast or an insect cell such as *Drosophila*. Currently preferred host cells for use in the invention include immortal hybridoma cells, NS/0 myeloma cells, 293 cells, Chinese hamster ovary cells, HELA cells, and COS cells. The host cell may also be a transgenic animal. Polymerisation and ligation may be performed as described above for the preparation of the DNA polymer. Digestion with restriction enzymes may be performed in an appropriate buffer at a temperature of 20°-70° C. with 0.1-10 μg DNA. The recombinant host cell is prepared, in accordance with the invention, by transforming a host cell with a replicable expression vector of the invention under transforming conditions. Suitable transforming conditions are conventional and are described in, for example, Maniatis et al., cited above, or "DNA Cloning" Vol. II, D. M. Glover ed., IRL Press Ltd, 1985. The choice of transforming conditions is determined by the host cell. Thus, a bacterial host such as *E. coli* may be treated with a solution of $CaCl_2$ (Cohen et al., *Proc. Nat. Acad. Sci.*, 69:2110 (1973)) or with a solution comprising a mixture of RbCl, $MnCl_2$, potassium acetate and glycerol, and then with 3-[N-morpholinol-propane-sulphonic acid, RbCl and glycerol. Mammalian cells in culture may be transformed by calcium co-precipitation of the vector DNA onto the cells. The invention also extends to a host cell transformed or transfected with a replicable expression vector of the invention. Culturing the transformed host cell under conditions permitting expression of the DNA polymer is carried out conventionally, as described in, for example, Maniatis et al. and "DNA Cloning" cited above. Thus, preferably the cell is supplied with nutrient and cultured at a temperature below 45° C. The expression product is recovered by conventional methods according to the host cell. Thus, where the host cell is bacterial, such as *E. coli*, it may be lysed physically, chemically or enzymatically and the protein product isolated from the resulting lysate. If the product is to be secreted from the bacterial cell it may be recovered from the periplasmic space or the nutrient medium. Where the host cell is mammalian, the product may generally be isolated from the nutrient medium. The DNA polymer may be assembled into vectors designed for isolation of stable transformed mammalian cell lines expressing the product: e.g. bovine papillomavirus vectors or amplified vectors in Chinese hamster ovary cells (DNA Cloning, Vol. 11, D. M. Glover ed. IRL Press (1985); Kaufman, R. J., Molecular and Cellular Biology, 5:1750-1759 (1985); Pavlakis G. N. and Hamer, D. H., Proceedings of the National Academy of Sciences (USA) 80:397-401 (1983); Goeddel, D. V. et al., and EP 0 093 619 (1983)).

The immunoconjugates of the invention may comprise linker molecules. The linker is preferably made up of amino acids linked together by peptide bonds. Thus, in preferred embodiments, the linker is made up of from 1 to 20 amino acids linked by peptide bonds, wherein the amino acids are selected from the 20 naturally occurring amino acids. Some of these amino acids may be glycosylated, as is well understood by those in the art. In a more preferred embodiment, the 1 to 20 amino acids are selected from glycine, alanine, proline, asparagine, glutamine, and lysine. Even more preferably, a linker is made up of a majority of amino acids that are sterically unhindered, such as glycine and alanine. Thus, preferred linkers are polyglycines such as polyGly (particularly $(Gly)_2$-$(Gly)_7$), poly(Gly-Ala), polyAla.

Other specific examples of suitable linkers are:

| | |
|---|---|
| $(Gly)_3Lys(Gly)_4$, | (SEQ ID NO: 1) |
| $(Gly)_3AsnGlySer(Gly)_2$, | (SEQ ID NO: 2) |
| $(Gly)_3Cys(Gly)_4$, and | (SEQ ID NO: 3) |
| GlyProAsnGlyGly. | (SEQ ID NO: 4) |

Combinations of Gly and Ala are also preferred. The linkers shown here are exemplary; linkers within the scope of this invention may be much longer and may include other residues. Non-peptide linkers are also possible. The peptide linkers may be altered to form derivatives in the same manner as described above.

Preferred linkers of the invention are not or less immunogenic. Most of the above-cited linker peptides are at least less immunogenic. However it is possible that creating the linkage between an antibody or a sFv, Fab, Fab' or F(ab')2 or a Fc domain and the target protein via a linker peptide molecule as mentioned above, new immunogenic epitopes may be newly created within the linkage region resulting in an immunoconjugate which has an increased immunogenicity compared to the immunogenicity of the single (de-immunized) components.

This situation can also be extended to fusion protein having no linker molecule. Therefore, the invention also relates to de-immunized regions of a fusion protein according to the invention, the so-called fusion or junction regions. When fusing a first protein molecule with a second protein molecule (which also can be a linker molecule) via the C- and N-terminals a sequence region is created that is artificial and, thus, was usually not yet seen by the immune system. This region is deemed is be immunogenic. The region of amino acid residues comprise according to the invention approximately 10 residues of each protein terminal (N- or C-terminal). The complete fusion region comprises, therefore, about 20 amino acid residues, preferably 2-16, more preferably 2-10 (which is 1-8 and 1-5 amino acid residues, respectively, of each fusion partner).

The invention includes also further Fc variants. Such further Fc variants, one may remove one or more sites of a native Fc that provide structural features or functional activity not required by the fusion molecules of this invention. One may remove these sites by, for example, substituting or deleting residues, inserting residues into the site, or truncating portions containing the site. The inserted or substituted residues may also be altered amino acids, such as peptidomimetics or D-amino acids. For example, one or more glycosylation sites may be removed. Residues that are typically glycosylated (e.g., asparagine) may confer cytolytic response. Such residues may be deleted or substituted with unglycosylated residues (e.g., alanine). ADCC site as well as sites involved in interaction with complement, such as the Clq binding site, may also be removed if there is a specific need.

The invention includes also derivatives of the target polypeptide (X) of the invention. Such derivatives may further improve the solubility, absorption, biological half life, and the like of (X). The modified (X) may alternatively eliminate or attenuate any undesirable side-effect and the like. Exemplary derivatives include also compounds in which (X) or some portion thereof is cyclic. For example, the peptide portion may be modified to contain two or more Cys residues (e.g., in the linker), which could cyclize by disulfide bond formation. The compound is cross-linked or is rendered capable of cross-linking between molecules. For example, the peptide portion may be modified to contain one Cys residue and thereby be able to form an intermolecular disulfide bond with a like molecule.

In a final aspect the present invention relates to pharmaceutical compositions comprising said biologically active proteins obtainable by the methods disclosed in the present invention, and methods for therapeutic treatment of humans using the modified molecules and pharmaceutical compositions.

Therapeutic compositions of the present invention contain a physiologically tolerable carrier together with the relevant agent as described herein, dissolved or dispersed therein as an active ingredient. As used herein, the terms “pharmaceutically acceptable”, “physiologically tolerable” and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. The preparation of a pharmacological composition that contains active ingredients dissolved or dispersed therein is well understood in the art and need not be limited based on formulation. Typically, such compositions are prepared as injectables either as liquid solutions or suspensions, however, solid forms suitable for solution, or suspensions, in liquid prior to use can also be prepared.

The preparation can also be emulsified. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Particularly preferred is the HCl salt when used in the preparation of cyclic polypeptide αv antagonists. Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions.

Typically, a therapeutically effective amount of a modified immunoglobulin in the form of a modified antibody or antibody fragment according to the invention is an amount such that when administered in physiologically tolerable composition is sufficient to achieve a plasma concentration of from about 0.01 microgram (μg) per milliliter (ml) to about 100 μg/ml, preferably from about 1 μg/ml to about 5 μg/ml and usually about 5 μg/ml. Stated differently, the dosage can vary from about 0.1 mg/kg to about 300 mg/kg, preferably from about 0.2 mg/kg to about 200 mg/kg, most preferably from about 0.5 mg/kg to about 20 mg/kg, in one or more dose administrations daily for one or several days. Where the immunotherapeutic agent is in the form of a fragment of a monoclonal antibody or a conjugate, the amount can readily be adjusted based on the mass of the fragment/conjugate relative to the mass of the whole antibody. A preferred plasma concentration in molarity is from about 2 micromolar (μM) to about 5 millimolar (mM) and preferably, about 100 μM to 1 mM antibody antagonist.

A therapeutically effective amount of an agent according of this invention which is a non-immunotherapeutic peptide or a protein is typically an amount of such a molecule such that when administered in a physiologically tolerable composition is sufficient to achieve a plasma concentration of from about 0.1 microgram (μg) per milliliter (ml) to about 200 μg/ml, preferably from about 1 μg/ml to about 150 μg/ml. Based on a protein having a mass of about 500 grams per mole, the preferred plasma concentration in molarity is from about 2 micromolar (μM) to about 5 millimolar (mM) and preferably about 100 μM to 1 mM polypeptide antagonist.

The pharmaceutical compositions of the invention can comprise phrase encompasses treatment of a subject with agents that reduce or avoid side effects associated with the combination therapy of the present invention ("adjunctive therapy"), including, but not limited to, those agents, for example, that reduce the toxic effect of anticancer drugs. Said adjunctive agents prevent or reduce the incidence of nausea and vomiting associated with chemotherapy, radiotherapy or operation, or reduce the incidence of infection associated with the administration of myelosuppressive anticancer drugs. Adjunctive agents are well known in the art. The modified proteins according to the invention can additionally administered with adjuvants like BCG and immune system stimulators.

Furthermore, the compositions may include immunotherapeutic agents, chemotherapeutic agents and anti-neoplastic agents which may contain cytotoxic effective radio labeled isotopes, or other cytotoxic agents, such as a cytotoxic peptides (e.g. cytokines) or cytotoxic drugs and the like. The typical dosage of an active agent, which is a preferably a chemical antagonist or a (chemical) chemotherapeutic agent according to the invention (neither an immunotherapeutic agent nor a non-immunotherapeutic peptide/protein) is 10 mg to 1000 mg, preferably about 20 to 200 mg, and more preferably 50 to 100 mg per kilogram body weight per day.

The following examples describe the in invention in more detail. However, this listing does not limit the invention.

EXAMPLE 1

The following example describes in detail a preferred method for identification of immunogenic sequence regions (T-cell epitopes) within the sequences of the fusion proteins as disclosed in this invention. However, it should be pointed out, that said molecules can be obtained by other known methods.

The identification of T-cell epitopes of the molecules which were modified in order to obtain the immunoconjugates according to the present invention can be achieved by different methods which are described in the prior art (WO 92/10755 and WO 96/40792 (Novo Nordisk), EP 0519 596 (Merck & Co.), EP 0699 755 (Centro de Immunologia Moelcular), WO 98/52976 and WO 98/59244 (Biovation Ltd.) or related methods.

Advantageous immunoconjugates, however, can be obtained if the identification of said epitopes is realized by the following new method which is described herewith in detail: There are a number of factors that play important roles in determining the total structure of a protein, polypeptide or immunoglobulin. First, the peptide bond, i.e., that bond which joins the amino acids in the chain together, is a covalent bond. This bond is planar in structure, essentially a substituted amide. An "amide" is any of a group of organic compounds containing the grouping —CONH—.

The planar peptide bond linking C$\alpha$ of adjacent amino acids may be represented as depicted below:

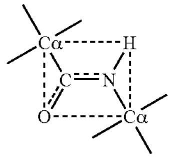

Because the O═C and the C—N atoms lie in a relatively rigid plane, free rotation does not occur about these axes. Hence, a plane schematically depicted by the interrupted line is sometimes referred to as an "amide" or "peptide plane" plane wherein lie the oxygen (O), carbon (C), nitrogen (N), and hydrogen (H) atoms of the peptide backbone. At opposite corners of this amide plane are located the C$\alpha$ atoms. Since there is substantially no rotation about the O═C and C—N atoms in the peptide or amide plane, a polypeptide chain thus comprises a series of planar peptide linkages joining the C$\alpha$ atoms.

A second factor that plays an important role in defining the total structure or conformation of a polypeptide or protein is the angle of rotation of each amide plane about the common C$\alpha$ linkage. The terms "angle of rotation" and "torsion angle" are hereinafter regarded as equivalent terms. Assuming that the O, C, N, and H atoms remain in the amide plane (which is usually a valid assumption, although there may be some slight deviations from planarity of these atoms for some conformations), these angles of rotation define the N and R polypeptide's backbone conformation, i.e., the structure as it exists between adjacent residues. These two angles are known as $\phi$ and $\psi$. A set of the angles $\phi_1$, $\psi_1$, where the subscript i represents a particular residue of a polypeptide chain, thus effectively defines the polypeptide secondary structure. The conventions used in defining the $\phi$, $\psi$ angles, i.e., the reference points at which the amide planes form a zero degree angle, and the definition of which angle is $\phi$, and which angle is $\psi$, for a given polypeptide, are defined in the literature. See, e.g., Ramachandran et al., *Adv. Prot. Chem.* 23:283-437 (1968), at pages 285-94, which pages are incorporated herein by reference.

The present method can be applied to any protein, and is based in part upon the discovery that in humans the primary Pocket 1 anchor position of MHC Class II molecule binding grooves has a well designed specificity for particular amino acid side chains. The specificity of this pocket is determined by the identity of the amino acid at position 86 of the beta chain of the MHC Class II molecule. This site is located at the bottom of Pocket 1 and determines the size of the side chain that can be accommodated by this pocket. Marshall, K. W., *J. Immunol.,* 152:4946-4956 (1994). If this residue is a glycine, then all hydrophobic aliphatic and aromatic amino acids (hydrophobic aliphatics being: valine, leucine, isoleucine, methionine and aromatics being: phenylalanine, tyrosine and tryptophan) can be accommodated in the pocket, a preference being for the aromatic side chains. If this pocket residue is a valine, then the side chain of this amino acid protrudes into the pocket and restricts the size of peptide side chains that can be accommodated such that only hydrophobic aliphatic side chains can be accommodated. Therefore, in an amino acid residue sequence, wherever an amino acid with a hydrophobic aliphatic or aromatic side chain is found, there is the potential for a MHC Class II restricted T-cell epitope to be present. If the side-chain is hydrophobic aliphatic, however, it is approximately twice as likely to be associated with a T-cell epitope than an aromatic side chain (assuming an approximately even distribution of Pocket I types throughout the global population).

A computational method embodying the present invention profiles the likelihood of peptide regions to contain T-cell epitopes as follows:

(1) The primary sequence of a peptide segment of predetermined length is scanned, and all hydrophobic aliphatic and aromatic side chains present are identified. (2) The hydrophobic aliphatic side chains are assigned a value greater than that for the aromatic side chains; preferably about twice the value assigned to the aromatic side chains, e.g., a value of 2 for a hydrophobic aliphatic side chain and a value of 1 for an aromatic side chain. (3) The values determined to be present are summed for each overlapping amino acid residue segment (window) of predetermined uniform length within the peptide, and the total value for a particular segment (window) is assigned to a single amino acid residue at an intermediate position of the segment (window), preferably to a residue at about the midpoint of the sampled segment (window). This procedure is repeated for each sampled overlapping amino acid residue segment (window). Thus, each amino acid residue of the peptide is assigned a value that relates to the likelihood of a T-cell epitope being present in that particular segment (window). (4) The values calculated and assigned as described in Step 3, above, can be plotted against the amino acid coordinates of the entire amino acid residue sequence being assessed. (5) All portions of the sequence which have a score of a predetermined value, e.g., a value of 1, are deemed likely to contain a T-cell epitope and can be modified, if desired.

This particular aspect of the present invention provides a general method by which the regions of peptides likely to contain T-cell epitopes can be described. Modifications to the peptide in these regions have the potential to modify the MHC Class II binding characteristics. According to another aspect of the present invention, T-cell epitopes can be predicted with greater accuracy by the use of a more sophisticated computational method which takes into account the interactions of peptides with models of MHC Class II alleles.

The computational prediction of T-cell epitopes present within a peptide according to this particular aspect contemplates the construction of models of at least 42 MHC Class II alleles based upon the structures of all known MHC Class II molecules and a method for the use of these models in the computational identification of T-cell epitopes, the construction of libraries of peptide backbones for each model in order to allow for the known variability in relative peptide backbone alpha carbon (Cα) positions, the construction of libraries of amino-acid side chain conformations for each backbone dock with each model for each of the 20 amino-acid alternatives at positions critical for the interaction between peptide and MHC Class II molecule, and the use of these libraries of backbones and side-chain conformations in conjunction with a scoring function to select the optimum backbone and side-chain conformation for a particular peptide docked with a particular MHC Class II molecule and the derivation of a binding score from this interaction.

Models of MHC Class II molecules can be derived via homology modeling from a number of similar structures found in the Brookhaven Protein Data Bank ("PDB"). These may be made by the use of semi-automatic homology modeling software (Modeller, Sali A. & Blundell T L., *J. Mol Biol* 234:779-815 (1993)) which incorporates a simulated annealing function, in conjunction with the CHARMm force-field for energy minimisation (available from Molecular Simulations Inc., San Diego, Calif.). Alternative modeling methods can be utilized as well.

The present method differs significantly from other computational methods which use libraries of experimentally derived binding data of each amino-acid alternative at each position in the binding groove for a small set of MHC Class II molecules (Marshall, K. W., et al., *Biomed. Pept. Proteins Nucleic Acids,* 1(3): 157-162 (1995)) or yet other computational methods which use similar experimental binding data in order to define the binding characteristics of particular types of binding pockets within the groove, again using a relatively small subset of MHC Class II molecules, and then 'mixing and matching' pocket types from this pocket library to artificially create further 'virtual' MHC Class II molecules (Sturniolo T., et al., *Nat. Biotech,* 17(6):555-561 (1999)). Both prior methods suffer the major disadvantage that, due to the complexity of the assays and the need to synthesize large numbers of peptide variants, only a small number of MHC Class II molecules can be experimentally scanned. Therefore the first prior method can only make predictions for a small number of MHC Class II molecules. The second prior method also makes the assumption that a pocket lined with similar amino-acids in one molecule will have the same binding characteristics when in the context of a different Class II allele and suffers further disadvantages in that only those MHC Class II molecules can be 'virtually' created which contain pockets contained within the pocket library. Using the modeling approach described herein, the structure of any number and type of MHC Class II molecules can be deduced, therefore alleles can be specifically selected to be representative of the global population. In addition, the number of MHC Class II molecules scanned can be increased by making further models further than having to generate additional data via complex experimentation.

The use of a backbone library allows for variation in the positions of the Cα atoms of the various peptides being scanned when docked with particular MHC Class II molecules. This is again in contrast to the alternative prior computational methods described above which rely on the use of simplified peptide backbones for scanning amino-acid binding in particular pockets. These simplified backbones are not likely to be representative of backbone conformations found in 'real' peptides leading to inaccuracies in prediction of peptide binding. The present backbone library is created by superposing the backbones of all peptides bound to MHC Class II molecules found within the Protein Data Bank and noting the root mean square (RMS) deviation between the Cα atoms of each of the eleven amino-acids located within the binding groove. While this library can be derived from a small number of suitable available mouse and human structures (currently 13), in order to allow for the possibility of even greater variability, the RMS figure for each C"-α position is increased by 50%. The average Cα position of each amino-acid is then determined and a sphere drawn around this point whose radius equals the RMS deviation at that position plus 50%. This sphere represents all allowed Cα positions.

Working from the Cα with the least RMS deviation (that of the amino-acid in Pocket 1 as mentioned above, equivalent to Position 2 of the 11 residues in the binding groove), the sphere is three-dimensionally gridded, and each vertex within the grid is then used as a possible location for a Cα of that amino-acid. The subsequent amide plane, corresponding to the peptide bond to the subsequent amino-acid is grafted onto each of these Cαs and the φ and ψ angles are rotated step-wise at set intervals in order to position the subsequent Cα. If the subsequent Cα falls within the 'sphere of allowed positions' for this Cα than the orientation of the dipeptide is accepted, whereas if it falls outside the sphere then the dipeptide is rejected. This process is then repeated for each of the subsequent Cα positions, such that the peptide grows from the Pocket 1 Cα 'seed', until all nine subsequent Cαs have been positioned from all possible permutations of the preceding Cαs. The process is then repeated once more for the single Cα preceding pocket 1 to create a library of backbone Cα positions located within the binding groove.

The number of backbones generated is dependent upon several factors: The size of the 'spheres of allowed positions'; the fineness of the gridding of the 'primary sphere' at the Pocket 1 position; the fineness of the step-wise rotation of the φ and ψ angles used to position subsequent Cαs. Using this process, a large library of backbones can be created. The larger the backbone library, the more likely it will be that the optimum fit will be found for a particular peptide within the binding groove of an MHC Class II molecule. Inasmuch as all backbones will not be suitable for docking with all the models of MHC Class II molecules due to clashes with amino-acids of the binding domains, for each allele a subset of the library is created comprising backbones which can be accommodated by that allele. The use of the backbone library, in conjunction with the models of MHC Class II molecules creates an exhaustive database consisting of allowed side chain conformations for each amino-acid in each position of the binding groove for each MHC Class II molecule docked with each allowed backbone. This data set is generated using a simple steric overlap function where a MHC Class II molecule is docked with a backbone and an amino-acid side chain is grafted onto the backbone at the desired position. Each of the rotatable bonds of the side chain is rotated step-wise at set intervals and the resultant positions of the atoms dependent upon that bond noted. The interaction of the atom with atoms of side-chains of the binding groove is noted and positions are either accepted or rejected according to the following criteria: The sum total of the overlap of all atoms so far positioned must not exceed a pre-determined value. Thus the stringency of the conformational search is a function of the interval used in the step-wise rotation of the bond and the pre-determined limit for the total overlap. This latter value can be small if it is known that a particular pocket is rigid, however the stringency can be relaxed if the positions of pocket side-chains are known to be relatively flexible. Thus allowances can be made to imitate variations in flexibility within pockets of the binding groove. This conformational search is then repeated for every amino-acid at every position of each backbone when docked with each of the MHC Class II molecules to create the exhaustive database of side-chain conformations.

A suitable mathematical expression is used to estimate the energy of binding between models of MHC Class II molecules in conjunction with peptide ligand conformations which have to be empirically derived by scanning the large database of backbone/side-chain conformations described above. Thus a protein is scanned for potential T-cell epitopes by subjecting each possible peptide of length varying between 9 and 20 amino-acids (although the length is kept constant for each scan) to the following computations: An MHC Class II molecule is selected together with a peptide backbone allowed for that molecule and the side-chains corresponding to the desired peptide sequence are grafted on. Atom identity and interatomic distance data relating to a particular side-chain at a particular position on the backbone are collected for each allowed conformation of that amino-acid (obtained from the database described above). This is repeated for each side-chain along the backbone and peptide scores derived using a scoring function. The best score for that backbone is retained and the process repeated for each allowed backbone for the selected model. The scores from all allowed backbones are compared and the highest score is deemed to be the peptide score for the desired peptide in that MHC Class II model. This process is then repeated for each model with every possible peptide derived from the protein being scanned, and the scores for peptides versus models are displayed.

In the context of the present invention, each ligand presented for the binding affinity calculation is an amino-acid segment selected from a peptide or protein as discussed above. Thus, the ligand is a selected stretch of amino acids about 9 to 20 amino acids in length derived from a peptide, polypeptide or protein of known sequence. The terms "amino acids" and "residues" are hereinafter regarded as equivalent terms. The ligand, in the form of the consecutive amino acids of the peptide to be examined grafted onto a backbone from the backbone library, is positioned in the binding cleft of an MHC Class II molecule from the MHC Class II molecule model library via the coordinates of the C"-α atoms of the peptide backbone and an allowed conformation for each side-chain is selected from the database of allowed conformations. The relevant atom identities and interatomic distances are also retrieved from this database and used to calculate the peptide binding score. Ligands with a high binding affinity for the MHC Class II binding pocket are flagged as candidates for site-directed mutagenesis. Amino-acid substitutions are made in the flagged ligand (and hence in the protein of interest) which is then retested using the scoring function in order to determine changes which reduce the binding affinity below a predetermined threshold value. These changes can then be incorporated into the protein of interest to remove T-cell epitopes. Binding between the peptide ligand and the binding groove of MHC Class II molecules involves non-covalent interactions including, but not limited to: hydrogen bonds, electrostatic interactions, hydrophobic (lipophilic) interactions and Van der Walls interactions. These are included in the peptide scoring function as described in detail below. It should be understood that a hydrogen bond is a non-covalent bond which can be formed between polar or charged groups and consists of a hydrogen atom shared by two other atoms. The hydrogen of the hydrogen donor has a positive charge where the hydrogen acceptor has a partial negative charge. For the purposes of peptide/protein interactions, hydrogen bond donors may be either nitrogens with hydrogen attached or hydrogens attached to oxygen or nitrogen. Hydrogen bond acceptor atoms may be oxygens not attached to hydrogen, nitrogens with no hydrogens attached and one or two connections, or sulphurs with only one connection. Certain atoms, such as oxygens attached to hydrogens or imine nitrogens (e.g. C═NH) may be both hydrogen acceptors or donors. Hydrogen bond energies range from 3 to 7 Kcal/mol and are much stronger than Van der Waal's bonds, but weaker than covalent bonds. Hydrogen bonds are also highly directional and are at their strongest when the donor atom, hydrogen atom and acceptor atom are co-linear. Electrostatic bonds are formed between oppositely charged ion pairs and the strength of the interaction is inversely proportional to the square of the distance between the atoms according to Coulomb's law. The optimal distance between ion pairs is about 2.8 Å. In protein/peptide interactions, electrostatic bonds may be formed between arginine, histidine or lysine and aspartate or glutamate. The strength of the bond will depend upon the pKa of the ionizing group and the dielectric constant of the medium although they are approximately similar in strength to hydrogen bonds.

Lipophilic interactions are favorable hydrophobic-hydrophobic contacts that occur between he protein and peptide ligand. Usually, these will occur between hydrophobic amino acid side chains of the peptide buried within the pockets of the binding groove such that they are not exposed to solvent. Exposure of the hydrophobic residues to solvent is highly unfavorable since the surrounding solvent molecules are forced to hydrogen bond with each other forming cage-like clathrate structures. The resultant decrease in entropy is highly unfavorable. Lipophilic atoms may be sulphurs which are neither polar nor hydrogen acceptors and carbon atoms which are not polar.

Van der Waal's bonds are non-specific forces found between atoms which are 3-4 Å apart. They are weaker and less specific than hydrogen and electrostatic bonds. The distribution of electronic charge around an atom changes with time and, at any instant, the charge distribution is not symmetric. This transient asymmetry in electronic charge induces a similar asymmetry in neighboring atoms. The resultant attractive forces between atoms reaches a maximum at the Van der Waal's contact distance but diminishes very rapidly at about 1 Å to about 2 Å. Conversely, as atoms become separated by less than the contact distance, increasingly strong repulsive forces become dominant as the outer electron clouds of the atoms overlap. Although the attractive forces are relatively weak compared to electrostatic and hydrogen bonds (about 0.6 Kcal/mol), the repulsive forces in particular may be very important in determining whether a peptide ligand may bind successfully to a protein. In one embodiment, the Böhm scoring function (SCORE I approach) is used to estimate the binding constant. (Böhm, H. J., *J. Comput Aided Mol. Des.,* 8(3):243-256 (1994) which is hereby incorporated in its entirety). In another embodiment, the scoring function (SCORE2 approach) is used to estimate the binding affinities as an indicator of a ligand containing a T-cell epitope (Böhm, H. J., *J. Comput Aided Mol. Des.,* 12(4):309-323 (1998) which is hereby incorporated in its entirety). However, the Böhm scoring functions as described in the above references are used to estimate the binding affinity of a ligand to a protein where it is already known that the ligand successfully binds to the protein and the protein/ligand complex has had its structure solved, the solved structure being present in the Protein Data Bank ("PDB").

Therefore, the scoring function has been developed with the benefit of known positive binding data. In order to allow for discrimination between positive and negative binders, a repulsion term must be added to the equation. In addition, a more satisfactory estimate of binding energy is achieved by computing the lipophilic interactions in a pairwise manner rather than using the area based energy term of the above Böhm functions. Therefore, in a preferred embodiment, the binding energy is estimated using a modified Böhm scoring function. In the modified Böhm scoring function, the binding energy between protein and ligand ($\Delta G_{bind}$) is estimated considering the following parameters: The reduction of binding energy due to the overall loss of translational and rotational entropy of the ligand ($\Delta G_0$); contributions from ideal hydrogen bonds ($\Delta G_{hb}$) where at least one partner is neutral; contributions from unperturbed ionic interactions ($\Delta G_{ionic}$); lipophilic interactions between lipophilic ligand atoms and lipophilic acceptor atoms ($\Delta G_{lipo}$); the loss of binding energy due to the freezing of internal degrees of freedom in the ligand, i.e., the freedom of rotation about each C—C bond is reduced ($\Delta G_{rot}$); the energy of the interaction between the protein and ligand ($E_{VdW}$). Consideration of these terms gives equation 1:

$$(\Delta G_{bind})=(\Delta G_0)+(\Delta G_{hb}\times N_{hb})+(\Delta G_{ionic}\times N_{ionic})+(\Delta G_{lipo}\times N_{lipo})+(\Delta G_{rot}+N_{rot})+(E_{VdW}).$$

Where N is the number of qualifying interactions for a specific term and, in one embodiment, $\Delta G_0$, $\Delta G_{hb}$, $\Delta G_{ionic}$, $\Delta G_{lipo}$ and $\Delta G_{rot}$ are constants which are given the values: 5.4, −4.7, −4.7, −0.17, and 1.4, respectively.

The term $N_{hb}$ is calculated according to equation 2:

$$N_{hb}=\Sigma_{h\text{-}bonds}f(\Delta R, \Delta\alpha)\times f(N_{neighb})\times f_{pcs}$$

$f(\Delta R, \Delta\alpha)$ is a penalty function which accounts for large deviations of hydrogen bonds from ideality and is calculated according to equation 3:

$$f(\Delta R, \Delta-\alpha)=f1(\Delta R)\times f2(\Delta\alpha)$$

Where:

$f1(\Delta R)=1$ if $\Delta R<=TOL$ or $=1-(\Delta R-TOL)/0.4$ if $\Delta R<=0.4+TOL$ or $=0$ if $\Delta R>0.4+TOL$ And:

$f2(\Delta\alpha)=1$ if $\Delta\alpha<30°$ or $=1-(\Delta\alpha-30)/50$ if $\Delta\alpha<=80°$ or $=0$ if $\Delta\alpha>80°$ TOL is the tolerated deviation in hydrogen bond length= 0.25 Å

ΔR is the deviation of the H—O/N hydrogen bond length from the ideal value=1.9 Å Δα is the deviation of the hydrogen bond angle $\angle_{N/O-H..O/N}$ from its idealized value of 180°

$f(N_{neigb})$ distinguishes between concave and convex parts of a protein surface and therefore assigns greater weight to polar interactions found in pockets rather than those found at the protein surface. This function is calculated according to equation 4 below:

$$f(N_{neighb})=(N_{neighb}/N_{neighb,0})^{\alpha} \text{ where } \alpha=0.5$$

$N_{neighb}$ is the number of non-hydrogen protein atoms that are closer than 5 Å to any given protein atom.

$N_{neighb,0}$ is a constant=25

$f_{pcs}$ is a function which allows for the polar contact surface area per hydrogen bond and therefore distinguishes between strong and weak hydrogen bonds and its value is determined according to the following criteria:

$$f_{pcs}=\beta \text{ when } A_{polar}/N_{HB}<10\ Å^2$$

or $$f_{pcs}=1 \text{ when } A_{polar}/N_{HB}>10\ Å^2$$

$A_{polar}$ is the size of the polar protein-ligand contact surface $N_{HB}$ is the number of hydrogen bonds β is a constant whose value=1.2

For the implementation of the modified Böhm scoring function, the contributions from ionic interactions, $\Delta G_{ionic}$, are computed in a similar fashion to those from hydrogen bonds described above since the same geometry dependency is assumed.

The term $N_{lipo}$ is calculated according to equation 5 below:

$$N_{lipo}=\Sigma_{lL}f(r_{lL})$$

$f(r_{lL})$ is calculated for all lipophilic ligand atoms, l, and all lipophilic protein atoms, L, according to the following criteria:

$$f(r_{lL})=1 \text{ when } r_{lL}<=Rlf(r_{lL})=(r_{lL}-R1)/(R2-R1) \text{ when } R2<r_{lL}>R1$$

$$f(r_{lL})=0 \text{ when } r_{lL}>=R2$$

Where:

$$R1=r_l^{vdw}+r_L^{vdw}+0.5$$

and $$R2=R1+3.0$$

and $r_l^{vdw}$ is the Van der Waal's radius of atom l and $r_L^{vdw}$ is the Van der Waal's radius of atom L The term $N_{rot}$ is the number of rotable bonds of the amino acid side chain and is taken to be the number of acyclic $sp^3$-$sp^3$ and $sp^3$-$sp^2$ bonds. Rotations of terminal —$CH_3$ or —$NH_3$ are not taken into account.

The final term, $E_{VdW}$, is calculated according to equation 6 below:

$$E_{VdW}=\epsilon_1\epsilon_2((r_l^{vdw}+r_2^{vdw})^{12}/r^{12}-(r_l^{vdw}+r_2^{vdw})^6/r^6),$$

where:

$\epsilon_1$ and $\epsilon_2$ are constants dependant upon atom identity $r_1^{vdw}+r_2^{vdw}$ are the Van der Waal's atomic radii r is the distance between a pair of atoms.

With regard to Equation 6, in one embodiment, the constants $\epsilon_1$ and $\epsilon_2$ are given the atom values: C: 0.245, N: 0.283, O: 0.316, S: 0.316, respectively (i.e. for atoms of Carbon, Nitrogen, Oxygen and Sulphur, respectively). With regards to equations 5 and 6, the Van der Waal's radii are given the atom values: C: 1.85, N: 1.75, O: 1.60, S: 2.00.

It should be understood that all predetermined values and constants given in the equations above are determined within the constraints of current understandings of protein ligand interactions with particular regard to the type of computation being undertaken herein. Therefore, it is possible that, as this scoring function is refined further, these values and constants may change hence any suitable numerical value which gives the desired results in terms of estimating the binding energy of a protein to a ligand may be used and hence fall within the scope of the present invention.

As described above, the scoring function is applied to data extracted from the database of side-chain conformations, atom identities, and interatomic distances. For the purposes of the present description, the number of MHC Class II molecules included in this database is 42 models plus four solved structures. It should be apparent from the above descriptions that the modular nature of the construction of the computational method of the present invention means that new models can simply be added and scanned with the peptide backbone library and side-chain conformational search function to create additional data sets which can be processed by the peptide scoring function as described above. This allows for the repertoire of scanned MHC Class II molecules to easily be increased, or structures and associated data to be replaced if data are available to create more accurate models of the existing alleles.

The present prediction method can be calibrated against a data set comprising a large number of peptides whose affinity for various MHC Class II molecules has previously been experimentally determined. By comparison of calculated versus experimental data, a cut of value can be determined above which it is known that all experimentally determined T-cell epitopes are correctly predicted.

It should be understood that, although the above scoring function is relatively simple compared to some sophisticated methodologies that are available, the calculations are performed extremely rapidly. It should also be understood that the objective is not to calculate the true binding energy per se for each peptide docked in the binding groove of a selected MHC Class II protein. The underlying objective is to obtain comparative binding energy data as an aid to predicting the location of T-cell epitopes based on the primary structure (i.e. amino acid sequence) of a selected protein. A relatively high binding energy or a binding energy above a selected threshold value would suggest the presence of a T-cell epitope in the ligand. The ligand may then be subjected to at least one round of amino-acid substitution and the binding energy recalculated. Due to the rapid nature of the calculations, these manipulations of the peptide sequence can be performed interactively within the program's user interface on cost-effectively available computer hardware. Major investment in computer hardware is thus not required.

It would be apparent to one skilled in the art that other available software could be used for the same purposes. In particular, more sophisticated software which is capable of docking ligands into protein binding-sites may be used in conjunction with energy minimization. Examples of docking software are: DOCK (Kuntz et al., *J. Mol. Biol.,* 161:269-288 (1982)), LUDI (Böhm, H. J., *J. Comput Aided Mol. Des.,* 8:623-632 (1994)), and FLEXX (Rarey M., et al., *ISMB,* 3:300-308 (1995)). Examples of molecular modeling and manipulation software include: AMBER (Tripos) and CHARMm (Molecular Simulations Inc.). The use of these computational methods would severely limit the throughput of the method of this invention due to the lengths of processing time required to make the necessary calculations. However, it is feasible that such methods could be used as a 'secondary screen' to obtain more accurate calculations of binding energy for peptides which are found to be 'positive binders' via the method of the present invention. The limitation of processing time for sophisticated molecular mechanic or molecular dynamic calculations is one which is defined both by the design of the software which makes these calculations and the current technology limitations of computer hardware. It may be anticipated that, in the future, with the writing of more efficient code and the continuing increases in speed of computer processors, it may become feasible to make such calculations within a more manageable time-frame. Further information on energy functions applied to macromolecules and consideration of the various interactions that take place within a folded protein structure can be found in: Brooks, B. R., et al., *J. Comput. Chem.* 4:187-217 (1983), and further information concerning general protein-ligand interactions can be found in: Dauber-Osguthorpe et al., *Proteins* 4(1):31-47 (1988), which are incorporated herein by reference in their entirety. Useful background information can also be found, for example, in Fasman, G. D., ed., *Prediction of Protein Structure and the Principles of Protein Conformation*, Plenum Press, New York, ISBN: 0-306 4313-9.

EXAMPLE 2

De-Immunized Forms of Fc-Leptin

Leptin is a secreted signaling 146 amino acid residue protein involved in the homeostatic mechanisms maintaining adipose mass (e.g. WO 00/40615, WO 98/28427, WO 96/05309). The protein (and its antagonists) offers significant therapeutic potential for the treatment of diabetes, high blood pressure and cholesterol metabolism. Fc-leptin is a fusion protein for which the serum half-life is profoundly improved compared to leptin itself (WO 00/40615). However, certain forms of Fc-leptin, such as when the Fc is derived from human IgG1 or human IgG3, have the potential to show enhanced immunogenicity under certain circumstances, such as administration by subcutaneous injection. In a Phase I clinical trial, leptin alone was found to be at least somewhat immunogenic. The invention discloses sequences identified within the leptin primary sequence that are potential T-cell epitopes by virtue of MHC class II binding potential. This disclosure specifically pertains to the human leptin moiety containing about 146 amino acid residues.

Others have provided modified leptin (U.S. Pat. No. 5,900,404; WO 96/05309) but these approaches have been directed towards improvements in the commercial production of leptin, for example improved in vitro stability. Such teachings do not recognize the importance of T-cell epitopes to the immunogenic properties of the protein nor have been conceived to directly influence said properties in a specific and controlled way according to the scheme of the present invention. Specific Fc-leptin forms: Fcγ1-leptin, Fcγ2-leptin, both forms, preferably with linker peptide and optionally modified Fc domain having reduced affinity to Fc-receptors. Sequences to be modified in leptin are shown below in Table 1. Substitutions leading to elimination of T-cell epitopes of human leptin are shown in Table 2. An amino acid sequence which is part of the sequence of an immunogenically non-modified human obesity protein (leptin) and has a potential MHC class II binding activity is selected from the following group as shown in Table 1, identified according to the method of the invention.

TABLE 1

Peptide sequences in human leptin with potential human MHC class II binding activity.

| | |
|---|---|
| VPIQKVQDDTKTL, (SEQ ID NO: 5) | QKVQDDTKTLIKT, (SEQ ID NO: 6) |
| KTLIKTIVTRIND, (SEQ ID NO: 7) | TLIKTIVTRINDI, (SEQ ID NO: 8) |
| KTIVTRINDISHT, (SEQ ID NO: 9) | TIVTRINDISHTQ, (SEQ ID NO: 10) |
| TRINDISHTQSVS, (SEQ ID NO: 11) | NDISHTQSVSSKQ, (SEQ ID NO: 12) |
| QSVSSKQKVTGLD, (SEQ ID NO: 13) | SSKQKVTGLDFIP, (SEQ ID NO: 14) |
| QKVTGLDFIPGLH, (SEQ ID NO: 15) | TGLDFIPGLHPIL, (SEQ ID NO: 16) |
| LDFIPGLHPILTL, (SEQ ID NO: 17) | DFIPGLHPILTLS, (SEQ ID NO: 18) |
| PGLHPILTLSKMD, (SEQ ID NO: 19) | GLHPILTLSKMDQ, (SEQ ID NO: 20) |
| HPILTLSKMDQTL, (SEQ ID NO: 21) | PILTLSKMDQTLA, (SEQ ID NO: 22) |
| LTLSKMDQTLAVY, (SEQ ID NO: 23) | SKMDQTLAVYQQI, (SEQ ID NO: 24) |
| QTLAVYQQILTSM, (SEQ ID NO: 25) | LAVYQQILTSMPS, (SEQ ID NO: 26) |
| AVYQQILTSMPSR, (SEQ ID NO: 27) | QQILTSMPSRNVI, (SEQ ID NO: 28) |

TABLE 1-continued

| Peptide sequences in human leptin with potential human MHC class II binding activity. | |
|---|---|
| QILTSMPSRNVIQ, (SEQ ID NO: 29) | TSMPSRNVIQISN, (SEQ ID NO: 30) |
| SRNVIQISNDLEN, (SEQ ID NO: 31) | RNVIQISNDLENL, (SEQ ID NO: 32) |
| NVIQISNDLENLR, (SEQ ID NO: 33) | IQISNDLENLRDL, (SEQ ID NO: 34) |
| NDLENLRDLLHVL, (SEQ ID NO: 35) | LENLRDLLHVLAF, (SEQ ID NO: 36) |
| ENLRDLLHVLAFS, (SEQ ID NO: 37) | RDLLHVLAFSKSC, (SEQ ID NO: 38) |
| DLLHVLAFSKSCH, (SEQ ID NO: 39) | LHVLAFSKSCHLP, (SEQ ID NO: 40) |
| HVLAFSKSCHLPW, (SEQ ID NO: 41) | LAFSKSCHLPWAS, (SEQ ID NO: 42) |
| CHLPWASGLETLD, (SEQ ID NO: 43) | SGLETLDSLGGVL, (SEQ ID NO: 44) |
| DSLGGVLEASGYS, (SEQ ID NO: 45) | SLGGVLEASGYST, (SEQ ID NO: 46) |
| GGVLEASGYSTEV, (SEQ ID NO: 47) | SGYSTEVVALSRL, (SEQ ID NO: 48) |
| TEVVALSRLQGSL, (SEQ ID NO: 49) | EVVALSRLQGSLQ, (SEQ ID NO: 50) |
| VALSRLQGSLQDM, (SEQ ID NO: 51) | SRLQGSLQDMLWQ, (SEQ ID NO: 52) |
| QGSLQDMLWQLDL, (SEQ ID NO: 53) | GSLQDMLWQLDLS, (SEQ ID NO: 54) |
| QDMLWQLDLSPGC (SEQ ID NO: 55) | |

TABLE 2

Substitutions leading to the elimination of potential T-cell epitopes of human leptin (WT = wild type).

| Residue # | WT residue | Substitutions |
|---|---|---|
| 3 | I | A C D E G H K N P Q R S T |
| 6 | V | A C D E G H K N P Q R S T |
| 13 | L | A C D E G H K N P Q R S T |
| 14 | I | A C D E G H K N P Q R S T |
| 17 | I | A C D E G H K N P Q R S T |
| 18 | V | A C D E G H K N P Q R S T |
| 21 | I | A C D E G H K N P Q R S T |
| 24 | I | A C D E G H K N P Q R S T |
| 30 | V | A C D E G H K N P Q R S T |
| 36 | V | A C D E G H K N P Q R S T |
| 39 | L | A C D E G H K N P Q R S T |
| 41 | F | A C D E G H K N P Q R S T |
| 42 | I | A C D E G H K N P Q R S T |
| 45 | L | A C D E G H K N P Q R S T |
| 48 | I | A C D E G H K N P Q R S T |
| 49 | L | A C D E G H K N P Q R S T |
| 51 | L | A C D E G H K N P Q R S T |
| 54 | M | A C D E G H K N P Q R S T |

TABLE 2-continued

Substitutions leading to the elimination of potential T-cell epitopes of human leptin (WT = wild type).

| Residue # | WT residue | Substitutions |
|---|---|---|
| 58 | L | A C D E G H K N P Q R S T |
| 60 | V | A C D E G H K N P Q R S T |
| 61 | Y | A C D E G H K N P Q R S T |
| 64 | I | A C D E G H K N P Q R S T |
| 65 | L | A C D E G H K N P Q R S T |
| 68 | M | A C D E G H K N P Q R S T |
| 73 | V | A C D E G H K N P Q R S T |
| 74 | I | A C D E G H K N P Q R S T |
| 76 | I | A C D E G H K N P Q R S T |
| 80 | L | A C D E G H K N P Q R S T |
| 83 | L | A C D E G H K N P Q R S T |
| 86 | L | A C D E G H K N P Q R S T |
| 87 | L | A C D E G H K N P Q R S T |
| 89 | V | A C D E G H K N P Q R S T |
| 90 | L | A C D E G H K N P Q R S T |
| 92 | F | A C D E G H K N P Q R S T |
| 98 | L | A C D E G H K N P Q R S T |

TABLE 2-continued

| Substitutions leading to the elimination of potential T-cell epitopes of human leptin (WT = wild type). | | |
|---|---|---|
| Residue # | WT residue | Substitutions |
| 100 | W | A C D E G H K N P Q R S T |
| 104 | L | A C D E G H K N P Q R S T |
| 107 | L | A C D E G H K N P Q R S T |
| 110 | L | A C D E G H K N P Q R S T |
| 113 | V | A C D E G H K N P Q R S T |
| 114 | L | A C D E G H K N P Q R S T |
| 119 | Y | A C D E G H K N P Q R S T |
| 123 | V | A C D E G H K N P Q R S T |
| 124 | V | A C D E G H K N P Q R S T |
| 126 | L | A C D E G H K N P Q R S T |
| 129 | L | A C D E G H K N P Q R S T |
| 133 | L | A C D E G H K N P Q R S T |
| 136 | M | A C D E G H K N P Q R S T |

Any of the above-cited peptide sequences can be used for modifying by exchanging one or more amino acids to obtain a sequence having a reduced or no immunogenicity.

EXAMPLE 3

De-Immunized Forms of Fc-IL-1Ra

The present invention provides for modified forms of an interleukin-1 receptor antagonist (IL-1Ra) with one or more T-cell epitopes removed. IL-1 is an important inflammatory and immune modulating cytokine with pleiotropic effects on a variety of tissues but may contribute to the pathology associated with rheumatoid arthritis and other diseases associated with local tissue damage. An IL-1 receptor antagonist able to inhibit the action of IL-1 has been purified and the gene cloned [Eisenburg S. P. et al., *Nature,* 343:341-346 (1990); Carter, D. B. et al., *Nature,* 344:633-637 (1990)]. Others have provided IL-1Ra molecules [e.g. U.S. Pat. No. 5,075,222]. Recombinant forms of this protein have therapeutic potential in disease settings where the effects of IL-1 are deleterious. However, there remains a continued need for IL-1Ra analogues with enhanced properties. Desired enhancements include alternative schemes and modalities for the expression and purification of the said therapeutic, but also and especially, improvements in the biological properties of the protein. There is a particular need for enhancement of the in vivo characteristics when administered to the human subject. In this regard, it is highly desired to provide IL-1Ra with reduced or absent potential to induce an immune response in the human subject. Such proteins would expect to display an increased circulation time within the human subject and would be of particular benefit in chronic or recurring disease settings such as is the case for a number of indications for IL-1Ra. The present invention provides for modified forms of IL-1Ra proteins that are expected to display enhanced properties in vivo. This disclosure specifically pertains a human IL-1Ra protein being of 152 amino acid residues (Eisenburg, S. P. et al., *Proc. Natl. Acad. Sci. U.S.A.* 88:5232-5236 (1991)).

Specific Fc-IL-1Ra forms: Fcγ1-IL-1Ra, Fcγ2-IL-1Ra, both forms, preferably with linker peptide and optionally modified Fc domain having reduced affinity to Fc-receptors.

Peptide sequences in human interleukin-1 receptor antagonist (IL-1RA) with potential human MHC class II binding activity are shown in Table 3.

TABLE 3

| Potential human MHC Class II binding sequences. | |
|---|---|
| RKSSKMQAFRIWD, (SEQ ID NO: 56) | SKMQAFRIWDVNQ, (SEQ ID NO: 57) |
| QAFRIWDVNQKTF, (SEQ ID NO: 58) | FRIWDVNQKTFYL, (SEQ ID NO: 59) |
| RIWDVNQKTFYLR, (SEQ ID NO: 60) | IWDVNQKTFYLRN, (SEQ ID NO: 61) |
| WDVNQKTFYLRNN, (SEQ ID NO: 62) | KTFYLRNNQLVAG, (SEQ ID NO: 63) |
| TFYLRNNQLVAGY, (SEQ ID NO: 64) | FYLRNNQLVAGYL, (SEQ ID NO: 65) |
| LRNNQLVAGYLQG, (SEQ ID NO: 66) | RNNQLVAGYLQGP, (SEQ ID NO: 67) |
| NQLVAGYLQGPNV, (SEQ ID NO: 68) | QLVAGYLQGPNVN, (SEQ ID NO: 69) |
| LVAGYLQGPNVNL, (SEQ ID NO: 70) | AGYLQGPNVNLEE, (SEQ ID NO: 71) |
| GYLQGPNVNLEEK, (SEQ ID NO: 72) | PNVNLEEKIDVVP, (SEQ ID NO: 73) |
| VNLEEKIDVVPIE, (SEQ ID NO: 74) | EKIDVVPIEPHAL, (SEQ ID NO: 75) |
| IDVVPIEPHALFL, (SEQ ID NO: 76) | DVVPIEPHALFLG, (SEQ ID NO: 77) |
| VPIEPHALFLGIH, (SEQ ID NO: 78) | HALFLGIHGGKMC, (SEQ ID NO: 79) |
| ALFLGIHGGKMCL, (SEQ ID NO: 80) | LFLGIHGGKMCLS, (SEQ ID NO: 81) |

TABLE 3-continued

| Potential human MHC Class II binding sequences. | |
|---|---|
| LGIHGGKMCLSCV, (SEQ ID NO: 82) | GKMCLSCVKSGDE, (SEQ ID NO: 83) |
| MCLSCVKSGDETR, (SEQ ID NO: 84) | SCVKSGDETRLQL, (SEQ ID NO: 85) |
| ETRLQLEAVNITD, (SEQ ID NO: 86) | TRLQLEAVNITDL, (SEQ ID NO: 87) |
| LQLEAVNITDLSE, (SEQ ID NO: 88) | EAVNITDLSENRK, (SEQ ID NO: 89) |
| VNITDLSENRKQD, (SEQ ID NO: 90) | TDLSENRKQDKRF, (SEQ ID NO: 91) |
| ENRKQDKRFAFIR, (SEQ ID NO: 92) | KRFAFIRSDSGPT, (SEQ ID NO: 93) |
| FAFIRSDSGPTTS, (SEQ ID NO: 94) | AFIRSDSGPTTSF, (SEQ ID NO: 95) |
| TSFESAACPGWFL, (SEQ ID NO: 96) | SFESAACPGWFLC, (SEQ ID NO: 97) |
| PGWFLCTAMEADQ, (SEQ ID NO: 98) | WFLCTAMEADQPV, (SEQ ID NO: 99) |
| TAMEADQPVSLTN, (SEQ ID NO: 100) | QPVSLTNMPDEGV, (SEQ ID NO: 101) |
| VSLTNMPDEGVMV, (SEQ ID NO: 102) | TNMPDEGVMVTKF, (SEQ ID NO: 103) |
| PDEGVMVTKFYFQ, (SEQ ID NO: 104) | EGVMVTKFYFQED, (SEQ ID NO: 105) |
| GVMVTKFYFQEDE (SEQ ID NO: 106) | |

Substitutions leading to the elimination of potential T-cell epitopes of human interleukin-1 receptor antagonist (IL-1RA) (WT=wild type) are shown in Table 4.

TABLE 4

Potential T-cell epitopes of human interleukin-1 receptor antagonist.

| Residue # | WT Residue | Substitution |
|---|---|---|
| 10 | M | A C D E G H K N P Q R S T |
| 13 | F | A C D E G H K N P Q R S T |
| 15 | I | A C D E G H K N P Q R S T |
| 16 | W | A C D E G H K N P Q R S T |
| 18 | V | A C D E G H K N P Q R S T |
| 23 | F | A C D E G H K N P Q R S T |
| 24 | Y | A C D E G H K N P Q R S T |
| 25 | L | A C D E G H K N P Q R S T |
| 30 | L | A C D E G H K N P Q R S T |
| 31 | V | A C D E G H K N P Q R S T |
| 34 | Y | A C D E G H K N P Q R S T |
| 35 | L | A C D E G H K N P Q R S T |
| 40 | V | A C D E G H K N P Q R S T |
| 42 | L | A C D E G H K N P Q R S T |
| 46 | I | A C D E G H K N P Q R S T |
| 48 | V | A C D E G H K N P Q R S T |
| 49 | V | A C D E G H K N P Q R S T |
| 51 | I | A C D E G H K N P Q R S T |

TABLE 4-continued

Potential T-cell epitopes of human interleukin-1 receptor antagonist.

| Residue # | WT Residue | Substitution |
|---|---|---|
| 56 | L | A C D E G H K N P Q R S T |
| 57 | F | A C D E G H K N P Q R S T |
| 58 | L | A C D E G H K N P Q R S T |
| 60 | I | A C D E G H K N P Q R S T |
| 65 | M | A C D E G H K N P Q R S T |
| 67 | L | A C D E G H K N P Q R S T |
| 70 | V | A C D E G H K N P Q R S T |
| 78 | L | A C D E G H K N P Q R S T |
| 80 | L | A C D E G H K N P Q R S T |
| 83 | V | A C D E G H K N P Q R S T |
| 85 | I | A C D E G H K N P Q R S T |
| 88 | L | A C D E G H K N P Q R S T |
| 98 | F | A C D E G H K N P Q R S T |
| 100 | F | A C D E G H K N P Q R S T |
| 101 | I | A C D E G H K N P Q R S T |
| 119 | W | A C D E G H K N P Q R S T |
| 120 | F | A C D E G H K N P Q R S T |
| 121 | L | A C D E G H K N P Q R S T |
| 125 | M | A C D E G H K N P Q R S T |

TABLE 4-continued

| Potential T-cell epitopes of human interleukin-1 receptor antagonist. | | |
|---|---|---|
| Residue # | WT Residue | Substitution |
| 131 | V | A C D E G H K N P Q R S T |
| 133 | L | A C D E G H K N P Q R S T |
| 136 | M | A C D E G H K N P Q R S T |
| 141 | V | A C D E G H K N P Q R S T |
| 142 | M | A C D E G H K N P Q R S T |

EXAMPLE 4

De-Immunized Forms of Fc-BNDF

The present invention provides for modified forms of human brain-derived neurotrophic factor (BDNF) with one or more T-cell epitopes removed. BDNF is glycoprotein of the nerve growth factor family of proteins. The mature 119 amino acid glycoprotein is processed from a larger pre-cursor to yield a neutrophic factor that promotes the survival of neuronal cell populations [Jones K. R. & Reichardt, L. F., *Proc. Natl. Acad. Sci U.S.A.* 87:8060-8064 (1990)]. Others have provided modified BDNF molecules [U.S. Pat. No. 5,770,577] and approaches towards the commercial production of recombinant BDNF molecules [U.S. Pat. No. 5,986,070]. Such neuronal cells are all located either in the central nervous system or directly connected to it. Recombinant preparations of BDNF have enabled the therapeutic potential of the protein to be explored for the promotion of nerve regeneration and degenerative disease therapy.

Specific Fc-BDNF forms: Fcγ1-BDNF, Fcγ2-BDNF, both forms, preferably with linker peptide and optionally modified Fc domain having reduced affinity to Fc-receptors. Peptide sequences in human brain-derived neurotrophic factor (BDNF) with potential human MHC class II binding activity are shown in Table 5.

TABLE 5

| Potential T-cell epitopes of human brain-derived nuerotrophic factor. | |
|---|---|
| GELSVCDSISEWV, (SEQ ID NO: 107) | LSVCDSISEWVTA, (SEQ ID NO: 108) |
| DSISEWVTAADKK, (SEQ ID NO: 109) | SEWVTAADKKTAV, (SEQ ID NO: 110) |
| EWVTAADKKTAVD, (SEQ ID NO: 111) | WVTAADKKTAVDM, (SEQ ID NO: 112) |
| KTAVDMSGGTVTV, (SEQ ID NO: 113) | TAVDMSGGTVTVL, (SEQ ID NO: 114) |
| VDMSGGTVTVLEK, (SEQ ID NO: 115) | GTVTVLEKVPVSK, (SEQ ID NO: 116) |
| VTVLEKVPVSKGQ, (SEQ ID NO: 117) | TVLEKVPVSKGQL, (SEQ ID NO: 118) |
| EKVPVSKGQLKQY, (SEQ ID NO: 119) | VPVSKGQLKQYFY, (SEQ ID NO: 120) |
| GQLKQYFYETKCN, (SEQ ID NO: 121) | KQYFYETKCNPM, (SEQ ID NO: 122) |
| QYFYETKCNPMGY, (SEQ ID NO: 123) | YFYETKCNPMGYT, (SEQ ID NO: 124) |
| NPMGYTKEGCRGI, (SEQ ID NO: 125) | MGYTKEGCRGIDK, (SEQ ID NO: 126) |
| RGIDKRHWNSQCR, (SEQ ID NO: 127) | RHWNSQCRTTQSY, (SEQ ID NO: 128) |
| HWNSQCRTTQSYV, (SEQ ID NO: 129) | QSYVRALTMDSKK, (SEQ ID NO: 130) |
| SYVRALTMDSKKR, (SEQ ID NO: 131) | RALTMDSKKRIGW, (SEQ ID NO: 132) |
| LTMDSKKRIGWRF, (SEQ ID NO: 133) | KRIGWRFIRIDTS, (SEQ ID NO: 134) |
| IGWRFIRIDTSCV, (SEQ ID NO: 135) | GWRFIRIDTSCVC, (SEQ ID NO: 136) |
| WRFIRIDTSCVCT, (SEQ ID NO: 137) | RFIRIDTSCVCTL, (SEQ ID NO: 138) |
| IRIDTSCVCTLTI, (SEQ ID NO: 139) | IDTSCVCTLTIKR (SEQ ID NO: 140) |

Substitutions leading to the elimination of potential T-cell epitopes of human brain-derived neurotrophic factor (BDNF) (WT=wild type) are shown in Table 6.

TABLE 6

Substitutions leading to elimination of potential T-cell epitopes of human brain-derived neurotrophic factor.

| Residue # | WT Residue | Substitution |
|---|---|---|
| 10 | L | A C D E G H K N P Q R S T |
| 16 | I | A C D E G H K N P Q R S T |
| 20 | V | A C D E G H K N P Q R S T |
| 29 | V | A C D E G H K N P Q R S T |
| 31 | M | A C D E G H K N P Q R S T |
| 36 | V | A C D E G H K N P Q R S T |
| 38 | V | A C D E G H K N P Q R S T |
| 39 | L | A C D E C H K N P Q R S T |
| 42 | V | A C D E G H K N P Q R S T |
| 44 | V | A C D E G H K N P Q R S T |
| 49 | L | A C D E G H K N P Q R S T |
| 52 | Y | A C D E G H K N P Q R S T |
| 53 | F | A C D E G H K N P Q R S T |
| 54 | Y | A C D E G H K N P Q R S T |
| 61 | M | A C D E G H K N P Q R S T |
| 63 | Y | A C D E G H K N P Q R S T |
| 71 | I | A C D E G H K N P Q R S T |
| 76 | W | A C D E G H K N P Q R S T |
| 86 | Y | A C D E G H K N P Q R S T |
| 87 | V | A C D E G H K N P Q R S T |
| 90 | L | A C D E G H K N P Q R S T |
| 92 | M | A C D E G H K N P Q R S T |
| 98 | I | A C D E G H K N P Q R S T |

TABLE 6-continued

Substitutions leading to elimination of potential T-cell epitopes of human brain-derived neurotrophic factor.

| Residue # | WT Residue | Substitution |
|---|---|---|
| 100 | W | A C D E G H K N P Q R S T |
| 102 | F | A C D E C H K N P Q R S T |
| 103 | I | A C D E G H K N P Q R S T |
| 105 | I | A C D E G H K N P Q R S T |

EXAMPLE 5

De-Immunized Forms of Fc-EPO

The present invention provides for modified forms of human erythropioetin (EPO) with one or more T-cell epitopes removed. EPO is a 165 amino acid residues glycoprotein hormone involved in the maturation of erythroid progenitor cells into erythrocytes. Naturally occurring EPO is produced by the liver during foetal life and by the kidney of adults and circulates in the blood to stimulate production of red blood cells in bone marrow. Anaemia is almost invariably a consequence of renal failure due to decreased production of EPO from the kidney. Recombinant EPO is used as an effective treatment of anaemia resulting from chronic renal failure.

Recombinant EPO (expressed in mammalian cells) having the amino acid sequence 1-165 of human erythropoietin [Jacobs, K. et al., Nature, 313:806-810 (1985); Lin, F. K. et al., *Proc. Natl. Acad. Sci. U.S.A.* 82:7580-7585 (1985)] contains three N-linked and one O-linked oligosaccharide chains each containing terminal sialic acid residues. The latter are significant in enabling EPO to evade rapid clearance from the circulation by the hepatic asialoglycoprotein binding protein.

Non-de-immunized Fc-EPO is known e.g. from WO 99/58662, WO 99/02709. Specific Fc-EPO forms are: Fcγ1-EPO, Fcγ2-EPO, both forms, preferably having a linker peptide and optionally a modified Fc domain having reduced affinity to Fc-receptors. The EPO may be glycosylated, partially glycosylated or have a modified glycosylation pattern.

Peptide sequences in human erythropoietin (EPO) with potential human MHC class II binding activity are shown in Table 7.

TABLE 7

| Potential T-cell epitopes of human erythropoietin. | |
|---|---|
| PRLICDSRVLERY, (SEQ ID NO: 141) | RLICDSRVLERYL, (SEQ ID NO: 142) |
| ICDSRVLERYLLE, (SEQ ID NO: 143) | CDSRVLERYLLEA, (SEQ ID NO: 144) |
| SRVLERYLLEAKE, (SEQ ID NO: 145) | RVLERYLLEAKEA, (SEQ ID NO: 146) |
| LERYLLEAKEAEN, (SEQ ID NO: 147) | ERYLLEAKEAENI, (SEQ ID NO: 148) |
| RYLLEAKEAENIT, (SEQ ID NO: 149) | YLLEAKEAENITT, (SEQ ID NO: 150) |
| LEAKEAENITTGC, (SEQ ID NO: 151) | KEAENITTGCAEH, (SEQ ID NO: 152) |
| ENITTGCAEHCSL, (SEQ ID NO: 153) | CSLNENITVPDTK, (SEQ ID NO: 154) |
| NENITVPDTKVNF, (SEQ ID NO: 155) | ENITVPDTKVNFY, (SEQ ID NO: 156) |

TABLE 7-continued

| Potential T-cell epitopes of human erythropoietin. |
|---|
| NITVPDTKVNFYA, (SEQ ID NO: 157) ITVPDTKVNFYAW, (SEQ ID NO: 158) |
| TKVNFYAWKRMEV, (SEQ ID NO: 159) VNFYAWKRMEVGQ, (SEQ ID NO: 160) |
| NFYAWKRMEVGQQ, (SEQ ID NO: 161) YAWKRMEVGQQAV, (SEQ ID NO: 162) |
| KRMEVGQQAVEVW, (SEQ ID NO: 163) RMEVGQQAVEVWQ, (SEQ ID NO: 164) |
| MEVGQQAVEVWQG, (SEQ ID NO: 165) QAVEVWQGLALLS, (SEQ ID NO: 166) |
| AVEVWQGLALLSE, (SEQ ID NO: 167) VEVWQGLALLSEA, (SEQ ID NO: 168) |
| EVWQGLALLSEAV, (SEQ ID NO: 169) VWQGLALLSEAVL, (SEQ ID NO: 170) |
| WQGLALLSEAVLR, (SEQ ID NO: 171) QGLALLSEAVLRG, (SEQ ID NO: 172) |
| LALLSEAVLRGQA, (SEQ ID NO: 173) ALLSEAVLRGQAL, (SEQ ID NO: 174) |
| LSEAVLRGQALLV, (SEQ ID NO: 175) SEAVLRGQALLVN, (SEQ ID NO: 176) |
| EAVLRGQALLVNS, (SEQ ID NO: 177) AVLRGQALLVNSS, (SEQ ID NO: 178) |
| QALLVNSSQPWEP, (SEQ ID NO: 179) ALLVNSSQPWEPL, (SEQ ID NO: 180) |
| LLVNSSQPWEPLQ, (SEQ ID NO: 181) QPWEPLQLHVDKA, (SEQ ID NO: 182) |
| EPLQLHVDKAVSG, (SEQ ID NO: 183) LQLHVDKAVSGLR, (SEQ ID NO: 184) |
| LHVDKAVSGLRSL, (SEQ ID NO: 185) KAVSGLRSLTTLL, (SEQ ID NO: 186) |
| SGLRSLTTLLRAL, (SEQ ID NO: 187) RSLTTLLRALGAQ, (SEQ ID NO: 188) |
| SLTTLLRALGAQK, (SEQ ID NO: 189) TTLLRALGAQKEA, (SEQ ID NO: 190) |
| TLLRALGAQKEAI, (SEQ ID NO: 191) RALGAQKEAISPP, (SEQ ID NO: 192) |
| AQKEAISPPDAAS, (SEQ ID NO: 193) EAISPPDAASAAP, (SEQ ID NO: 194) |
| SPPDAASAAPLRT, (SEQ ID NO: 195) ASAAPLRTITADT, (SEQ ID NO: 196) |
| APLRTITADTFRK, (SEQ ID NO: 197) RTITADTFRKLFR, (SEQ ID NO: 198) |
| TITADTFRKLFRV, (SEQ ID NO: 199) DTFRKLFRVYSNF, (SEQ ID NO: 200) |
| RKLFRVYSNFLRG, (SEQ ID NO: 201) KLFRVYSNFLRGK, (SEQ ID NO: 202) |
| FRVYSNFLRGKLK, (SEQ ID NO: 203) RVYSNFLRGKLKL, (SEQ ID NO: 204) |
| YSNFLRGKLKLYT, (SEQ ID NO: 205) SNFLRGKLKLYTG, (SEQ ID NO: 206) |
| NFLRGKLKLYTGE, (SEQ ID NO: 207) RGKLKLYTGEACR, (SEQ ID NO: 208) |
| GKLKLYTGEACRT, (SEQ ID NO: 209) LKLYTGEACRTGD, (SEQ ID NO: 210) |
| KLYTGEACRTGDR (SEQ ID NO: 211) |

Substitutions leading to the elimination of potential T-cell epitopes of human erythropoietin (EPO) (WT=wild type) are shown in Table 8.

TABLE 8

Substitutions leading to elimination of potential T-cell epitopes of human EPO.

| Residue # | WT residue | Substitutions |
|---|---|---|
| 5 | L | A C D E G H K N P Q R S T |
| 6 | I | A C D E G H K N P Q R S T |

TABLE 8-continued

Substitutions leading to elimination of potential T-cell epitopes of human EPO.

| Residue # | WT residue | Substitutions |
|---|---|---|
| 11 | V | A C D E G H K N P Q R S T |
| 12 | L | A C D E G H K N P Q R S T |
| 15 | Y | A C D E G H K N P Q R S T |
| 16 | L | A C D E G H K N P Q R S T |

TABLE 8-continued

Substitutions leading to elimination of potential T-cell epitopes of human EPO.

| Residue # | WT residue | Substitutions |
|---|---|---|
| 17 | L | A C D E G H K N P Q R S T |
| 25 | I | A C D E G H K N P Q R S T |
| 35 | L | A C D E G H K N P Q R S T |
| 39 | I | A C D E G H K N P Q R S T |
| 41 | V | A C D E G H K N P Q R S T |
| 46 | V | A C D E G H K N P Q R S T |
| 48 | F | A C D E G H K N P Q R S T |
| 49 | Y | A C D E G H K N P Q R S T |
| 51 | W | A C D E G H K N P Q R S T |
| 54 | M | A C D E G H K N P Q R S T |
| 56 | V | A C D E G H K N P Q R S T |
| 61 | V | A C D E G H K N P Q R S T |
| 63 | V | A C D E G H K N P Q R S T |
| 64 | W | A C D E G H K N P Q R S T |
| 67 | L | A C D E G H K N P Q R S T |
| 69 | L | A C D E G H K N P Q R S T |
| 70 | L | A C D E G H K N P Q R S T |
| 74 | V | A C D E G H K N P Q R S T |
| 75 | L | A C D E G H K N P Q R S T |
| 80 | L | A C D E G H K N P Q R S T |
| 81 | L | A C D E G H K N P Q R S T |
| 82 | N | A C D E G H K N P Q R S T |
| 88 | W | A C D E G H K N P Q R S T |
| 91 | L | A C D E G H K N P Q R S T |
| 93 | L | A C D E G H K N P Q R S T |
| 95 | V | A C D E G H K N P Q R S T |
| 99 | V | A C D E G H K N P Q R S T |
| 102 | L | A C D E G H K N P Q R S T |
| 105 | L | A C D E G H K N P Q R S T |
| 108 | L | A C D E G H K N P Q R S T |
| 109 | L | A C D E G H K N P Q R S T |
| 112 | L | A C D E G H K N P Q R S T |
| 119 | I | A C D E G H K N P Q R S T |
| 130 | L | A C D E G H K N P Q R S T |
| 133 | I | A C D E G H K N P Q R S T |
| 138 | F | A C D E G H K N P Q R S T |
| 141 | L | A C D E G H K N P Q R S T |

TABLE 8-continued

Substitutions leading to elimination of potential T-cell epitopes of human EPO.

| Residue # | WT residue | Substitutions |
|---|---|---|
| 142 | F | A C D E G H K N P Q R S T |
| 144 | V | A C D E G H K N P Q R S T |
| 145 | Y | A C D E G H K N P Q R S T |
| 148 | F | A C D E G H K N P Q R S T |
| 149 | L | A C D E G H K N P Q R S T |
| 153 | L | A C D E G H K N P Q R S T |
| 155 | L | A C D E G H K N P Q R S T |
| 156 | Y | A C D E G H K N P Q R S T |

EXAMPLE 6

De-Immunized Forms of G-CSF

The present invention provides for modified forms of human granulocyte colony stimulating factor (G-CSF) with one or more T-cell epitopes removed. G-CSF is an important haemopoietic cytokine currently used in treatment of indications where an increase in blood neutrophils will provide benefits. These include cancer therapy, various infectious diseases and related conditions such as sepsis. G-CSF is also used alone, or in combination with other compounds and cytokines in the ex vivo expansion of haemopoietic cells for bone marrow transplantation.

Two forms of human G-CSF are commonly recognized for this cytokine. One is a protein of 177 amino acids, the other a protein of 174 amino acids [Nagata et al., EMBO J. 5:575-581 (1986)], the 174 amino acid form has been found to have the greatest specific in vivo biological activity. Recombinant DNA techniques have enabled the production of commercial scale quantities of G-CSF exploiting both eukaryotic and prokaryotic host cell expression systems. This disclosure specifically pertains to both recognized forms of the human G-CSF protein being the 177 amino acid species and the 174 amino acid species. Other polypeptide analogues and peptide fragments of G-CSF have been previously disclosed, including forms modified by site-specific amino acid substitutions and or by modification by chemical adducts. Thus U.S. Pat. No. 4,810,643 discloses analogues with the particular Cys residues replaced with another amino acid, and G-CSF with an Ala residue in the first (N-terminal) position. EP 0 335 423 discloses the modification of at least one amino group in a polypeptide having G-CSF activity. EP 0 272 703 discloses G-CSF derivatives having amino acid substituted or deleted near the N-terminus. EP 0 459 630 discloses G-CSF derivatives in which Cys 17 and Asp 27 are replaced by Ser residues. EP 0 243 153 discloses G-CSF modified by inactivating at least one yeast KEX2 protease processing site for increased yield in recombinant production and U.S. Pat. No. 4,904,584 discloses lysine altered proteins. WO 90/12874 discloses further Cys altered variants and Australian patent document AU 10948/92 discloses the addition of amino acids to either terminus of a G-CSF molecule for the purpose of aiding in the folding of the molecule after prokaryotic expression. A further Australian document, AU 76380/91, discloses G-CSF variants at positions 50-56 of the G-CSF 174 amino acid form, and positions 53-59 of the 177 amino acid form. Additional changes at particular His residues were also disclosed.

Non-deimmunized Fc-G-CSF is known e.g. from WO 99/58662. Specific Fc-G-CSF forms: Fcγ1-G-CSF, Fcγ2-G-CSF, both forms, preferably with linker peptide and optionally modified Fc domain having reduced affinity to Fc-receptors.

Peptide sequences in human granulocyte colony stimulating factor (G-CSF) with potential human MHC class II binding activity are shown in Table 9.

TABLE 9

| Potential T-cell epitopes of human G-CSF. | |
|---|---|
| TPLGPASSLPQSF, (SEQ ID NO: 212) | SSLPQSFLLKCLE, (SEQ ID NO: 106) |
| QSFLLKCLEQVRK, (SEQ ID NO: 214) | SFLLKCLEQVRKI, (SEQ ID NO: 106) |
| FLLKCLEQVRKIQ, (SEQ ID NO: 216) | KCLEQVRKIQGDG, (SEQ ID NO: 106) |
| EQVRKIQGDGAAL, (SEQ ID NO: 218) | RKIQGDGAALQEK, (SEQ ID NO: 106) |
| AALQEKLVSECAT, (SEQ ID NO: 220) | EKLVSECATYKLC, (SEQ ID NO: 106) |
| KLVSECATYKLCH, (SEQ ID NO: 222) | AALQEKLCATYKL, (SEQ ID NO: 106) |
| EKLCATYKLCHPE, (SEQ ID NO: 224) | ATYKLCHPEELVL, (SEQ ID NO: 106) |
| YKLCHPEELVLLG, (SEQ ID NO: 226) | EELVLLGHSLGIP, (SEQ ID NO: 106) |
| ELVLLGHSLGIPW, (SEQ ID NO: 228) | HSLGIPWAPLSSC, (SEQ ID NO: 106) |
| IPWAPLSSCPSQA, (SEQ ID NO: 230) | APLSSCPSQALQL, (SEQ ID NO: 106) |
| QALQLAGCLSQLH, (SEQ ID NO: 232) | GCLSQLHSGLFLY, (SEQ ID NO: 106) |
| SQLHSGLFLYQGL, (SEQ ID NO: 234) | SGLFLYQGLLQAL, (SEQ ID NO: 106) |
| GLFLYQGLLQALE, (SEQ ID NO: 236) | LFLYQGLLQALEG, (SEQ ID NO: 106) |
| FLYQGLLQALEGI, (SEQ ID NO: 238) | QGLLQALEGISPE, (SEQ ID NO: 106) |
| GLLQALEGISPEL, (SEQ ID NO: 240) | QALEGISPELGPT, (SEQ ID NO: 106) |
| EGISPELGPTLDT, (SEQ ID NO: 242) | PTLDTLQLDVADF, (SEQ ID NO: 106) |
| DTLQLDVADFATT, (SEQ ID NO: 244) | LQLDVADFATTIW, (SEQ ID NO: 106) |
| LDVADFATTIWQQ, (SEQ ID NO: 246) | TTIWQQMEELGMA, (SEQ ID NO: 106) |
| TIWQQMEELGMAP, (SEQ ID NO: 248) | QQMEELGMAPALQ, (SEQ ID NO: 106) |
| EELGMAPALQPTQ, (SEQ ID NO: 250) | LGMAPALQPTQGA, (SEQ ID NO: 106) |
| PALQPTQGANPAF, (SEQ ID NO: 252) | GAMPAFASAFQRR, (SEQ ID NO: 106) |
| PAFASAFQRRAGG, (SEQ ID NO: 254) | SAFQRRAGGVLVA, (SEQ ID NO: 106) |
| GGVLVASHLQSFL, (SEQ ID NO: 256) | GVLVASHLQSFLE, (SEQ ID NO: 106) |
| VLVASHLQSFLEV, (SEQ ID NO: 258) | SHLQSFLEVSYRV, (SEQ ID NO: 106) |
| QSFLEVSYRVLRH, (SEQ ID NO: 260) | SFLEVSYRVLRHL, (SEQ ID NO: 106) |
| LEVSYRVLRHLAQ (SEQ ID NO: 262) | |

Substitutions leading to the elimination of potential T-cell epitopes of human granulocyte colony stimulating factor (G-CSF) (WT=wild type) are shown in Table 10.

TABLE 10

Substitutions leading to elimination of potential T-cell epitopes of Human G-CSF.

| Residue # | WT Residue | Substitution |
|---|---|---|
| 3 | L | A C D E G H K N P Q R S T |
| 9 | L | A C D E G H K N P Q R S T |
| 14 | L | A C D E G H K N P Q R S T |
| 15 | L | A C D E G H K N P Q R S T |
| 18 | L | A C D E G H K N P Q R S T |
| 21 | V | A C D E G H K N P Q R S T |
| 24 | I | A C D E G H K N P Q R S T |
| 31 | L | A C D E G H K N P Q R S T |
| 35 | L | A C D E G H K N P Q R S T |
| 39 | Y | A C D E G H K N P Q R S T |
| 41 | L | A C D E G H K N P Q R S T |
| 47 | L | A C D E G H K N P Q R S T |
| 48 | V | A C D E G H K N P Q R S T |
| 49 | L | A C D E G H K N P Q R S T |
| 50 | L | A C D E G H K N P Q R S T |
| 54 | L | A C D E G H K N P Q R S T |
| 56 | I | A C D E G H K N P Q R S T |
| 58 | W | A C D E G H K N P Q R S T |
| 61 | L | A C D E G H K N P Q R S T |
| 69 | L | A C D E G H K N P Q R S T |
| 71 | L | A C D E G H K N P Q R S T |
| 75 | L | A C D E G H K N P Q R S T |
| 78 | L | A C D E G H K N P Q R S T |
| 82 | L | A C D E G H K N P Q R S T |
| 83 | F | A C D E G H K N P Q R S T |
| 84 | L | A C D E G H K N P Q R S T |
| 85 | Y | A C D E G H K N P Q R S T |
| 88 | L | A C D E G H K N P Q R S T |
| 89 | L | A C D E G H K N P Q R S T |
| 92 | L | A C D E G H K N P Q R S T |
| 95 | I | A C D E G H K N P Q R S T |
| 99 | L | A C D E G H K N P Q R S T |
| 103 | L | A C D E G H K N P Q R S T |
| 106 | L | A C D E G H K N P Q R S T |
| 108 | L | A C D E G H K N P Q R S T |

TABLE 10-continued

Substitutions leading to elimination of potential T-cell epitopes of Human G-CSF.

| Residue # | WT Residue | Substitution |
|---|---|---|
| 110 | V | A C D E G H K N P Q R S T |
| 113 | F | A C D E G H K N P Q R S T |
| 117 | I | A C D E G H K N P Q R S T |
| 118 | W | A C D E G H K N P Q R S T |
| 121 | M | A C D E G H K N P Q R S T |
| 124 | L | A C D E G H K N P Q R S T |
| 130 | L | A C D E G H K N P Q R S T |
| 137 | M | A C D E G H K N P Q R S T |
| 140 | F | A C D E G H K N P Q R S T |
| 144 | F | A C D E G H K N P Q R S T |
| 151 | V | A C D E G H K N P Q R S T |
| 152 | L | A C D E G H K N P Q R S T |
| 153 | V | A C D E G H K N P Q R S T |
| 157 | L | A C D E G H K N P Q R S T |
| 160 | F | A C D E G H K N P Q R S T |
| 161 | L | A C D E G H K N P Q R S T |
| 163 | V | A C D E G H K N P Q R S T |

EXAMPLE 7

De-Immunized Forms of KGF

The present invention provides for modified forms of human keratinocyte growth factor (KGF) with one or more T-cell epitopes removed. KGF is a member of the fibroblast growth factor (FGF)/heparin-binding growth factor family of proteins. It is a secreted glycoprotein expressed predominantly in the lung, promoting wound healing by stimulating the growth of keratinocytes and other epithelial cells [Finch et al., Science 24:752-755 (1989); Rubin et al., *Proc. Natl. Acad. Sci. U.S.A.* 86:802-806 (1989)]. The mature (processed) form of the glycoprotein comprises 163 amino acid residues and may be isolated from conditioned media following culture of particular cell lines [Rubin et al., (1989) ibid.], or produced using recombinant techniques [Ron et al., J. Biol. Chem. 268:2984-2988 (1993)]. The protein is of therapeutic value for the stimulation of epithelial cell growth in a number of significant disease and injury repair settings. This disclosure specifically pertains the human KGF protein being the mature (processed) form of 163 amino acid residues. Others have also provided KGF molecules [e.g. U.S. Pat. No. 6,008,328; WO 90/08771;] including modified KGF [Ron et al., (1993) ibid; WO 95/01434] but Specific Fc-KGF forms: Fcγ1-KGF, Fcγ2-KGF, both forms, preferably with linker peptide and optionally modified Fc domain having reduced affinity to Fc-receptors.

Peptide sequences in human keratinocyte growth factor (KGF) with potential human MHC class II binding activity are shown in Table 11.

TABLE 11

| Potential T-cell epitopes of human KGF. | |
|---|---|
| NDMTPEQMATNVN, | (SEQ ID NO: 263) |
| DMTPEQMATNVNC, | (SEQ ID NO: 264) |
| EQMATNVNCSSPE, | (SEQ ID NO: 265) |
| TNVNCSSPERHTR, | (SEQ ID NO: 266) |
| RSYDYMEGGDIRV, | (SEQ ID NO: 267) |
| YDYMEGGDIRVRR, | (SEQ ID NO: 268) |
| DYMEGGDIRVRRL, | (SEQ ID NO: 269) |
| GDIRVRRLFCRTQ, | (SEQ ID NO: 270) |
| IRVRRLFCRTQWY, | (SEQ ID NO: 271) |
| RRLFCRTQWYLRI, | (SEQ ID NO: 272) |
| RLFCRTQWYLRID, | (SEQ ID NO: 273) |
| TQWYLRIDKRGKV, | (SEQ ID NO: 274) |
| QWYLRIDKRGKVK, | (SEQ ID NO: 275) |
| WYLRIDKRGKVKG, | (SEQ ID NO: 276) |
| LRIDKRGKVKGTQ, | (SEQ ID NO: 277) |
| GKVKGTQEMKNNY, | (SEQ ID NO: 278) |
| QEMKNNYNIMEIR, | (SEQ ID NO: 279) |
| NNYNIMEIRTVAV, | (SEQ ID NO: 280) |
| YNIMEIRTVAVGI, | (SEQ ID NO: 281) |
| NIMEIRTVAVGIV, | (SEQ ID NO: 282) |
| MEIRTVAVGIVAI, | (SEQ ID NO: 283) |
| RTVAVGIVAIKGV, | (SEQ ID NO: 284) |
| VAVGIVAIKGVES, | (SEQ ID NO: 285) |
| VGIVAIKGVESEF, | (SEQ ID NO: 286) |
| VAIKGVESEFYLA, | (SEQ ID NO: 287) |
| KGVESEFYLAMNK, | (SEQ ID NO: 288) |
| SEFYLAMNKEGKL, | (SEQ ID NO: 289) |
| EFYLAMNKEGKLY, | (SEQ ID NO: 290) |
| FYLAMNKEGKLYA, | (SEQ ID NO: 291) |
| LAMNKEGKLYAKK, | (SEQ ID NO: 292) |
| GKLYAKKECNEDC, | (SEQ ID NO: 293) |
| KLYAKKECNEDCN, | (SEQ ID NO: 294) |
| CNFKELILENHYN, | (SEQ ID NO: 295) |
| KELILENHYNTYA, | (SEQ ID NO: 296) |
| ELILENHYNTYAS, | (SEQ ID NO: 297) |
| LILENHYNTYASA, | (SEQ ID NO: 298) |
| NHYNTYASAKWTH, | (SEQ ID NO: 299) |

TABLE 11-continued

| Potential T-cell epitopes of human KGF. | |
|---|---|
| NTYASAKWTHNGG, | (SEQ ID NO: 300) |
| AKWTHNGGEMFVA, | (SEQ ID NO: 301) |
| GEMFVALNQKGIP, | (SEQ ID NO: 302) |
| EMFVALNQKGIPV, | (SEQ ID NO: 303) |
| FVALNQKGIPVRG, | (SEQ ID NO: 304) |
| VALNQKGIPVRGK, | (SEQ ID NO: 305) |
| KGIPVRGKKTKKE, | (SEQ ID NO: 306) |
| IPVRGKKTKKEQK, | (SEQ ID NO: 307) |
| KTKKEQKTAHFLP | (SEQ ID NO: 308) |

Substitutions leading to the elimination of potential T-cell epitopes of human keratinocyte growth factor (KGF) (WT=wild type) are shown in Table 12.

TABLE 12

Substitutions leading to elimination of potential T-cell epitopes of human KGF.

| Residue # | WT residue | Substitution |
|---|---|---|
| 5 | M | A C D E G H K N P Q R S T |
| 10 | M | A C D E G H K N P Q R S T |
| 14 | V | A C D E G H K N P Q R S T |
| 26 | Y | A C D E G H K N P Q R S T |
| 28 | Y | A C D E G H K N P Q R S T |
| 29 | M | A C D E G H K N P Q R S T |
| 34 | I | A C D E G H K N P Q R S T |
| 36 | V | A C D E G H K N P Q R S T |
| 39 | L | A C D E G H K N P Q R S T |
| 40 | F | A C D E G H K N P Q R S T |
| 45 | W | A C D E G H K N P Q R S T |
| 46 | Y | A C D E G H K N P Q R S T |
| 47 | L | A C D E G H K N P Q R S T |
| 49 | I | A C D E G H K N P Q R S T |
| 55 | V | A C D E G H K N P Q R S T |
| 61 | M | A C D E G H K N P Q R S T |
| 65 | Y | A C D E G H K N P Q R S T |
| 67 | I | A C D E G H K N P Q R S T |
| 68 | M | A C D E G H K N P Q R S T |
| 70 | I | A C D E G H K N P Q R S T |
| 73 | V | A C D E G H K N P Q R S T |
| 75 | V | A C D E G H K N P Q R S T |

TABLE 12-continued

| Substitutions leading to elimination of potential T-cell epitopes of human KGF. | | |
|---|---|---|
| Residue # | WT residue | Substitution |
| 77 | I | A C D E G H K N P Q R S T |
| 78 | V | A C D E G H K N P Q R S T |
| 80 | I | A C D E G H K N P Q R S T |
| 83 | V | A C D E G H K N P Q R S T |
| 87 | F | A C D E G H K N P Q R S T |
| 88 | Y | A C D E G H K N P Q R S T |
| 89 | L | A C D E G H K N P Q R S T |
| 91 | M | A C D E G H K N P Q R S T |
| 97 | L | A C D E G H K N P Q R S T |
| 98 | Y | A C D E G H K N P Q R S T |
| 109 | F | A C D E G H K N P Q R S T |
| 112 | L | A C D E G H K N P Q R S T |
| 113 | I | A C D E G H K N P Q R S T |
| 114 | L | A C D E G H K N P Q R S T |
| 118 | Y | A C D E G H K N P Q R S T |
| 121 | Y | A C D E G H K N P Q R S T |
| 126 | W | A C D E G H K N P Q R S T |
| 133 | M | A C D E G H K N P Q R S T |
| 134 | F | A C D E G H K N P Q R S T |
| 135 | V | A C D E G H K N P Q R S T |
| 137 | L | A C D E G H K N P Q R S T |
| 142 | I | A C D E G H K N P Q R S T |
| 144 | V | A C D E G H K N P Q R S T |

EXAMPLE 8

De-Immunized sTNF-R(I) and sTNF Inhibitor within Corresponding Fc Fusions

Fc-sTNF-R(I) and Fc-sTNF Inhibitor are fusion proteins in which the serum half-life is extended compared to sTNF-R(I) and sTNF Inhibitor itself. However, certain forms of Fc-TNF-RI, such as when the Fc is derived from human IgG1 or human IgG3, have the potential to show enhanced immunogenicity under certain circumstances, such as administration by subcutaneous injection. The present invention provides for modified forms of a soluble tumor necrosis factor receptor type I (sTNF-RI) with one or more T-cell epitopes removed.

The sTNF-RI (soluble tumor necrosis factor receptor type I) is a derivative of the human tumor necrosis factor receptor described previously [Gray, P. W. et al., *Proc. Nat. Acad. Sci. U.S.A.* 87:7380-7384 (1990); Loetschere, H. et al., *Cell* 61:351-359 (1990); Schall, T. J. et al., *Cell* 61:361-370 (1990)], comprising the extracellular domain of the intact receptor and exhibiting an approximate molecular weight of 30 KDa. Additional soluble TNF inhibitors and in particular a 40 KDa form are also known [U.S. Pat. No. 6,143,866]. The soluble forms are able to bind tumor necrosis factor alpha with high affinity and inhibit the cytotoxic activity of the cytokine in vitro. Recombinant preparations of sTNF-RI are of significant therapeutic value for the treatment of diseases where an excess level of tumor necrosis factor is causing a pathogenic effect. Indications such as cachexia, sepsis and autoimmune disorders including, and in particular, rheumatoid arthritis and others may be targeted by such therapeutic preparations of sTNF-RI. Others including Brewer et al., U.S. Pat. No. 6,143,866, have provided modified sTNF-RI molecules.

Peptide sequences in a human 30 KDa sTNF-RI with potential human MHC class II binding activity are shown in Table 13.

TABLE 13

| Potential T-cell epitopes of human 30 KDa sTNF-RI. | |
|---|---|
| DSVCPQGKYIHPQ, | (SEQ ID NO: 309) |
| KYIHPQNNSICCT, | (SEQ ID NO: 310) |
| NSICCTKCHKGTY, | (SEQ ID NO: 311) |
| TYLYNDCPGPGQD, | (SEQ ID NO: 312) |
| YLYNDCPGPGQDT, | (SEQ ID NO: 313) |
| NHLRHCLSCSKCR, | (SEQ ID NO: 314) |
| HCLSCSKCRKEMG, | (SEQ ID NO: 315) |
| KEMGQVEISSCTV, | (SEQ ID NO: 316) |
| GQVEISSCTVDRD, | (SEQ ID NO: 317) |
| VEISSCTVDRDTV, | (SEQ ID NO: 318) |
| CTVDRDTVCGCRK, | (SEQ ID NO: 319) |
| DTVCGCRKNQYRH, | (SEQ ID NO: 320) |
| NQYRHYWSENLFQ, | (SEQ ID NO: 321) |
| RHYWSENLFQCFN, | (SEQ ID NO: 322) |
| HYWSENLFQCFNC, | (SEQ ID NO: 323) |
| ENLFQCFNCSLCL, | (SEQ ID NO: 324) |
| NLFQCFNCSLCLN, | (SEQ ID NO: 325) |
| QCFNCSLCLNGTV, | (SEQ ID NO: 326) |
| CSLCLNGTVHLSC, | (SEQ ID NO: 327) |
| LCLNGTVHLSCQE, | (SEQ ID NO: 328) |
| GTVHLSCQEKQNT, | (SEQ ID NO: 329) |
| VHLSCQEKQNTVC, | (SEQ ID NO: 330) |
| EKQNTVCTCHAGF, | (SEQ ID NO: 331) |
| NTVCTCHAGFFLR, | (SEQ ID NO: 332) |
| GFFLRENECVSCS, | (SEQ ID NO: 333) |
| FFLRENECVSCSN, | (SEQ ID NO: 343) |
| ECVSCSNCKKSLE, | (SEQ ID NO: 335) |
| KSLECTKLCLPQI, | (SEQ ID NO: 336) |
| TKLCLPQIENVKG, | (SEQ ID NO: 337) |

TABLE 13-continued

| Potential T-cell epitopes of human 30 KDa sTNF-RI. | |
|---|---|
| LCLPQIENVKGTE, | (SEQ ID NO: 338) |
| PQIENVKGTEDSG, | (SEQ ID NO: 339) |
| SGTTVLLPLVIFF | (SEQ ID NO: 340) |

Peptide sequences in a human 40 KDa sTNF inhibitor with potential human MHC class II binding activity are shown in Table 14.

TABLE 14

| Potential T-cell epitopes of human 40 KDa sTNF inhibitor. | |
|---|---|
| TPYAPEPGSTCRL, | (SEQ ID NO: 341) |
| CRLREYYDQTAQM, | (SEQ ID NO: 342) |
| REYYDQTAQMCCS, | (SEQ ID NO: 343) |
| EYYDQTAQMCCSK, | (SEQ ID NO: 344) |
| AQMCCSKCSPGQH, | (SEQ ID NO: 345) |
| KCSPGQHAKVFCT, | (SEQ ID NO: 346) |
| AKVFCTKTSDTVC, | (SEQ ID NO: 347) |
| KVFCTKTSDTVCD, | (SEQ ID NO: 348) |
| STYTQLWNWVPEC, | (SEQ ID NO: 349) |
| TQLWNWVPECLSC, | (SEQ ID NO: 350) |
| QLWNWVPECLSCG, | (SEQ ID NO: 351) |
| NWVPECLSCGSRC, | (SEQ ID NO: 352) |
| ECLSCGSRCSSDQ, | (SEQ ID NO: 353) |
| SRCSSDQEVTQAC, | (SEQ ID NO: 354) |
| QEVTQACTREQNR, | (SEQ ID NO: 355) |
| QNRICTCRPGWYC, | (SEQ ID NO: 356) |
| NRICTCRPGWYCA, | (SEQ ID NO: 357) |
| PGWYCALSKQEGC, | (SEQ ID NO: 358) |
| GWYCALSKQEGCR, | (SEQ ID NO: 359) |
| CALSKQEGCRLCA, | (SEQ ID NO: 360) |
| APLRKCRPGFGVA, | (SEQ ID NO: 361) |
| PGFGVARPGTETS, | (SEQ ID NO: 362) |
| FGVARPGTETSDV, | (SEQ ID NO: 363) |
| SDVVCKPCAPGTF, | (SEQ ID NO: 364) |
| GTFSNTTSSTDIC, | (SEQ ID NO: 365) |
| TDICRPHQICNVV, | (SEQ ID NO: 366) |
| HQICNVVAIPGNA, | (SEQ ID NO: 367) |
| ICNVVAIPGNASR, | (SEQ ID NO: 368) |
| CNVVAIPGNASRD, | (SEQ ID NO: 369) |
| NVVAIPGNASRDA, | (SEQ ID NO: 370) |

TABLE 14-continued

| Potential T-cell epitopes of human 40 KDa sTNF inhibitor. | |
|---|---|
| VAIPGNASRDAVC, | (SEQ ID NO: 371) |
| DAVCTSTTTPTRS, | (SEQ ID NO: 372) |
| TRSMAPGAVHLPQ, | (SEQ ID NO: 373) |
| RSMAPGAVHLPQP, | (SEQ ID NO: 374) |
| VHLPQPVSTRSQH, | (SEQ ID NO: 375) |
| QPVSTRSQHTQPT, | (SEQ ID NO: 376) |
| PEPSTAPSTSFLL, | (SEQ ID NO: 377) |
| SFLLPMGPSPPAE, | (SEQ ID NO: 378) |
| FLLPMGPSPPAEG | (SEQ ID NO: 379) |

EXAMPLE 9

(Soluble TNF-R2)

Fc-sTNF-R2 is a fusion proteins in which the serum half-life is extended compared to sTNF-R2 itself. However, certain forms of Fc-TNF-R2, such as when the Fc is derived from human IgG1 or human IgG3, have the potential to show enhanced immunogenicity under certain circumstances, such as administration by subcutaneous injection.

Soluble tumor necrosis factor receptor 2 (sTNF-R2) is a derivative of the human tumor necrosis factor receptor 2 described previously [Smith, C. A. et al., *Science* 248:1019-1023 (1990); Kohno, T. et al., *Proc. Nat. Acad. Sci. U.S.A.* 87:8331-8335 (1990); Beltinger, C. P. et al., *Genomics* 35:94-100 (1996)] comprising the extracellular domain of the intact receptor. The soluble forms are able to bind tumour necrosis factor with high affinity and inhibit the cytotoxic activity of the cytokine in vitro. Recombinant preparations of sTNF-R2 are of significant therapeutic value for the treatment of diseases where an excess level of tumour necrosis factor is causing a pathogenic effect. A particular recombinant preparation termed ethanercept has gained clinical approval for the treatment of rheumatoid arthritis and this and other similar agents may be of value in the treatment of other indications such as cachexia, sepsis and autoimmune disorders. Ethanercept is a dimeric fusion protein comprising the extracellular domain of the human TNFR2 molecule in combination with the Fc domain of the human IgG1 molecule. The dimeric molecule comprises 934 amino acids [U.S. Pat. No. 5,395,760; U.S. Pat. No. 5,605,690; U.S. Pat. No. 5,945,397].

Peptide sequences in the TNF binding domain of the human TNFR2 protein with potential human MHC class II binding activity are shown in Table 15.

TABLE 15

| Potential T-cell epitopes of human TNFR2 protein. | |
|---|---|
| TPYAPEPGSTCRL, | (SEQ ID NO: 380) |
| CRLREYYDQTAQM, | (SEQ ID NO: 381) |
| REYYDQTAQMCCS, | (SEQ ID NO: 382) |
| EYYDQTAQMCCSK, | (SEQ ID NO: 383) |

TABLE 15-continued

| Potential T-cell epitopes of human TNFR2 protein. | |
|---|---|
| AQMCCSKCSPGQH, | (SEQ ID NO: 384) |
| KCSPGQHAKVFCT, | (SEQ ID NO: 385) |
| AKVFCTKTSDTVC, | (SEQ ID NO: 386) |
| KVFCTKTSDTVCD, | (SEQ ID NO: 387) |
| STYTQLWNWVPEC, | (SEQ ID NO: 388) |
| TQLWNWVPECLSC, | (SEQ ID NO: 389) |
| QLWNWVPECLSCG, | (SEQ ID NO: 390) |
| NWVPECLSCGSRC, | (SEQ ID NO: 391) |
| ECLSCGSRCSSDQ, | (SEQ ID NO: 392) |
| SRCSSDQEVTQAC, | (SEQ ID NO: 393) |
| QEVTQACTREQNR, | (SEQ ID NO: 394) |
| QNRICTCRPGWYC, | (SEQ ID NO: 395) |
| NRICTCRPGWYCA, | (SEQ ID NO: 396) |
| PGWYCALSKQEGC, | (SEQ ID NO: 397) |
| GWYCALSKQEGCR, | (SEQ ID NO: 398) |
| CALSKQEGCRLCA, | (SEQ ID NO: 399) |
| APLRKCRPGFGVA, | (SEQ ID NO: 400) |
| PGFGVARPGTETS, | (SEQ ID NO: 401) |
| FGVARPGTETSDV, | (SEQ ID NO: 402) |
| SDVVCKPCAPGTF, | (SEQ ID NO: 403) |
| GTFSNTTSSTDIC, | (SEQ ID NO: 404) |
| TDICRPHQICNVV, | (SEQ ID NO: 405) |
| HQICNVVAIPGNA, | (SEQ ID NO: 406) |
| ICNVVAIPGNASR, | (SEQ ID NO: 407) |
| CNVVAIPGNASRD, | (SEQ ID NO: 408) |
| NVVAIPGNASRDA, | (SEQ ID NO: 409) |
| VAIPGNASRDAVC, | (SEQ ID NO: 410) |
| DAVCTSTTTPTRS, | (SEQ ID NO: 411) |
| TRSMAPGAVHLPQ, | (SEQ ID NO: 412) |
| RSMAPGAVHLPQP, | (SEQ ID NO: 413) |
| VHLPQPVSTRSQH, | (SEQ ID NO: 414) |
| QPVSTRSQHTQPT, | (SEQ ID NO: 415) |
| PEPSTAPSTSFLL, | (SEQ ID NO: 416) |
| SFLLPMGPSPPAE, | (SEQ ID NO: 417) |
| FLLPMGPSPPAEG | (SEQ ID NO: 418) |

EXAMPLE 10

Non-Natural Forms of Beta-Glucocerebrosidase (β-GCR)

Fc-β-GCR is a fusion proteins in which the serum half-life is extended compared to the β-GCR itself. However, certain forms of Fc-β-GCR, such as when the Fc is derived from human IgG1or human IgG3, have the potential to show enhanced immunogenicity under certain circumstances, such as administration by subcutaneous injection. The present invention provides for modified forms of human GCR, preferably Fc-β-GCR, with one or more T-cell epitopes removed.

Beta-Glucocerebrosidase (b-D-glucosyl-N-acylsphingosine glucohydrolase, E.C. 3.2.1.45) is a monomeric glycoprotein of 497 amino acid residues. The enzyme catalyses the hydrolysis of the glycolipid glucocerebroside to glucose and ceramide. Deficiency in GCR activity results in a lysosomal storage disease referred to as Gaucher disease. The disease is characterised by the accumulation of glucocerebroside engorged tissue macrophages that accumulate in the liver, spleen, bone marrow and other organs. The disease has varying degrees of severity from type 1 disease with haematologic problems but no neuronal involvement, to type 2 disease manifesting early after birth with extensive neuronal involvement and is universally progressive and fatal within 2 years of age. Type 3 disease is also recognised in some classifications and also shows neurologic involvement. Previously the only useful therapy for Gaucher disease has been administration of GCR derived from human placenta (known as alglucerase) but more recently pharmaceutical preparations of recombinant GCR ("Ceredase" and "Cerezyme") have shown efficacy in the treatment of type I disease [Niederau, C. et al., *Eur. J. Med. Res.* 3:25-30 (1998)].

According to the invention, the particular commercial forms of glucocerebrosidase are examined at predicted to be particularly immunogenic because these forms are engineered to have a high mannose oligosaccharide. Upon administration of such a protein, such as Ceredase or Cerezyme, the non-natural protein is preferentially bound by mannose receptors on antigen-presenting cells such as macrophages or dendritic cells. The non-natural protein is then taken up, a portion is degraded into peptides, and the peptides presented through MHC Class II to the T-cell receptor. By mutating the glucocerebrosidase sequence such that derived peptides cannot bind to MHC Class II, immunogenicity is reduced.

Others have provided GCR molecules including modified GCR [U.S. Pat. No. 5,236,838 ] but this teaching does not recognize the importance of T-cell epitopes to the immunogenic properties of the protein.

Peptide sequences in human β-GCR with potential human MHC class II binding activity are shown in Table 16.

TABLE 16

| Potential T-cell epitopes of human b-GCR. | |
|---|---|
| PCIPKSFGYSSVV, | (SEQ ID NO: 419) |
| KSFGYSSVVCVCN, | (SEQ ID NO: 420) |
| FGYSSVVCVCNAT, | (SEQ ID NO: 421) |
| SSVVCVCNATYCD, | (SEQ ID NO: 422) |
| SVVCVCNATYCDS, | (SEQ ID NO: 423) |
| VCVCNATYCDSFD, | (SEQ ID NO: 424) |

TABLE 16-continued

| Potential T-cell epitopes of human b-GCR. | |
|---|---|
| ATYCDSFDPPTFP, | (SEQ ID NO: 425) |
| DSFDPPTFPALGT, | (SEQ ID NO: 426) |
| PTFPALGTFSRYE, | (SEQ ID NO: 427) |
| PALGTFSRYESTR, | (SEQ ID NO: 428) |
| GTFSRYESTRSGR, | (SEQ ID NO: 429) |
| SRYESTRSGRRME, | (SEQ ID NO: 430) |
| GRRMELSMGPIQA, | (SEQ ID NO: 431) |
| RRMELSMGPIQAN, | (SEQ ID NO: 432) |
| RMELSMGPIQANH, | (SEQ ID NO: 433) |
| MELSMGPIQANHT, | (SEQ ID NO: 434) |
| LSMGPIQANHTGT, | (SEQ ID NO: 435) |
| MGPIQANHTGTGL, | (SEQ ID NO: 436) |
| GPIQANHTGTGLL, | (SEQ ID NO: 437) |
| TGLLLTLQPEQKF, | (SEQ ID NO: 438) |
| GLLLTLQPEQKFQ, | (SEQ ID NO: 439) |
| LLLTLQPEQKFQK, | (SEQ ID NO: 440) |
| LTLQPEQKFQKVK, | (SEQ ID NO: 441) |
| TLQPEQKFQKVKG, | (SEQ ID NO: 442) |
| PEQKFQKVKGFGG, | (SEQ ID NO: 443) |
| QKFQKVKGFGGAM, | (SEQ ID NO: 444) |
| QKVKGFGGAMTDA, | (SEQ ID NO: 445) |
| KGFGGAMTDAAAL, | (SEQ ID NO: 446) |
| GFGGAMTDAAALN, | (SEQ ID NO: 447) |
| GAMTDAAALNILA, | (SEQ ID NO: 448) |
| AMTDAAALNILAL, | (SEQ ID NO: 449) |
| MTDAAALNILALS, | (SEQ ID NO: 450) |
| AALNILALSPPAQ, | (SEQ ID NO: 451) |
| ALNILALSPPAQN, | (SEQ ID NO: 452) |
| LNILALSPPAQNL, | (SEQ ID NO: 453) |
| NILALSPPAQNLL, | (SEQ ID NO: 454) |
| LALSPPAQNLLLK, | (SEQ ID NO: 455) |
| ALSPPAQNLLLKS, | (SEQ ID NO: 456) |
| PAQNLLLKSYFSE, | (SEQ ID NO: 457) |
| AQNLLLKSYFSEE, | (SEQ ID NO: 458) |
| QNLLLKSYFSEEG, | (SEQ ID NO: 459) |
| NLLLKSYFSEEGI, | (SEQ ID NO: 460) |
| LLLKSYFSEEGIG, | (SEQ ID NO: 461) |
| KSYFSEEGIGYNI, | (SEQ ID NO: 462) |
| SYFSEEGIGYNII, | (SEQ ID NO: 463) |

TABLE 16-continued

| Potential T-cell epitopes of human b-GCR. | |
|---|---|
| FSEEGIGYNIIRV, | (SEQ ID NO: 464) |
| EGIGYNIIRVPMA, | (SEQ ID NO: 465) |
| GIGYNIIRVPMAS, | (SEQ ID NO: 466) |
| IGYNIIRVPMASC, | (SEQ ID NO: 467) |
| YNIIRVPMASCDF, | (SEQ ID NO: 468) |
| NIIRVPMASCDFS, | (SEQ ID NO: 469) |
| IIRVPMASCDFSI, | (SEQ ID NO: 470) |
| IRVPMASCDFSIR, | (SEQ ID NO: 471) |
| VPMASCDFSIRTY, | (SEQ ID NO: 472) |
| PMASCDFSIRTYT, | (SEQ ID NO: 473) |
| SCDFSIRTYTYAD, | (SEQ ID NO: 474) |
| CDFSIRTYTYADT, | (SEQ ID NO: 475) |
| FSIRTYTYADTPD, | (SEQ ID NO: 476) |
| RTYTYADTPDDFQ, | (SEQ ID NO: 477) |
| TYTYADTPDDFQL, | (SEQ ID NO: 478) |
| YTYADTPDDFQLH, | (SEQ ID NO: 479) |
| ADTPDDFQLHNFS, | (SEQ ID NO: 480) |
| PDDFQLHNFSLPE, | (SEQ ID NO: 481) |
| DDFQLHNFSLPEE, | (SEQ ID NO: 482) |
| FQLHNFSLPEEDT, | (SEQ ID NO: 483) |
| HNFSLPEEDTKLK, | (SEQ ID NO: 484) |
| FSLPEEDTKLKIP, | (SEQ ID NO: 485) |
| SLPEEDTKLKIPL, | (SEQ ID NO: 486) |
| EEDTKLKIPLIHR, | (SEQ ID NO: 487) |
| TKLKIPLIHRALQ, | (SEQ ID NO: 488) |
| KLKIPLIHPALQL, | (SEQ ID NO: 489) |
| LKIPLIHRALQLA, | (SEQ ID NO: 490) |
| IPLIHRALQLAQR, | (SEQ ID NO: 491) |
| PLIHRALQLAQRP, | (SEQ ID NO: 492) |
| HRALQLAQRPVSL, | (SEQ ID NO: 493) |
| RALQLAQRPVSLL, | (SEQ ID NO: 494) |
| ALQLAQRPVSLLA, | (SEQ ID NO: 495) |
| LQLAQRPVSLLAS, | (SEQ ID NO: 496) |
| RPVSLLASPWTSP, | (SEQ ID NO: 497) |
| PVSLLASPWTSPT, | (SEQ ID NO: 498) |
| VSLLASPWTSPTW, | (SEQ ID NO: 499) |
| SLLASPWTSPTWL, | (SEQ ID NO: 500) |
| SPWTSPTWLKTNG, | (SEQ ID NO: 501) |

TABLE 16-continued

| Potential T-cell epitopes of human b-GCR. | |
|---|---|
| TSPTWLKTNGAVN, | (SEQ ID NO: 502) |
| PTWLKTNGAVNGK, | (SEQ ID NO: 503) |
| TWLKTNGAVNGKG, | (SEQ ID NO: 504) |
| GAVNGKGSLKGQP, | (SEQ ID NO: 505) |
| GSLKGQPGDIYHQ, | (SEQ ID NO: 506) |
| GDIYHQTWARYFV, | (SEQ ID NO: 507) |
| DIYHQTWARYFVK, | (SEQ ID NO: 508) |
| QTWARYFVKFLDA, | (SEQ ID NO: 509) |
| WARYFVKFLDAYA, | (SEQ ID NO: 510) |
| ARYFVKFLDAYAE, | (SEQ ID NO: 511) |
| RYFVKFLDAYAEH, | (SEQ ID NO: 512) |
| YFVKFLDAYAEHK, | (SEQ ID NO: 513) |
| FVKFLDAYAEHKL, | (SEQ ID NO: 514) |
| VKFLDAYAEHKLQ, | (SEQ ID NO: 515) |
| KFLDAYAEHKLQF, | (SEQ ID NO: 516) |
| DAYAEHKLQFWAV, | (SEQ ID NO: 517) |
| YAEHKLQFWAVTA, | (SEQ ID NO: 518) |
| HKLQFWAVTAENE, | (SEQ ID NO: 519) |
| LQFWAVTAENEPS, | (SEQ ID NO: 520) |
| QFWAVTAENEPSA, | (SEQ ID NO: 521) |
| FWAVTAENEPSAG, | (SEQ ID NO: 522) |
| WAVTAENEPSAGL, | (SEQ ID NO: 523) |
| VTAENEPSAGLLS, | (SEQ ID NO: 524) |
| PSAGLLSGYPFQC, | (SEQ ID NO: 525) |
| AGLLSGYPFQCLG, | (SEQ ID NO: 526) |
| GLLSGYPFQCLGF, | (SEQ ID NO: 527) |
| SGYPFQCLGFTPE, | (SEQ ID NO: 528) |
| YPFQCLGFTPEHQ, | (SEQ ID NO: 529) |
| QCLGFTPEHQRDF, | (SEQ ID NO: 530) |
| LGFTPEHQRDFIA, | (SEQ ID NO: 531) |
| FTPEHQRDFIARD, | (SEQ ID NO: 532) |
| RDFIARDLGPTLA, | (SEQ ID NO: 533) |
| DFIARDLGPTLAN, | (SEQ ID NO: 534) |
| RDLGPTLANSTHH, | (SEQ ID NO: 535) |
| LGPTLANSTHHNV, | (SEQ ID NO: 536) |
| PTLANSTHHNVRL, | (SEQ ID NO: 537) |
| HNVRLLMLDDQRL, | (SEQ ID NO: 538) |
| VRLLMLDDQRLLL, | (SEQ ID NO: 539) |
| RLLMLDDQRLLLP, | (SEQ ID NO: 540) |

TABLE 16-continued

| Potential T-cell epitopes of human b-GCR. | |
|---|---|
| LLMLDDQRLLLPH, | (SEQ ID NO: 541) |
| LMLDDQRLLLPHW, | (SEQ ID NO: 542) |
| DDQRLLLPHWAKV, | (SEQ ID NO: 543) |
| DQRLLLPHWAKVV, | (SEQ ID NO: 544) |
| QRLLLPHWAKVVL, | (SEQ ID NO: 545) |
| RLLLPHWAKVVLT, | (SEQ ID NO: 546) |
| LLLPHWAKVVLTD, | (SEQ ID NO: 547) |
| PHWAKVVLTDPEA, | (SEQ ID NO: 548) |
| WAKVVLTDPEAAK, | (SEQ ID NO: 549) |
| AKVVLTDPEAAKY, | (SEQ ID NO: 550) |
| KVVLTDPEAAKYV, | (SEQ ID NO: 551) |
| VVLTDPEAAKYVH, | (SEQ ID NO: 552) |
| EAAKYVHGIAVHW, | (SEQ ID NO: 553) |
| AKYVEGIAVHWYL, | (SEQ ID NO: 554) |
| KYVHGIAVHWYLD, | (SEQ ID NO: 555) |
| YVHGIAVHWYLDF, | (SEQ ID NO: 556) |
| HGIAVHWYLDFLA, | (SEQ ID NO: 557) |
| IAVHWYLDFLAPA, | (SEQ ID NO: 558) |
| VHWYLDFLAPAKA, | (SEQ ID NO: 559) |
| HWYLDFLAPAKAT, | (SEQ ID NO: 560) |
| WYLDFLAPAKATL, | (SEQ ID NO: 561) |
| LDFLAPAKATLGE, | (SEQ ID NO: 562) |
| DFLAPAKATLGET, | (SEQ ID NO: 563) |
| AKATLGETHRLFP, | (SEQ ID NO: 564) |
| ATLGETHRLPPNT, | (SEQ ID NO: 565) |
| GETHRLFPNTMLF, | (SEQ ID NO: 566) |
| ETHRLFPNTMLFA, | (SEQ ID NO: 567) |
| THRLFPNTMLFAS, | (SEQ ID NO: 568) |
| HRLFPNTMLFASE, | (SEQ ID NO: 569) |
| RLFPNTMLFASEA, | (SEQ ID NO: 570) |
| FPNTMLFASEACV, | (SEQ ID NO: 571) |
| NTMLFASEACVGS, | (SEQ ID NO: 572) |
| TMLFASEACVGSK, | (SEQ ID NO: 573) |
| MLFASEACVGSKF, | (SEQ ID NO: 574) |
| ACVGSKFWEQSVR, | (SEQ ID NO: 575) |
| GSKFWEQSVRLGS, | (SEQ ID NO: 576) |
| SKFWEQSVRLGSW, | (SEQ ID NO: 577) |
| KFWEQSVRLGSWD, | (SEQ ID NO: 578) |

TABLE 16-continued

| Potential T-cell epitopes of human b-GCR. | |
|---|---|
| QSVRLGSWDRGMQ, | (SEQ ID NO: 579) |
| VRLGSWDRGMQYS, | (SEQ ID NO: 580) |
| RLGSWDRGMQYSH, | (SEQ ID NO: 581) |
| GSWDRGMQYSHSI, | (SEQ ID NO: 582) |
| WDRGMQYSHSIIT, | (SEQ ID NO: 583) |
| RGMQYSHSIITNL, | (SEQ ID NO: 584) |
| MQYSHSIITNLLY, | (SEQ ID NO: 585) |
| QYSHSIITNLLYH, | (SEQ ID NO: 586) |
| YSHSIITNLLYHV, | (SEQ ID NO: 587) |
| HSIITNLLYHVVG, | (SEQ ID NO: 588) |
| SIITNLLYHVVGW, | (SEQ ID NO: 589) |
| TNLLYHVVGWTDW, | (SEQ ID NO: 590) |
| NLLYHVVGWTDWN, | (SEQ ID NO: 591) |
| LLYHVVGWTDWNL, | (SEQ ID NO: 592) |
| YHVVGWTDWNLAL, | (SEQ ID NO: 593) |
| HVVGWTDWNLALN, | (SEQ ID NO: 594) |
| VVGWTDWNLALNP, | (SEQ ID NO: 595) |
| VGWTDWNLALNPE, | (SEQ ID NO: 596) |
| TDWNLALNPEGGP, | (SEQ ID NO: 597) |
| WNLALNPEGGPNW, | (SEQ ID NO: 598) |
| LALNPEGGPNWVR, | (SEQ ID NO: 599) |
| PNWVRNFVDSPII, | (SEQ ID NO: 600) |
| NWVRNFVDSPIIV, | (SEQ ID NO: 601) |
| RNFVDSPIIVDIT, | (SEQ ID NO: 602) |
| NFVDSPIIVDITK, | (SEQ ID NO: 603) |
| SPIIVDITKDTFY, | (SEQ ID NO: 604) |
| PIIVDITKDTFYK, | (SEQ ID NO: 605) |
| IIVDITKDTFYKQ, | (SEQ ID NO: 606) |
| VDITKDTFYKQPM, | (SEQ ID NO: 607) |
| DTFYKQPMFYHLG, | (SEQ ID NO: 608) |
| TFYKQPMFYHLGH, | (SEQ ID NO: 609) |
| QPMFYHLGHFSKF, | (SEQ ID NO: 610) |
| PMFYHLGHFSKFI, | (SEQ ID NO: 611) |
| MFYHLGHFSKFIP, | (SEQ ID NO: 612) |
| YHLGHFSKFIPEG, | (SEQ ID NO: 613) |
| GHFSKFIPEGSQR, | (SEQ ID NO: 614) |
| SKFIPEGSQRVGL, | (SEQ ID NO: 615) |
| KFIPEGSQRVGLV, | (SEQ ID NO: 616) |
| IPEGSQRVGLVAS, | (SEQ ID NO: 617) |

TABLE 16-continued

| Potential T-cell epitopes of human b-GCR. | |
|---|---|
| QRVGLVASQKNDL, | (SEQ ID NO: 618) |
| VGLVASQKNDLDA, | (SEQ ID NO: 619) |
| GLVASQKNDLDAV, | (SEQ ID NO: 620) |
| SQKNDLDAVALMH, | (SEQ ID NO: 621) |
| NDLDAVALMHPDG, | (SEQ ID NO: 622) |
| DAVALMHPDGSAV, | (SEQ ID NO: 623) |
| VALMHPDGSAVVV, | (SEQ ID NO: 624) |
| ALMHPDGSAVVVV, | (SEQ ID NO: 625) |
| SAVVVVLNRSSKD, | (SEQ ID NO: 626) |
| AVVVVLNRSSKDV, | (SEQ ID NO: 627) |
| VVVVLNRSSKDVP, | (SEQ ID NO: 628) |
| VVVLNRSSKDVPL, | (SEQ ID NO: 629) |
| VVLNRSSKDVPLT, | (SEQ ID NO: 630) |
| KDVPLTIKDPAVG, | (SEQ ID NO: 631) |
| VPLTIKDPAVGFL, | (SEQ ID NO: 632) |
| PLTIKDPAVGFLE, | (SEQ ID NO: 633) |
| LTIKDPAVGFLET, | (SEQ ID NO: 634) |
| PAVGFLETISPGY, | (SEQ ID NO: 635) |
| VGFLETISPGYSI, | (SEQ ID NO: 636) |
| GFLETISPGYSIH, | (SEQ ID NO: 637) |
| FLETISPGYSIHT, | (SEQ ID NO: 639) |
| ETISPGYSIHTYL, | (SEQ ID NO: 639) |
| PGYSIHTYLWHRQ, | (SEQ ID NO: 640) |
| PGYSIHTYLWRRQ | (SEQ ID NO: 641) |

EXAMPLE 11

De-Immunized Forms of Fc-IL2

Non-deimmunized Fc-IL2 was described e.g. in WO 96/08570. Specific de-immunized Fc-IL2 forms: Fcγ1-IL2, Fcγ2-IL2 , both forms, preferably with linker peptide and optionally modified Fc domain having reduced affinity to Fc-receptors.

EXAMPLE 12

De-Immunized Forms Fc-IL12

Non-deimmunized Fc-IL12 was described e.g. in WO 99/29732. Specific de-immunized Fc-IL12 forms: Fcγ1-

IL12, Fcγ2-IL12, both forms, preferably with linker peptide and optionally modified Fc domain having reduced affinity to Fc-receptors.

EXAMPLE 13

De-Immunized Forms of Fc-TNFa

Non-deimmunized Fc-TNFa was described e.g. in WO 99/43713. Specific de-immunized Fc-TNFa forms: Fcγ1-TNFa, Fcγ2-TNFa, both forms, preferably with linker peptide and optionally modified Fc domain having reduced affinity to Fc-receptors.

EXAMPLE 14

De-Immunized Forms of Fc-GM-CSF

Non-deimmunized Fc-GM-CSF was described e.g. in WO 99/43713 and WO 01/07081. Specific de-immunized Fc-GM-CSF forms: Fcγ1-GM-CSF, Fcγ2-GM-CSF, both forms, preferably with linker peptide and optionally modified Fc domain having reduced affinity to Fc-receptors.

EXAMPLE 15

De-Immunized Forms of Fc-subtilisin

Specific de-immunized Fc-subtilisin forms: Fcγ1-subtilisin, Fcγ2-subtilisin, both forms, preferably with linker peptide and optionally modified Fc domain having reduced affinity to Fc-receptors.

EXAMPLE 16

De-Immunized Forms of Fc-Insulin

Specific de-immunized Fc-insulin forms: Fcγ1-insulin, Fcγ2-insulin, both forms, preferably with linker peptide and optionally modified Fc domain having reduced affinity to Fc-receptors.

EXAMPLE 17

De-Immunized Forms of Fc-PSMA

Non-deimmunized Fc-PSMA was described e.g. in WO 96/08570 and WO 01/0708. Specific de-immunized Fc-PSMA forms: Fcγ1-PSMA, Fcγ2-PSMA, both forms, preferably with linker peptide and optionally modified Fc domain having reduced affinity to Fc-receptors.

EXAMPLE 18

De-Immunized Fusion Proteins Comprising Anti-EGFR Antibodies Fused to a Cytokine Humanized and murine monoclonal antibody 425 (hMAb 425, U.S. Pat. No. 5,558,864 and EP 0531 472), murine and chimeric monoclonal antibody 225 (cMAb 225, U.S. Pat. No. 4,943,533 and EP 0359 282) and murine and humanized MAb 4D5 (hMab 4D5=Herceptin®) have been de-immunized according to the invention and fused to a de-immunized IL2 or a non-modified IL-2.

Fusions of antibodies to cytokines represent a situation where the need to reduce immunogenicity is particularly great. Normally, therapeutic antibodies can induce anti-idiotype antibodies that neutralize the effectiveness of a therapeutic antibody. This is particularly true when a therapeutic antibody is administered at low or medium levels, as opposed to very high levels where tolerance can be induced. For example, the therapeutic antibodies Herceptin and Rituxan are generally given in high doses of a few hundred milligrams. In contrast, antibody-cytokine fusions are generally given in a lower dose on the order of a few milligrams. Thus, the dose of an antibody-cytokine fusion is in the range that tends to promote formation of anti-idiotype antibodies. The presence of the linked cytokine tends to exaggerate the immunogenicity of the already immunogenic antibodies. Antibody 425 is a non-human antibody which is directed to antigen EGF-R and reacts with colon cancer cells. This antibody has been fused to IL-2, as described in Example 13. The presence of IL-2 or another cytokine enhances the immunogenicity of the antibody, in particular the V regions.

In the following paragraphs the invention is described in more detail for the monoclonal anti-EGFR antibody 425-IL2 construct which was shown to have a high therapeutic value. However, the invention is not limited to this antibody and said construct and its several existing forms, but can be extended to other anti-EGFR antibodies and their fusion constructs, preferably cytokine fusion immunoglobulins, above all chimeric antibody 225 (c225-Il-2), which has very similar properties. In prinicipal, non-human, chimeric or humanized versions of the anti-EGFR antibodies can be used to synthesize said IL-2 fusion molecules Unless stated otherwise all amino acids in the variable heavy and light chains are numbered as in Kabat et al., 1991 (Sequences of Proteins of Immunological Interest, US Department of Health and Human Services). Potential T-cell epitopes are numbered with the linear number of the first amino acid of an epitope, counting from the first amino acid of the heavy and light chains.

1. Comparison with Mouse Subgroup Frameworks

The amino acid sequences of murine 425 VH (heavy chain) and VK (light chain) were compared to consensus sequences for the Kabat murine heavy and light chain subgroups. 425 VH can be assigned to mouse heavy chains subgroup IIB. The comparison with the consensus sequence for this subgroup shows that the serine at position 94 in 425 VH is unusual. The most common residue at this position is arginine. 425 VK can be assigned to mouse kappa chains subgroup Vl. The comparison with the consensus sequence for this subgroup shows that the residues at positions 45-47, 60 and 100 in 425 VK are unusual for this subgroup. Amino acid residue numbering is as per Kabat.

2. Comparison with Human Frameworks

The amino acid sequences of murine 425 VH (variable heavy chain) and VK (variable kappa light chain) were compared to the sequences of the directory of human germline VH (Tomlinson, I. M et al., J. Mol. Biol. 227:776-798 (1992)) and VK (Cox, J. P. L. et al., Eur. J. Immunol. 24:827-836 (1994)) sequences and also to human germline J region sequences (Routledge, E. G. et al., in, *Protein Engineering of Antibody Molecules for Prophylactic and Therapeutic Applications in Man*, Clark, M. ed. Academic Titles, Nottingham, UK, pp 13-44, 1991). The murine 425 sequence of the heavy and light chain can be taken, for example, from EP 0531 472.

The reference human framework selected for 425 VH was VH1GRR with human JH6. The sequence of VH1GRR in the directory ends at residue 88. Therefore there is no corresponding residue for the unusual serine at position 94 of the murine sequence. This germline sequence has been found in a rearranged mature antibody gene with 4 amino acid changes. The reference human framework selected for 425 VK was L6/vg with human JK2. This germline sequence has been found in a rearranged mature antibody heavy chain with no amino acid changes.

3. Design of "Veneered" Sequences

Following identification of the reference human framework sequences, certain non-identical amino acid residues within the 425 VH and VK frameworks were changed to the corresponding amino acid in the human reference framework sequence. Residues which are considered to be critical for antibody structure and binding were excluded from this process and not altered. The murine residues that were retained at this stage are largely non-surface, buried residues, apart from residues at the N-terminus for instance, which are close to the CDRs in the final antibody (1-8, preferably 1-5 amino acid residues). This process produces a sequence that is broadly similar to a "veneered" antibody as the surface residues are mainly human and the buried residues are as in the original murine sequence.

4. Peptide Threading Analysis

The murine and veneered 425 VH and VK sequences were analyzed using the method according of the invention. The amino acid sequences are divided into all possible 13 mers. The 13 mer peptides are sequentially presented to the models of the binding groove of the HLA-DR allotypes and a binding score assigned to each peptide for each allele. A conformational score is calculated for each pocket-bound side chain of the peptide. This score is based on steric overlap, potential hydrogen bonds between peptide and residues in the binding groove, electrostatic interactions and favorable contacts between peptide and pocket residues. The conformation of each side chain is then altered and the score recalculated. Having determined the highest conformational score, the binding score is then calculated based on the groove-bound hydrophobic residues, the non-groove hydrophilic residues and the number of residues that fit into the binding groove. Peptides which are known binders to human MHC Class II achieve a high binding score with almost no false negatives. Thus peptides that achieve a significant binding score in the current analysis are considered to be potential T-cell epitopes.

The results of the peptide threading analysis are shown in Table 17 for 425 VH and 425 VK. Potential T Cell epitopes are referred to by the linear number of the first residue of the 13 mer.

TABLE 17

Potential T-cell epitopes in murine and veneered 425 sequences.

| Sequence | Number of potential T-cell epitopes | Number of first residue of 13mer with number of bonding alleles in brackets |
|---|---|---|
| Murine 425 VH | 8 | 31(7), 35(17), 43(7), 46(8), 58(10), 62(12), 81(11), 84(16) |
| Veneered 425 VH | 7 | 31(7), 43(7), 46(8), 58(10), 62(11), 81(11), 84(16) |
| Murine 425 VK | 9 | 1(8), 2(5), 17(5), 27(5), 43(16), 72(18), 75(10), 92(10), 93(17) |
| Veneered 425 VK | 4 | 27(5), 43(16), 92(8), 93(17) |

5. Removal of Potential T Cell Epitopes

The numbering of amino acid residues for substitution is as per Kabat. Potential T Cell epitopes are referred to by the linear number of the first residue of the 13 mer. The amino acid substitutions required to remove the potential T-cell epitopes from the veneered 425 heavy chain variable region were as follows:

Substitution of proline for alanine at residue 41 (Kabat number 41) removes the potential epitope at residue number 31.

Substitution of proline for leucine at residue 45 (Kabat number 45) removes the potential epitope at residue number 43. A proline at position 45 is found in a human germline VH sequence, DP52.

Substitution of alanine for isoleucine at residue 48 (Kabat number 48) removes the potential epitope at residue number 46.

Substitution of valine for alanine at residue 68 (Kabat number 67) removes the potential epitope at residue number 58.

Substitution of isoleucine for leucine at residue 70 (Kabat number 69) removes the potential epitope at residue number 62.

Substitution of threonine for serine at residue 91 (Kabat number 87) removes the potential epitopes at residue numbers 81 and 84.

The amino acid substitutions required to remove the potential T-cell epitopes from the veneered 425 light chain variable region were as follows:

Substitution of histidine for tyrosine at residue 35 (Kabat number 36) removes the potential epitope at residue number 27.

Substitution of alanine for threonine at residue 50 (Kabat number 51) removes the potential epitope at residue number 43. This residue is within CDR2. Alanine is commonly found at this position in both human and murine antibodies. An alternative substitution to eliminate this epitope is alanine for leucine at position 45 (Kabat number 46). There is no conservative substitution that will eliminate the potential epitope. Alanine is found at this position in some antibodies.

Substitution of proline for isoleucine at residue 94 (Kabat number 95) removes the potential epitope at residue number 92. Kabat residue 95 is within CDRL3. Proline is common at this position in mouse antibody sequences and there is no change without the CDR that eliminates the potential epitope.

Substitution of valine for leucine at residue 103 (Kabat number 104) removes the potential epitope at residue number 93.

6. Design of De-Immunized Sequences

De-immunized heavy and light chain variable region sequences were designed with reference to the changes required to remove potential T-cell epitopes and consideration of framework residues that might be critical for antibody structure and binding. In addition to the De-immunized sequences based on the veneered sequence. an additional sequence was designed for each of VH and VK based on the murine sequence, termed the Mouse Peptide Threaded (Mo PT) version. For this version, changes were made directly to the murine sequence in order to eliminate T-cell epitopes, but only changes out with the CDRs that are not considered to be detrimental to binding are made. No attempt to remove surface (B-cell) epitopes has been made in this version of the de-immunized sequence.

The primary de-immunized VH includes substitutions 1 to 6 in Section 5 above and includes no potential T-cell epitopes. A further 4 de-immunized VH sequences were designed in order to test the effect of the various substitutions required on antibody binding.

The cumulative alterations made to the primary de-immunized sequence (425 VH1GRR-VH-v1) and the potential T-cell epitopes remaining are detailed in Table 18. The mouse threaded version is included for comparison.

TABLE 18

Amino acid changes and potential epitopes in de-immunized 425 VH.

| Variant | Cumulative Residue Changes | Potential T Cell Epitopes |
|---|---|---|
| 425 VH1GRR-VH-v1 | None | None |
| 425 VH1GRR-VH-v2 | 48A → I | 46(8) |
| 425 VH1GRR-VH-v3 | 45P → L | 43(7), 46(8) |
| 425 VH1GRR-VH-v4 | 67V → A, 69I → L | 43(7), 46(8), 58(10), 62(11) |
| 425 VH1GRR-VH-v5 | 41P → A | 31(7), 43(7), 46(8), 58(10), 62(11) |
| 425 VH-MoPT | NA | 43(7), 46(8) |

The primary de-immunized VK includes substitutions 1 to 4 in Section 5 above and includes no potential T-cell epitopes. A further 4 de-immunized VK sequences were designed in order to test the effect of the various substitutions required on antibody binding. Version 2 is an alternative to Version 1 in which an alternative substitution has been used to remove the same potential T-cell epitope.

The cumulative alterations made to the primary de-immunized sequence (425 L6-vg-VK-v1) and the potential T-cell epitopes remaining are detailed in Table 19. The mouse threaded version is included for comparison.

TABLE 19

Amino acid changes and potential epitopes in de-immunized 425 VK.

| Variant | Cumulative Residue Changes | Potential T-cell Epitopes |
|---|---|---|
| 425 L6-vg-VK-v1 | None | None |
| 425 L6-vg-VK-v1 | 51 A → T, 46L → A | None |
| 425 L6-vg-VK-v1 | 46 A → L | 43(16) |
| 425 L6-vg-VK-v1 | 95 P → I | 43(16), 92(8) |
| 425 L6-vg-VK-v1 | 36 H → Y | 27(5), 43(16), 92(8) |
| 425VK-MoPT | NA | 27(5), 43(16), 92(8) |

TABLE 20

Original and "veneered" sequences of VH and VK of murine MAb 425.

425 VH mouse (SEQ ID NO: 642):
QVQLQQPGAELVKPGASVKLSCKASGYTFTSHWMHWVKQRAGQGLEWIGE
FNPSNGRTNYNEKFKSKATLTVDKSSSTAYMQLSSLTSEDSAVYYCASRD
YDYDGRYFDYWGQGTTLTVSS 425 VK mouse (SEQ ID NO: 643):
QIVLTQSPAIMSASPGEKVTMTCSASSSVTYMYWYQQKPGSSPRLLIYDT
SNLASGVPVRFSGSGSGTSYSLTISRMEAEDAATYYCQQWSSHIFTFGSG
TKLEIK 425 VH veneered (SEQ ID NO: 644):
QVQLVQSGAELVKPGASVKLSCKASGYTFTSHWMHWVKQAAGQGLEWIGE
FNPSNGRTNYNEKFKSRATLTVDKSTSTAYMQLSSLTSEDSAVYYCASRD
YDYDGRYFDYWGQGTTLTVSS 425 VK veneered (SEQ ID NO: 645):
QIVLTQSPATLSASPGERATMSCSASSSVTYMYWYQQKPGQSPRLLIYDT
SNLASGVPARFSGSGSGTSYTLTISSLEAEDAATYYCQQWSSHIFTFGQG
TKLEIK

TABLE 21

De-immunized sequences of variable heavy and light chain of MAb 425.

426 de-immunized VH1 (SEQ ID NO: 646):
QVQLVQSGAELVKPGASVKLSCKASGYTFTSHWMHWVKQAPGQGPEWAGE
FNPSNGRTNYNEKFKSRVTITVDKSTSTAYMQLSSLTSEDTAVYYCASRD
YDYDGRYFDYWGQGTTLTVSS 425 de-immunized VK1 (SEQ ID NO: 647):
QIVLTQSPATLSASPGERATMSCSASSSVTYMYWHQQKPGQSPRLLIYDA
SNLASGVPARFSGSGSGTSYTLTISSLEAEDAATYYCQQWSSHPFTFGQG
TKVEIK 425 de-immunized VH2 (SEQ ID NO: 648):
QVQLVQSGAELVKPGASVKLSCKASGYTFTSHWMHWVKQAPGQGPEWIGE
FNPSNGRTNYNEKFKSRVTITVDKSTSTAYMQLSSLTSEDTAVYYCASRD
YDYDGRYFDYWGQGTTLTVSS 425 de-immunized VK2 (SEQ ID NO: 649):
QIVLTQSPATLSASPGERATMSCSASSSVTYMYWHQQKPGQSPRALIYDT
SNLASGVPARFSGSGSGTSYTLTISSLEAEDAATYYCQQWSSHPFTFGQG
TKVEIK 425 de-immunized VH3 (SEQ ID NO: 650):
QVQLVQSGAELVKPGASVKLSCKASGYTFTSHWMHWVKQAPGQGLEWIGE
FNPSNGRTNYNEKFKSRVTITVDKSTSTAYMQLSSLTSEDTAVYYCASRD
YDYDGRYFDYWGQGTTLTVSS 425 de-immunized VK3 (SEQ ID NO: 651):
QIVLTQSPATLSASPGERATMSCSASSSVTYMYWHQQKPGQSPRLLIYDT
SNLASGVPARFSGSGSGTSYTLTISSLEAEDAATYYCQQWSSHPFTFGQG
TKVEIK 425 de-immunized VH4 (SEQ ID NO: 652):
QVQLVQSGAELVKPGASVKLSCKASGYTFTSHWMHWVKQAPGQGLEWIGE
FNPSNGRTNYNEKFKSRATLTVDKSTSTAYMQLSSLTSEDTAVYYCASRD
YDYDGRYFDYWGQGTTLTVSS 425 de-immunized VK4 (SEQ ID NO: 653):
QIVLTQSPATLSASPGERATMSCSASSSVTYMYWHQQKPGQSPRLLIYDT
SNLASGVPARFSGSGSGTSYTLTISSLEAEDAATYYCQQWSSHIFTFGQG
TKVEIK 425 de-immunized VH5 (SEQ ID NO: 654):
QVQLVQSGAELVKPGASVKLSCKASGYTFTSHWMHWVKQAAGQGLEWIGE
FNPSNGRTNYNEKFKSRATLTVDKSTSTAYMQLSSLTSEDTAVYYCASRD
YDYDGRYFDYWGQGTTLTVSS 425 de-immunized VK5 (SEQ ID NO: 655):
QIVLTQSPATLSASPGERATMSCSASSSVTYMYWYQQKPGQSPRLLIYDT
SNLASGVPARFSGSGSGTSYTLTISSLEAEDAATYYCQQWSSHIFTFGQG
TKVEIK 425 VH mouse, peptide threaded (Mo PT)
(SEQ ID NO: 656):
QVQLQQPGAELVKPGASVKLSCKASGYTFTSHWMHWVKQAPGQGLEWIGE
FNPSNGRTNYNEKFKSRVTITVDKSSSTAYMQLSSLTSEDTAVYYCASRD
YDYDGRYFDYWGQGTTLTVSS 425 VK mouse, peptide threaded (Mo PT)
(SEQ ID NO: 657):
QIVLTQSPATLSASPGEKATMTCSASSSVTYMYWYQQKPGSSPRLLIYDT
SNLASGVPVRFSGSGSGTSYSLTISRLEAEDAATYYCQQWSSHIFTFGQG
TKVEIK As already mentioned, the modified anti-EGFR antibody—cytokine constructs according to the invention, preferably MAb 425-Il2, can be used in pharmaceutical compositions and pharmaceutical kits preferably for the treatment of cancer. "Cancer" and "tumor" refer to or describe the physiological condition in mammals that is typically characterized by unregulated cell growth. By means of the pharmaceutical compositions according of the present invention tumors can be treated such as tumors of the breast, heart, lung, small intestine, colon, spleen, kidney, bladder, head and neck, ovary, prostate, brain, pancreas, skin, bone, bone marrow, blood, thymus, uterus, testicles, cervix, and liver. In analogy to antibody 425 similar fusion constructs can be obtained using monoclaonal antibody 225 in murine, chimeric or humanized forms.

EXAMPLE 19

De-Immunized Forms of 14.18 Antibody—IL2 and KS-1/4-IL2

The cytokine interleukin 2 (IL-2) has been fused to specific monoclonal antibodies KS-1/4 and ch14.18 directed to the tumor associated antigens epithelial cell adhesion molecule (Ep-CAM, KSA, KS 1/4 antigen) and the disialoganglioside GD, respectively, to form the fusion proteins ch14.18-IL-2 and KS1/4-IL-2, respectively, (U.S. Pat. No. 5,650,150; EP 0 338 767).

Theses antibodies have been de-immunized according to the invention and fused to a immunogenicly modified IL2 or a non-modified IL-2.

Anti-EpCAM Antibody KS 1/4

The monoclonal antibody KS1/4 is a murine antibody that specifically binds to the 40,000 dalton cell surface antigen EpCAM (epithelial cell adhesion molecule) found in high density on adenocarcinoma cells and also found at much lower levels on certain normal epithelial cells. This antibody has been shown to be effective for the detection of disease. A variety of fusions of KS-1/4 to single and combined cytokines such as IL-2 and IL-12, have been described (WO 98/25978, WO 01/58957A, and WO 01/10912). These fusion proteins are effective in animal models of cancer. However, due to the presence of cytokines, these fusion proteins are particularly immunogenic. There is a need for altered KS antibody molecules with a reduced propensity to elicit an immune response on administration to the human host.

Modified sequences in Mab KS 1/4 providing a modified KS antibody according to the invention are shown below. A mutated form of the KS-1/4 in which the T-cell epitopes in the V regions were completely removed by mutation, as defined by the criteria given above in the section on computer algorithms, was efficiently expressed in mammalian cells and bound to the EpCAM antigen with only about an 8-fold reduction of affinity. This molecule was termed VHv1VKv1. A second antibody, VHv2VKv1, had only about a 3-fold reduction in affinity and differed from VHv1VKv1 by a single amino acid substitution. These two antibodies have been expressed in mammalian cells as KS-IL2 fusion proteins. The KS(VHv1/VKv1)-IL2 and KS(VHv2VKv1) are the most preferred embodiments of the invention with respect to treatment of a broad spectrum of human cancers by immune therapy.

1 Comparison with Mouse Subgroup Frameworks

Figure 2:
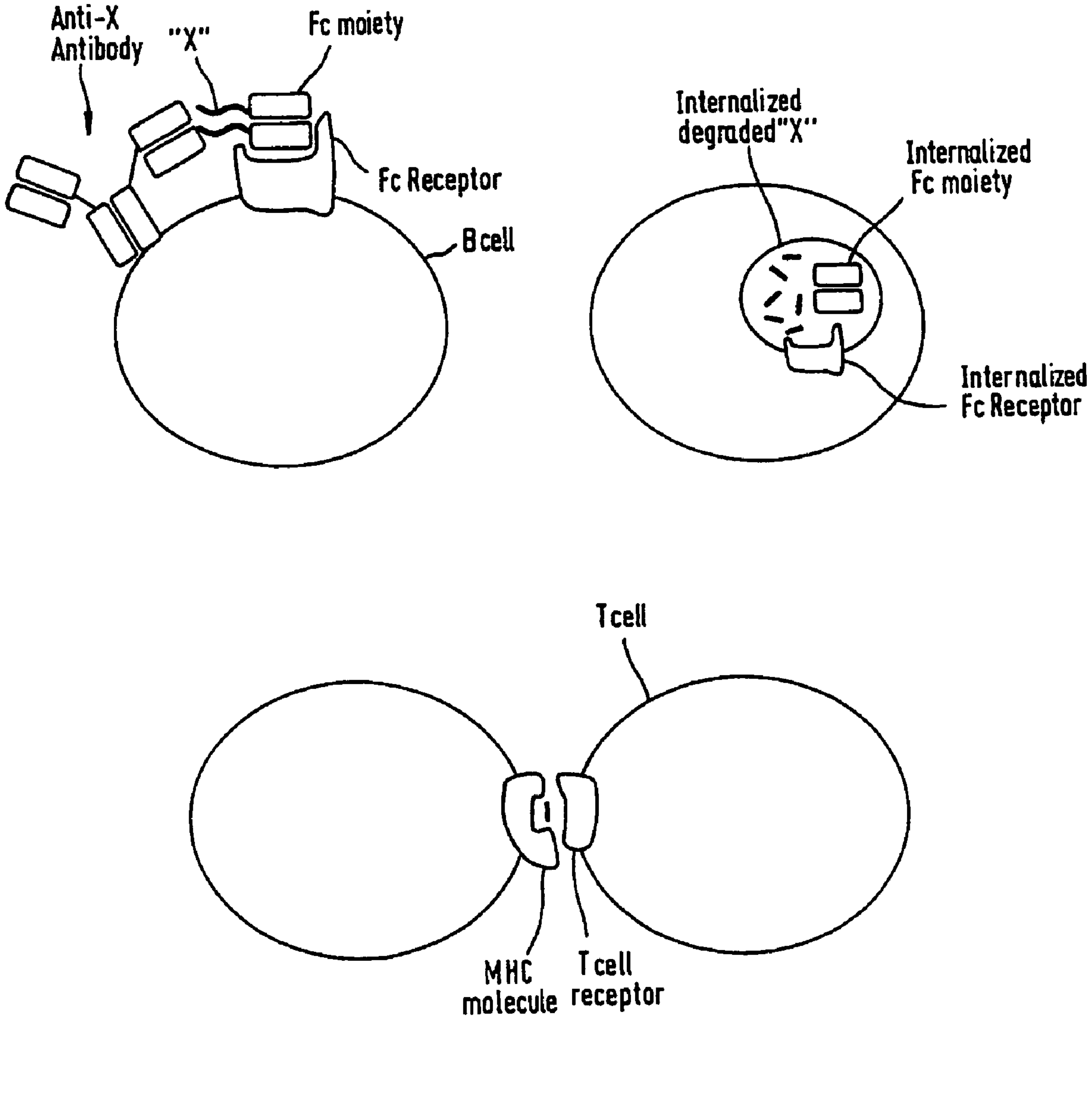
FIG. 2 shows a mechanism of enhanced immunogenicity for a fusion protein comprising an Fc moiety and a second moiety.
Figure 3:
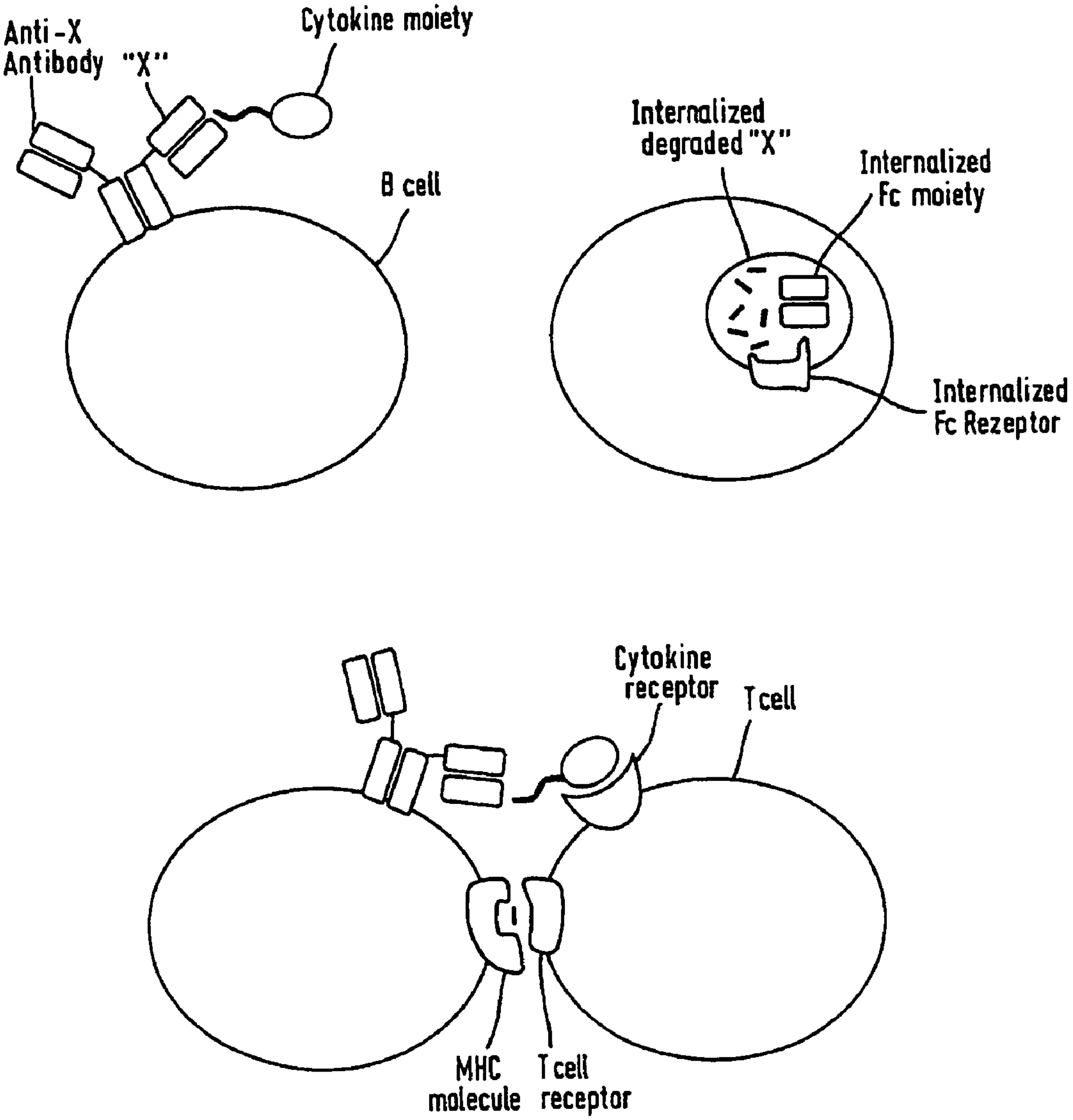
FIG. 3 illustrates a second mechanism by which fusion proteins displays enhanced immunogenicity.
Figure 4:
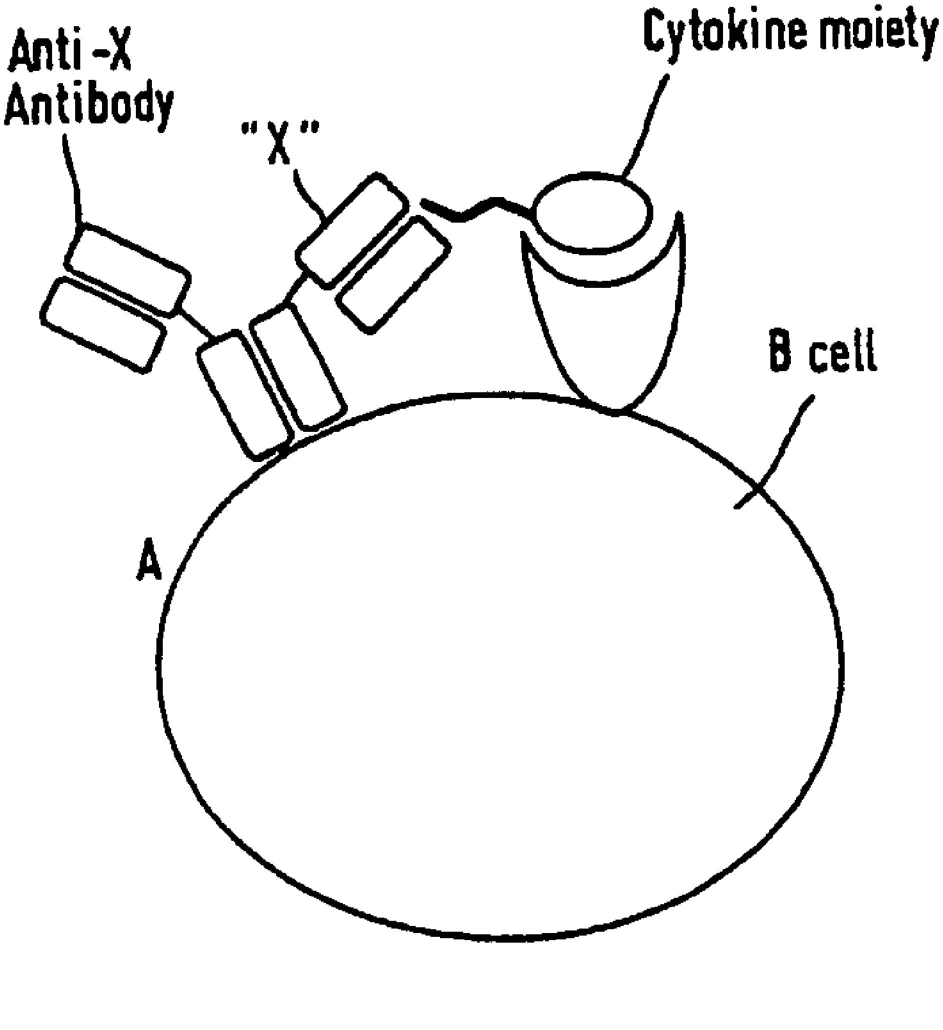
FIG. 4 illustrates another mechanism by which an engineered protein displays enhanced immunogenicity. In this case, a cytokine-X fusion protein directly activates a B cell. The B cell synthesizes a specific antibody to X, which increases the local concentration of the cytokine in the neighborhood of the B cell.
Figure 5:
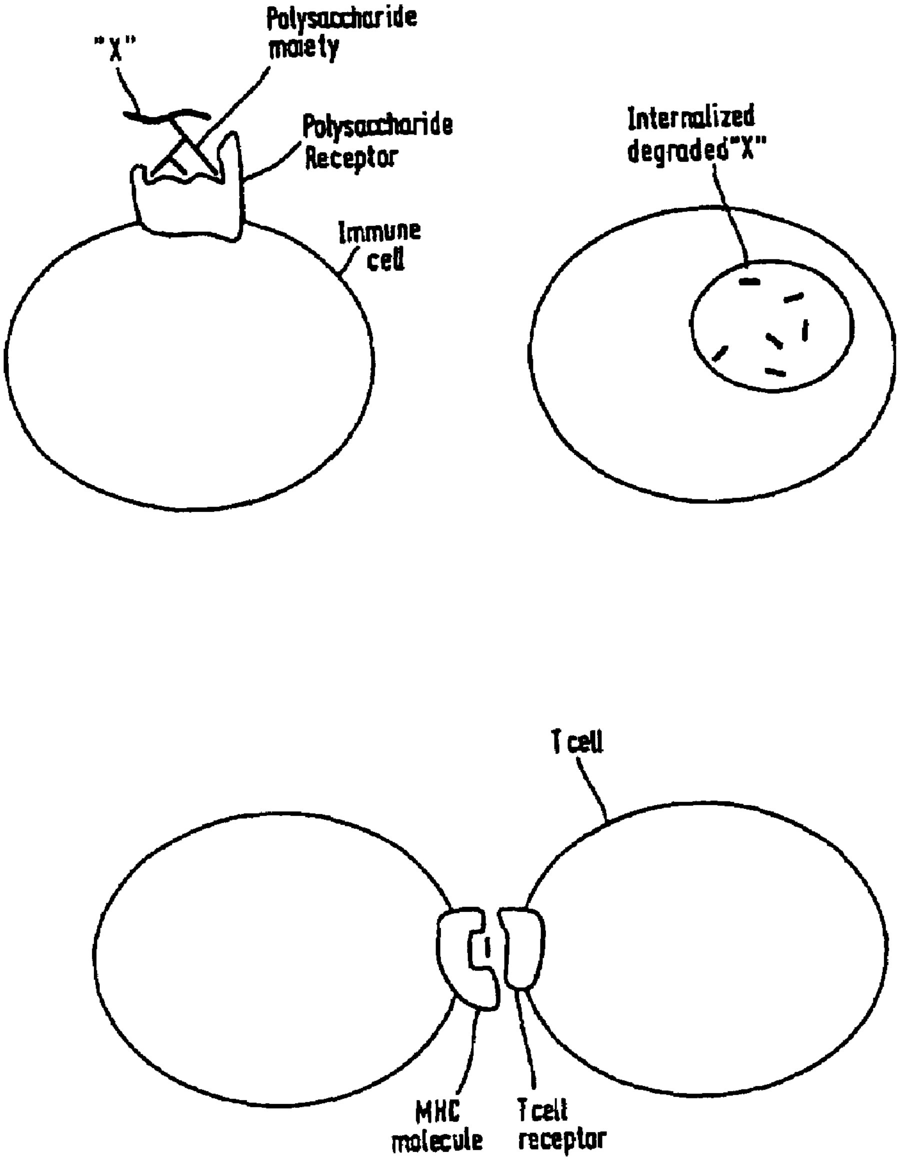
FIG. 5 illustrates another mechanism by which an engineered protein displays enhanced immunogenicity.
Figure 6:
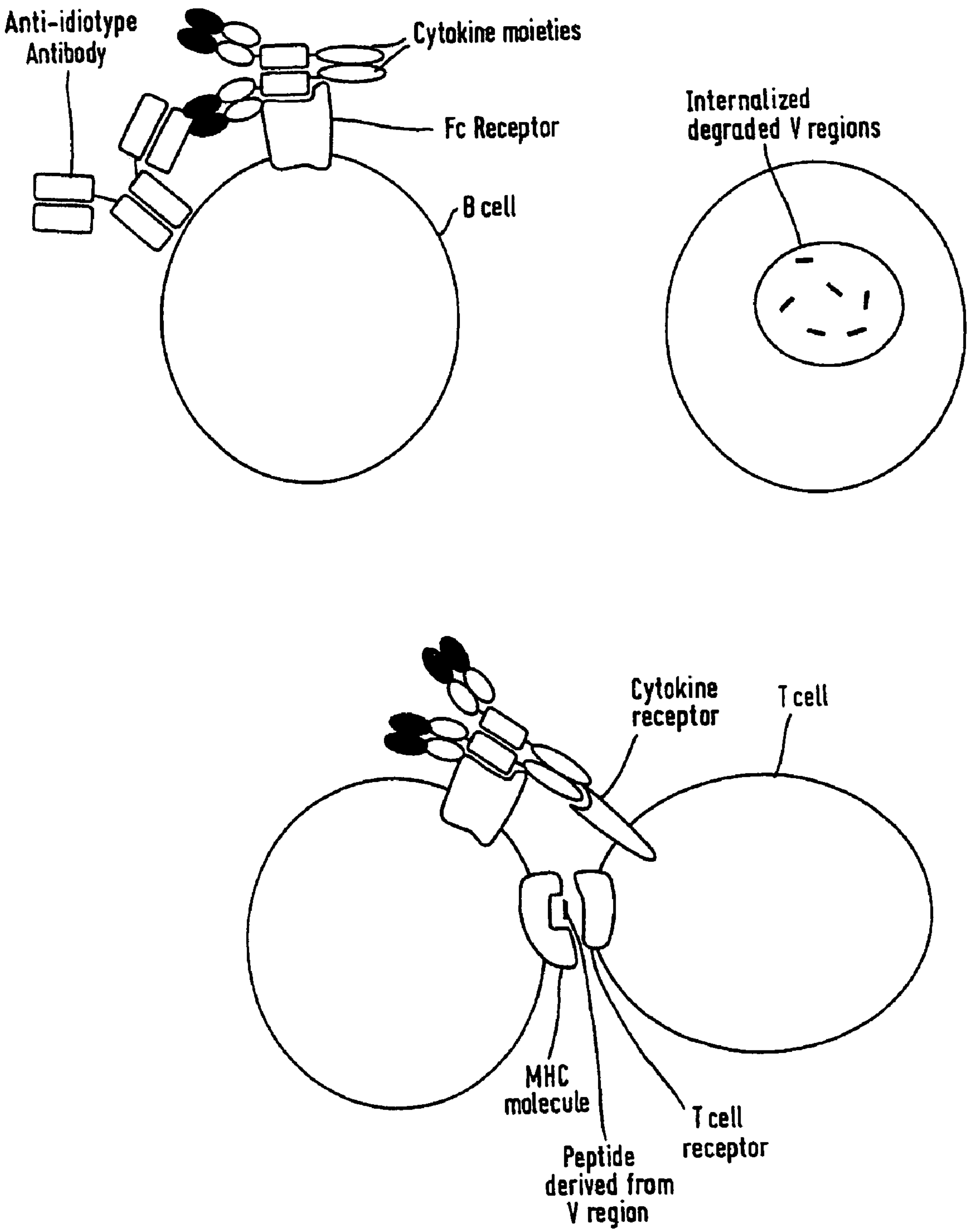
FIG. 6 shows a mechanism by which an antibody-cytokine fusion protein displays enhanced immunogenicity.

The amino acid sequences of murine KS VH and VK were compared to consensus sequences for the Kabat murine heavy and light chain subgroups (Kabat et al., 1991). Murine KS VH cannot be assigned to any one Subgroup, but is closest to Subgroup II(A) and V(A). Unusual residues are found at position 2 which is normally valine, 46 which is normally glutamic acid, and 68 which is normally threonine. Residue 69 is more commonly leucine or iso-leucine. At 82b, serine is most often found. Murine KS VK can be assigned to Subgroup VI (FIG. 2). Unusual residues are found at 46 and 47 which are commonly both leucine. Residue 58 is unusual with either leucine or valine normally found at this position.

2 Comparison with Human Frameworks

The amino acid sequences of murine KS VH and VK were compared to the sequences of the directory of human germline VH (Tomlinson et al., 1992) and VK (COX et al., 1994) sequences and also to human germline J region sequences (Routledge et al., 1993). The reference human framework selected for KS VH was DP10 with human JH6. This germline sequence has been found in a rearranged mature antibody gene with no amino acid changes. The reference human framework selected for KS VK was B1. For framework-2 the sequence of the mature human antibody IMEV was used (in Kabat et al., 1991). This sequence is identical to the murine sequence immediately adjacent to CDR2. The J region sequence was human JK4. This germline sequence has not been found as rearranged mature antibody light chain.

3 Design of Veneered Sequences

Following identification of the reference human framework sequences, certain non-identical amino acid residues within the 425 VH and VK frameworks were changed to the corresponding amino acid in the human reference sequence. Residues which are considered to be critical for antibody structure and bindin 2 were excluded from this process and not altered. The murine residues that were retained at this stage are largely non-surface, buried residues, apart from residues at the N-terminus for instance, which are close to the CDRs in the final antibody. This process produces a sequence that is broadly similar to a "veneered" antibody as the surface residues are mainly human and the buried residues are as in the original murine sequence.

4 Peptide Threading Analysis

The murine and veneered KS VH and VK sequences were analyzed using the method according to the invention. The amino acid sequences are divided into all possible 13 imers. The 13-mer peptides are sequentially presented to the models of the binding groove of the HLA-DR allotypes and a binding score assigned to each peptide for each allele. A conformational score is calculated for each pocket-bound side chain of the peptide. This score is based on steric overlap, potential hydrogen bonds between peptide and residues in the binding groove, electrostatic interactions and favorable contacts between peptide and pocket residues. The conformation of each side chain is then altered and the score recalculated.

Having determined the highest conformational score, the binding score is then calculated based on the (groove-bound hydrophobic residues, the non-groove hydrophilic residues and the number of residues that fit into the binding groove. Known binders to MHC class II achieve a significant binding score with almost no false negatives. Thus peptides achieving, a significant binding score from the current analysis are considered to be potential T-cell epitopes.

The results of the peptide threading analysis for the murine and veneered sequences are shown in Table 22.

TABLE 22

Potential T-cell epitopes in murine and veneered KS sequences.

| Sequence | Number of potential T-cell epitopes | Location of potential epitopes (no. of potential MHC binders) |
|---|---|---|
| Murine KS VH | 6 | 35(11), 62(17), 78(12), 81(12), 89(6), 98(15) |
| Murine KS VH | 5 | 30(7), 62(15), 78(11), 89(6), 98(15) |

TABLE 22-continued

| Potential T-cell epitopes in murine and veneered KS sequences. | | |
|---|---|---|
| Sequence | Number of potential T-cell epitopes | Location of potential epitopes (no. of potential MHC binders) |
| Murine KS VK | 6 | 1(14), 2(5), 17(5), 27(5), 51(13), 72(18) |
| Veneered KS VK | 3 | 1(17), 27(5), 51(13) |

5 Removal of Potential T Cell Epitopes

Potential T-cell epitopes are removed by making amino acid substitutions in the particular peptide that constitutes the epitope. Substitutions were made by inserting amino acids of similar physicochemical properties if possible. However in order to remove some potential epitopes, amino acids of different size, charge or hydrophobicity may need to be substituted. If changes have to made within CDRs which might have an effect on binding, there is then a need to make a variant with and without the particular amino acid substitution. Numbering of amino acid residues for substitution is as per Kabat. Potential T Cell epitopes are referred to by the linear number of the first residue of the 13 mer.

The amino acid changes required to remove T-cell epitopes from the veneered KS heavy chain variable region were as follows:

1. Substitution of arginine for lysine at residue 38 (Kabat number 38) removes the potential epitope at residue no 30.
2. Substitution of alanine for leucine at residue 72 (Kabat number 71) and isoleucine for phenylalanine at residue 70 (Kabat number 69) removes the potential epitope at residue 62. An isoleucine at Kabat number 69 and alanine at Kabat number 71 is found in a human germline VH sequence, DP10.
3. Substitution of leucine for alanine at residue 79 (Kabat number 78) removes the potential epitope at residue number 78.
4. Substitution of threonine for methionine at residue 91 (Kabat number 87), removes the potential epitope at residue number 89.
5. Substitution of methionine for at isoleucine residue 100 (Kabat number 96) in CDRH3 removes the potential epitope at residue 98. There is no change out with CDRH3 which removes this potential epitope.

The amino acid substitutions required to remove the potential T-cell epitopes from the veneered KS light chain variable region were as follows:

1. Substitution of isoleucine for methionine at residue 32 (Kabat number 33) removes the potential epitope at residue number 27. This residue is within CDR2. Isoleucine is commonly found at this position in human antibodies.
2. The potential epitope at position 1 is removed by substituting valine for leucine at residue (Kabat number 3).
3. Substitution of serine for alanine at residue 59 (Kabat number 60) removes the potential epitope at residue number 51.

6 Design of De-Immunized Sequences

De-immunized heavy and light chain sequences were designed with reference to the changes required to remove potential T-cell epitopes and consideration of framework residues that might be critical for antibody structure and binding. In addition to the de-immunized sequences based on the veneered sequence, an additional sequence was designed for each VH, and VK based on the murine sequence, termed the Mouse Peptide Threaded (MoPT) version. For this version, changes. were made directly to the murine sequence in order to eliminate T-cell epitopes, but only changes outside the CDRs that are not considered to be detrimental to binding are made. No attempt to remove surface (B cell) epitopes has been made in this version of the de-immunized sequence. The primary de-immunized VH includes substitutions 1 to 5 in Section 5 above and one extra change at residue 43 (Kabat number 43). Lysine found in the murine sequence was substituted for the glutamine from the human framework. Lysine is positively charged and therefore significantly different to glutamine; this region may be involved in VH/VL contacts. The primary de-immunized VH includes no potential T-cell epitopes. A further 4 de-immunized VHs were designed in order to test the effect of the various substitutions required on antibody binding.

The cumulative alterations made to the primary de-immunized sequence (KSDIVHv1) and the potential T-cell epitopes remaining are detailed in Table 23.

TABLE 23

| Amino acid changes and potential epitopes in de-immunized KS VH. | | |
|---|---|---|
| Variant | Cumulative residue changes | Potential epitopes (no. of potential MHC binders from 18 tested) |
| KSDIVHv1 | None | None |
| KSDIVHv2 | 96M → I | 98(15) |
| KSDIVHv3 | 71A → L, 78L → A | 62(16), 78(11), 98(15) |
| KSDIVHv4 | 38 R → K | 30(7), 62(16), 78(11), 98(15) |
| KSDIVHv5 | 68T → A, 69I → F | 30(7), 62(17), 78(11), 98(15) |
| KSMoPTVH | NA | 98(15), 78(12) |

The primary de-immunized VK includes substitutions 1 to 3 in Section 5 above. A further 3 de-immunized VKs were designed in order to test the effect of the various substitutions required on antibody binding.

The cumulative alterations made to the primary de-immunized sequence (KSDIVKv1) and the potential T-cell epitopes remaining are detailed in Table 24. Sequences of modified epitopes of KS VH and KS VK are shown in Table 25.

TABLE 24

| Amino acid changes and potential epitopes in de-immunized KS VK. | | |
|---|---|---|
| Variant | Cumulative residue changes | Potential epitopes (no. of potential MHC binders from 18 tested) |
| KSDIVKv1 | None | None |
| KSDIVKv2 | 33I → M | 27(5) |
| KSDIVKv3 | 3V → L | 1(17), 27(5) |
| KSDIVKv4 | 60 S → A | 1(17), 27(5), 5(13) |
| KSMoPTVK | NA | None |

TABLE 25

| Sequences of versions of modified epitopes of KS VH and KS VK. |
|---|
| KS VH veneered (SEQ ID NO: 658): QIQLVQSGPELKKPGSSVKISCKASGYTFTNYGMNWVKQAPGQGLKWMGW INTYTGEPTYADDFKGRFTFTLETSTSTAYLQLNNLRSEDMATYFCVRFI SKGDYWGQGTTVTVSS |
| KS VK veneered (SEQ ID NO: 659): QILLTQSPASLAVSPGQRATITCSASSSVSYMLWYQQKPGQPPKPWIFDT SNLASGFPARFSGSGSGTSYTLTINSLEAEDAATYYCHQRSGYPYTFGGG TKVEIK |
| KS de-immunized VH1 (SEQ ID NO: 660): QIQLVQSGPELKKPGSSVKISCKASGYTFTNYGMNWVRQAPGKGLKWMGW INTYTGEPTYADDFKGRFTITAETSTSTLYLQLNNLRSEDTATYFCVRFM SKGDYWGQGTTVTVSS |
| KS de-immunized VK1 (SEQ ID NO: 661): QIVLTQSPASLAVSPGQRATITCSASSSVSYILWYQQKPGQPPKPWIFDT SNLASGFPSRFSGSGSGTSYTLTINSLEAEDAATYYCHQRSGYPYTFGGG TKVEIK |
| KS de-immunized VH2 (SEQ ID NO: 662): QIQLVQSGPELKKPGSSVKISCKASGYTFTNYGMNWVRQAPGKGLKWMGW INTYTGEPTYADDFKGRFTITAETSTSTLYLQLNNLRSEDTATYFCVRFI SKGDYWGQGTTVTVSS |
| KS de-immunized VK2 (SEQ ID NO: 663): QIVLTQSPASLAVSPGQRATITCSASSSVSYMLWYQQKPGQPPKPWIFDT SNLASGFPSRFSGSGSGTSYTLTINSLEAEDAATYYCHQRSGYPYTFGGG TKVEIK |
| KS de-immunized VH3 (SEQ ID NO: 664): QIQLVQSGPELKKPGSSVKISCKASGYTFTNYGMNWVRQAPGKGLKWMGW INTYTGEPTYADDFKGRFTITLETSTSTAYLQLNNLRSEDTATYFCVRFI SKGDYWGQGTTVTVSS |
| KS de-immunized VK3 (SEQ ID NO: 665): QILLTQSPASLAVSPGQPATITCSASSSVSYMLWYQQKPGQPPKPWIFDT SNLASGFPSRFSGSGSGTSYTLTINSLEAEDAATYYCHQRSGYPYTFGGG TKVEIK |
| KS de-immunized VH4 (SEQ ID NO: 666): QIQLVQSGPELKKPGSSVKISCKASGYTFTNYGMNWVKQAPGKGLKWMGW INTYTGEPTYADDFKGRFTITLETSTSTAYLQLNNLRSEDTATYFCVRFI SKGDYWGQGTTVTVSS |
| KS de-iminunized VK4 (SEQ ID NO: 667): QILLTQSPASLAVSPGQRATITCSASSSVSYMLWYQQKPGQPPKPWIFDT SNLASGFPARFSGSGSGTSYTLTINSLEAEDAATYYCHQRSGYPYTFGGG TKVEIK |
| KS de-immunized VHS (SEQ ID NO: 668): QIQLVQSGPELKKPGSSVKISCKASGYTFTNYGMNWVKQAPGKGLKWMGW INTYTGEPTYADDFKGRFAFTLETSTSTAYLQLNNLRSEDTATYFCVRFI SKGDYWGQGTTVTVSS |
| KS de-immunized VK5 (SEQ ID NO: 669): QILLTQSPASLAVSPGQRATITCSASSSVSYMLWYQQKPGSSPKPWIYDT SNLASGFPARFSGSGSGTSYTLTINSLEAEDAATYYCHQRSGYPYTFGGG TKVEIK |
| KS VH mouse, peptide threaded (Mo PT) (SEQ ID NO: 670): QIQLVQSGPELKKPGETVKISCKASGYTFTNYGMNWVRQAPGKGLKWMGW INTYTGEPTYADDFKGRFVFSLETSASTAFLQLNNLRSEDTATYFCVRFI SKGDYWGQGTSVTVSS |
| KS VK mouse, peptide threaded (Mo PT) (SEQ ID NO: 671): QIVLTQSPATLSASPGERVTITCSASSSVSYMLWYLQKPGSSPKPWIFDT SNLASGFPSRFSGSGSGTTYSLIISSLEAEDAATYYCHQRSGYPYTFGGG TKLEIK |

TABLE 25-continued

| Sequences of versions of modified epitopes of KS VH and KS VK. |
|---|
| KS VH mouse (SEQ ID NO: 672): QIQLVQSGPELKKPGETVKISCKASGYTFTNYGMNWVKQTPGKGLKWMGW INTYTGEPTYADDFKGRFAFSLETSASTAFLQINNLRNEDMATYFCVRFI SKGDYWGQGTSVTVSS |
| KS VK mouse (SEQ ID NO: 673): QILLTQSPAIMSASPGEKVTMTCSASSSVSYMLWYQQKPGSSPKPWIFDT SNLASGFPARFSGSGSGTSYSLIISSMEAEDAATYYCHQRSGYPYTFGGG TKLEIK |

MAb 14.18-IL-2

In analogy, monoclonal antibody 14.18 was fused to IL-2 and deimmunized according to the invention.

Potential T-cell epitopes in murine and veneered 14.18 sequences are shown in Table 26.

TABLE 26

Potential T-cell epitopes in murine and veneered MAb 14.18.

| Sequence | Number of potential T-cell | Location of potential epitopes |
|---|---|---|
| Murine 14.18 VH | 11 | 3(17), 9(15), 30(5), 35(17), 39(15), 43(9), 58(12), 62(11), 81(11), 84(16), 101(7) |
| Veneered 14.18 VH | 5 | 43(9), 58(12), 62(11), 81(11), 84(16) |
| Murine 14.18 VK | 7 | 7(7), 13(11), 27(15), 49(11), 86(17), 97(11), 100(4) |
| Veneered 14.18 VK | 5 | 27(I5), 49(11), 86(17), 97(11), 100(17) |

Amino acid changes and potential epitopes in de-immunized 14.18 VH are shown in Table 27.

TABLE 27

Amino acid changes and potential epitopes in de-immunized 14.18 VH.

| Variant | Cumulative residue changes | Potential epitopes (no. of potential MHC binders from 18 tested) |
|---|---|---|
| 14.18DIVH1 | None | none |
| 14.18DIVH2 | 41I → P, 45L → T, 50L → A | none |
| 14.18DIVH3 | 65S → G | 58(8) |
| 14.18DIVH4 | 71A → V | 58(8), 62(4) |
| 14.18DIVH5 | 45T → L, 41P → I | 43(9) 58(8) 62(4) |
| 14.18MoPTVH | NA | 43(9) 58(12) 62(11) |

Amino acid changes and potential epitopes in de-immunized 14.18 VK are shown in Table 28.

TABLE 28

Amino acid changes and potential epitopes in de-immunized 14.18 VK.

| Variant | Cumulative residue changes* | Potential epitopes' (no. of potential MHC binders from 18 tested) |
|---|---|---|
| 14.18DIVKI | None | none |
| 14.18DIVK2 | 46L→ M, 49Y → H | none |
| 14.18DIVK3 | 96P → T, 100Q → G | 97(5) |
| 14.18DIVK4 | 96T → L | 97(11) |

TABLE 28-continued

Amino acid changes and potential epitopes in de-immunized 14.18 VK.

| Variant | Cumulative residue changes* | Potential epitopes' (no. of potential MHC binders from 18 tested) |
|---|---|---|
| 14.18DIVK5 | 27e S → R | 27(15), 97(11) |
| 14.18DIVK6 | 46M → L | 27(15), 49 (11), 97(11) |
| 14.18MoPTVK | NA | 27(15), 49 (11), 97(11), 100(4) |

Sequences of versions of modified epitopes in de-immunized and veneered 14.18 VH and VK are shown in Table 29.

TABLE 29

Sequences of versions of modified epitopes in de-immunized and veneered 14.18 VH and VK.

14.18 VH veneered (SEQ ID NO: 674):
EVQLLQSGPELKKPGASVKISCKASGSSFTGYNMNWVRQAPGQRLEWIGA
IDPYYGGTSYNQKFKGRATLSVDKSSSQAYMHLKSLTSEDSAVYYCVSGM
EYWGQGTTVTVSS 14.18 VK veneered (SEQ ID NO: 675):
DVVMTQSPGTLPVSLGERATISCRSSQSLVHRNGNTYLHWYLQKPGQSPK
LLIHKVSNRFSGVPDRFSGSGSGTDFTLTISRLEAEDLAVYFCSQSTHVP
PLTFGQGTKLEIK 14.18 de-immunized VH1 (SEQ ID NO: 676):
EVQLLQSGPELKKPGASVKISCKASGSSFTGYNMNWVRQAIGQRLEWIGL
IDPYYGGTSYNQKFKSRVTITADKSSSQAYMHLKSLTSEDTAVYYCVSGM
EYWGQGTTVTVSS 14.18 de-immunized VK1 (SEQ ID NO: 677):
DVVMTQSPGTLPVSLGERATISCRSSQSLVHSNGNTYLHWYLQKPGQSPK
LLIYKVSNRFSGVPDRFSGSGSGTDFTLTISRLEAEDMAVYFCSQSTHVP
PPTFGQGTKVEIK 14.18 de-immunized VH2 (SEQ ID NO: 678):
EVQLLQSGPELKKPGASVKISCKASGSSFTGYNMNWVRQAPGQRTEWIGA
IDPYYGGTSYNQKFKSRVTITADKSSSQAYMHLKSLTSEDTAVYYCVSGM
EYWGQGTTVTVSS 14.18 de-immunized VK2 (SEQ ID NO: 679):
DVVMTQSPGTLPVSLGERATISCRSSQSLVHSNGNTYLHWYLQKPGQSPK
MLIHKVSNRFSGVPDRFSGSGSGTDFTLTISRLEAEDMAVYFCSQSTHVP
PPTFGQGTKVEIK 14.18 de-immunized VH3 (SEQ ID NO: 680):
EVQLLQSGPELKKPGASVKISCKASGSSFTGYNMNWVRQAPGQRTEWIGA
IDPYYGGTSYNQKFKGRVTITADKSSSQAYMHLKSLTSEDTAVYYCVSGM
EYWGQGTTVTVSS TABLE 29-continued Sequences of versions of modified epitopes in de-immunized and veneered 14.18 VH and VK.

14.18 de-immunized VK3 (SEQ ID NO: 681):
DVVMTQSPGTLPVSLGERATISCRSSQSLVHSNGNTYLHWYLQKPGQSPK
MLIHKVSNRFSGVPDRFSGSGSGTDFTLTISRLEAEDMAVYFCSQSTHVP
PTTFGGGTKVEIK 14.18 de-immunized VH4 (SEQ ID NO: 682):
EVQLLQSGPELKKPGASVKISCKASGSSFTGYNMNWVRQAPGQRTEWIGA
IDPYYGGTSYNQKFKGRVTITVDKSSSQAYMHLKSLTSEDTAVYYCVSGM
EYWGQGTTVTVSS 14.18 de-immunized VK4 (SEQ ID NO: 683):
DVVMTQSPGTLPVSLGERATISCRSSQSLVHSNGNTYLHWYLQKPGQSPK
MLIHKVSNRFSGVPDRFSGSGSGTDFTLTISRLEAEDMAVYFCSQSTHVP
PLTFGGGTKVEIK 14.18 de-immunized VH5 (SEQ ID NO: 684):
EVQLLQSGPELKKPGASVKISCKASGSSFTGYNMNWVRQAIGQRLEWIGA
IDPYYGGTSYNQKFKGRVTITVDKSSSQAYMHLKSLTSEDTAVYYCVSGM
EYWGQGTTVTVSS 14.18 de-immunized VK5 (SEQ ID NO: 685):
DVVMTQSPGTLPVSLGERATISCRSSQSLVHRNGNTYLHWYLQKPGQSPK
MLIHKVSNRFSGVPDRFSGSGSGTDFTLTISRLEAEDMAVYFCSQSTHVP
PLTFGGGTKVEIK 14.18 VH mouse, peptide threaded (Mo PT):
(SEQ ID NO: 686):
EVQLVQSGPEVEKPSASVKISCKASGSSFTGYNMNWVRQAIGKSLEWIGA
IDPYYGGTSYNQKFKGRATLTVDKSSSTAYMHLKSLTSEDTAVYYCVSGM
EYWGQGTTVTVSS 14.18 VK mouse, peptide threaded (Mo PT):
(SEQ ID NO: 687):
DVVMTQTPGSLPVSAGDQASISCRSSQSLVHRNGNTYLHWYLQKPGQSPK
LLIHKVSNRFSGVPDRFSGSGSGTDFTLKISRVEAEDSGVYFCSQSTHVP
PLTFGAGTKLELK 14.18 VH mouse (SEQ ID NO: 688):
EVQLLQSGPELEKPSASVMISCKASGSSFTGYNMNWVRQNIGKSLEWIGA
IDPYYGGTSYNQKFKGRATLTVDKSSSTAYMHLKSLTSEDSAVYYCVSGM
EYWGQGTSVTVSS 14.18 VK mouse (SEQ ID NO: 689):
DVVMTQTPLSLPVSLGDQASISCRSSQSLVHRNGNTYLHWYLQKPGQSPK
LLIHKVSNRFSGVPDRFSGSGSGTDFTLKISRVEAEDLGVYFCSQSTHVP
PLTFGAGTKLELK The foregoing description and the examples are intended as illustrative, and are not to be taken as limiting. Still other variants within the spirit and scope of this invention are possible and will readily present themselves to those skilled in the art.

The invention claimed is:

1. A modified fusion protein comprising an anti-EGFR immunoglobulin moiety and a cytokine polypeptide moiety linked together directly or through a linker peptide;

wherein the anti-EGFR immunoglobulin moiety comprises an anti-EGFR immunoglobulin variable region polypeptide which comprises an amino acid residue sequence selected from the group consisting of SEQ ID NO: 646, SEQ ID NO: 647, SEQ ID NO: 648, SEQ ID NO: 649, SEQ ID NO: 650, SEQ ID NO: 651, SEQ ID NO: 652, SEQ ID NO: 653, SEQ ID NO: 654, SEQ ID NO: 655, SEQ ID NO: 656, and SEQ ID NO: 657.

2. The modified fusion protein of claim 1, wherein the cytokine polypeptide moiety is IL-2.

3. The modified fusion protein of claim 1, wherein the cytokine polypeptide moiety is TNF$\alpha$.

4. A pharmaceutical composition comprising the modified fusion protein of claim 1, optionally together with a suitable carrier, excipient, or diluent.

5. A pharmaceutical composition comprising the modified fusion protein of claim 2, optionally together with a suitable carrier, excipient, or diluent.

6. A pharmaceutical composition comprising the modified fusion protein of claim 3, optionally together with a suitable carrier, excipient, or diluent.

* * * * *